(12) United States Patent
Michaels et al.

(10) Patent No.: US 6,205,404 B1
(45) Date of Patent: Mar. 20, 2001

(54) DNA-BINDING PROTEINS OF THE ZINC-FINGER CLASS

(76) Inventors: George S. Michaels, 13516 Sloan St., Rockville, MD (US) 20853; Raik-Hiio Mikelsaar, Jakobsoni Street 11-4, 51005 Tartu (EE); Richard J. Feldmann, 17800 Mill Creek Dr., Derwood, MD (US) 20855-1019

(*) Notice: Subject to any disclaimer, the term of this patent is extended or adjusted under 35 U.S.C. 154(b) by 0 days.

(21) Appl. No.: 09/253,396

(22) Filed: Feb. 19, 1999

Related U.S. Application Data

(60) Provisional application No. 60/075,466, filed on Feb. 20, 1998.

(51) Int. Cl.$^7$ .............................. G01N 31/00; G06F 15/00
(52) U.S. Cl. ............................................... 702/27; 712/200
(58) Field of Search ................................ 435/6; 536/23.5, 536/24.31; 702/27; 706/47; 712/200

(56) References Cited

U.S. PATENT DOCUMENTS 5,579,250 * 11/1996 Balaji et al. ............................ 702/19

OTHER PUBLICATIONS

Choo et al., "In vivo repression by a site–specific DNA–binding protein designed against an oncogenic sequence," Nature, (1994), vol. 372, pp. 642–645.*

Pomerantz et al., "Structure–Based Design of Transcription Factors," Science, (1995), vol. 267, pp. 93–96.*

Choo et al., "Selection of DNA binding sites for zinc fingers using rationally randomized DNA revels coded interactions," Proc. Natl. Acad. Sci. USA, (1994), vol. 91, pp. 11168–11172.*

* cited by examiner

*Primary Examiner*—John S. Brusca
*Assistant Examiner*—Young Kim
(74) *Attorney, Agent, or Firm*—White & Case LLP

(57) ABSTRACT

The invention is directed to the design of DNA-binding proteins (DBP's) with capabilities of binding to any predetermined target double-stranded DNA sequence. Disclosed are the rules for design of the proteins; an algorithm for screening for the optimal DBP's; a computer system employing the rules and the algorithm; general formulae encompassing the proteins; and methods of use of the proteins.

14 Claims, 27 Drawing Sheets

FIG. 1A

MKR2 fingers

```
1                         TYR GLY CYS ASP GLU CYS GLY LYS THR
   PHE ARG GLN SER SER SER LEU LEU LYS HIS GLN ARG ILE HIS
2  THR GLY GLU LYS PRO TYR THR CYS ASN VAL CYS ASP LYS HIS
   PHE ILE GLU ARG SER SER LEU THR VAL HIS GLN ARG THR HIS
3  THR GLY GLU LYS PRO TYR LYS CYS HIS GLU CYS GLY LYS ALA
   PHE SER GLN SER MET ASN LEU THR VAL HIS GLN ARG THR HIS
4  THR GLY GLU LYS PRO TYR GLN CYS LYS GLU CYS GLY LYS ALA
   PHE ARG LYS ASN SER SER LEU ILE GLN HIS GLU ARG ILE HIS
5  THR GLY GLU LYS PRO TYR LYS CYS HIS ASP CYS GLU LYS ALA
   PHE SER LYS ASN SER SER LEU THR GLN HIS ARG ARG ILE HIS
6  THR GLY GLU LYS PRO TYR GLU CYS MET ILE CYS GLY LYS HIS
   PHE THR GLY ARG SER SER LEU THR VAL HIS GLN VAL ILE HIS
7  THR GLY GLU LYS PRO TYR GLU CYS THR GLU CYS GLY LYS ALA
   PHE SER GLN SER ALA TYR LEU ILE GLU HIS ARG ARG ILE HIS
8  THR GLY GLU LYS PRO TYR GLU CYS ASP GLN CYS GLY LYS ALA
   PHE ILE LYS ASN SER SER LEU ILE VAL HIS GLN ARG ILE HIS
9  THR GLY GLU LYS PRO TYR GLN CYS ASN GLU CYS GLY LYS PRO
   PHE SER ARG SER THR ASN LEU THR ARG HIS GLN ARG THR HIS
```

Kruppel fingers

```
                   PHE THR CYS LYS ILE CYS SER ARG SER
   PHE GLY TYR LYS HIS VAL LEU GLN ASN HIS GLU ARG THR HIS
   THR GLY GLU LYS PRO PHE GLU CYS PRO GLU CYS ASP LYS ARG
   PHE THR ARG ASP HIS HIS LEU LYS THR HIS MET ARG LEU HIS
   THR GLY GLU LYS PRO TYR HIS CYS SER HIS CYS ASP ARG GLN
   PHE VAL GLN VAL ALA ASN LEU ARG ARG HIS LEU ARG VAL HIS
   THR GLY GLU LYS PRO TYR THR CYS GLU ILE CYS ASP GLY LYS
   PHE SER ASP SER ASN GLN LEU LYS SER HIS MET LEU VAL HIS
   THR GLY GLU LYS PRO
```

FIG. 1B

DNA-BINDING PROTEINS OF THE ZINC-FINGER CLASS

This application claims the benefit of U.S. Provisional Application No. 60/075,466, filed Feb. 20, 1998.

BACKGROUND OF THE INVENTION

A superfamily of eukaryotic genes encoding potential nucleic-acid-binding proteins contains zinc-finger (ZF) domains of the $Cys_2$-$His_2$ ($C_2H_2$) class. Proteins that have these characteristic structural features play a key role in the regulation of gene expression[1-4]. Sequence comparisons, mutational analyses, and a recent crystallographic investigation have revealed that each finger domain, as a rule, interacts with the major groove of B-form DNA through contacts with some or all three base pairs within a DNA triplet. These base-specific interactions are mediated through amino acid (AA) side chains at specific positions in the a-helical region [5-10] of the protein domain.

Although the AA sequences of more than 1,300 ZF motifs have been identified, the exact DNA-binding sites are known only for a few proteins. The available information on DNA contact regions concerns mainly guanine-cytosine-rich strands [5-9] and fewer adenine-thymine-rich sites [11,12]. On the basis of experimental data, the first proposals for rules relating ZF sequences to preferred DNA-binding sites have been made [13,14]. However, no general rules for ZF protein-DNA recognition have been proposed. This is likely due to the fact that neither computer modeling [2,3,5] nor crystallographic analysis [7] have provided enough information on the overall structural variety in the ZF-DNA contact region.

Using physical atomic-molecular models to characterize the steric conditions in the specific contact positions for different ZF-DNA interactions, an objective of the work leading to the present invention was to determine a set of general rules for ZF-DNA recognition for the $C_2H_2$ class of ZF domains. Once this objective had been reached, the work of the invention plan was to develop an algorithm, and a computer system using the algorithm, to design effective zinc-finger DNA-binding polypeptides. The achievement of these goals represents a major advance of knowledge in the field, knowledge characterized by the disclosures of Rebar, et. al. and Beerli, et. al. [15,16]. These two disclosures are concerned with the selection, using the phage display system, of specific zinc fingers with new DNA-binding specificities. On the other hand, the present disclosure is concerned with the design of DNA-binding proteins for any given DNA sequence.

SUMMARY OF THE INVENTION

The invention is directed to the design and specification of DNA-binding proteins binding via $C_2H_2$ zinc-finger motifs (DBP's or, individually, a DBP). On the basis of the studies described herein, general rules for optimizing such binding have been determined, and a formula describing the class of DBP's having optimal DNA-binding properties has been constructed. Furthermore, a program has been developed, based on the rules, which affords the design of DBP's with such high binding affinity for any given DNA sequence. Lastly, rules have been determined for the design of DBP's which, while not having optimal binding, do have significant and useful DNA-binding properties.

BRIEF DESCRIPTION OF THE DRAWINGS

FIG. 1 depicts the alignment of ZF domains in various known DBP's. TFIIIA fingers 1–9 are shown as SEQ ID NOS: 207–215, respectively, in the Sequence Listing; Xenopus Xfin finger 31 is shown as SEQ ID NO: 216; the ADRI finger is shown as SEQ ID NO: 217; MKR2 fingers 1–9 are shown as SEQ ID NOS: 218–226, respectively; and Kruppel fingers 1–5 are shown as SEQ ID NOS: 227–231, respectively.

DETAILED DESCRIPTION OF THE INVENTION

Figure 2:
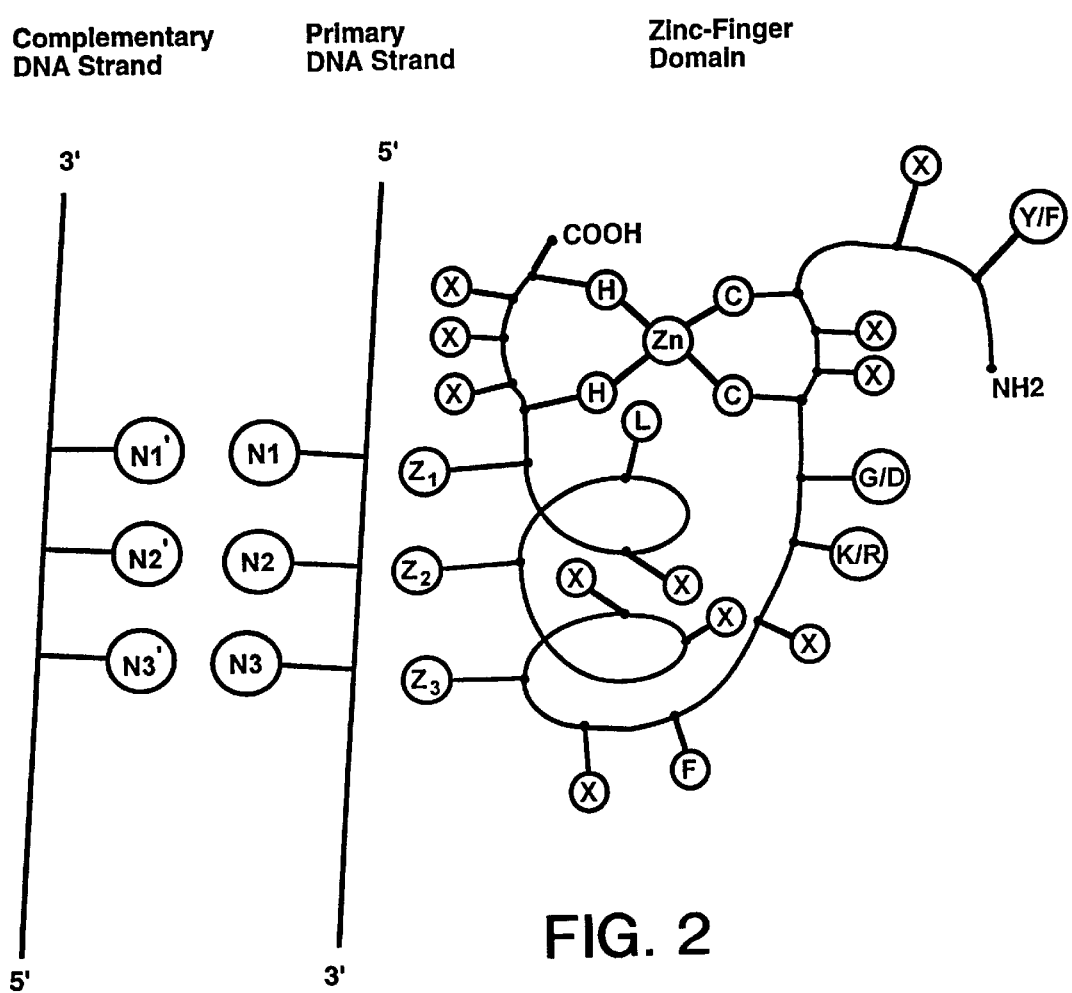
FIG. 2 is a schematic representation of the interaction between a target DNA triplet and a single ZF domain.

The general rules governing the binding of $C_2H_2$ ZF motifs to DNA were developed by using a combination of the database analysis of the homologies between 1,851 possible ZF domains and physical molecular modeling of the interaction of a DBP model with a DNA model containing all 64 possible base-pair triplets. The DBP model approximates the size and shape of a half-gallon jug of milk. The DNA model is approximately four feet long and one foot in diameter. The axis of the DNA model is horizontal and can be rotated to observe each of the 64 base-pair triplets. By moving the DBP model in and out with respect to the DNA model one can observe the amino acid and nucleic acid contacts.

Although the following description details the scientific precedents of this invention, the completeness of the rule set governing the DBP-DNA interaction could have only been obtained by the continual, derivative interplay of data base analysis and physical modeling during the invention period. Observations as to the conservation and variability of amino acids at various places in the ZF motif were embodied, first, by constructing a physical model of the ZF motif and, then, by physically modeling the interaction of a specific DBP with a designated DNA bp triplet. The physical modeling indicated patterns of amino acid and nucleic acid interaction which led to further analysis of the database. Iterations of this interplay between database analysis and physical modeling enabled conceptual refinement and expansion of the nature of contact patterns. As these patterns emerged, systematic variation of the amino acids in the ZF motif was undertaken for each of the 64 base-pair triplets. The physical modeling of the interaction between a DBP and DNA was efficient because alternative amino acids could be easily introduced into the ZF motif and the resulting protein physically modeled against the DNA. Hydrogen bonding, and water and hydrophobic contacts could then be modeled, clearly determined and counted very quickly. From this physical modeling a general set of rules was developed which incorporates criteria for the design of DBP's that specifically interact with DNA.

Figure 1A:
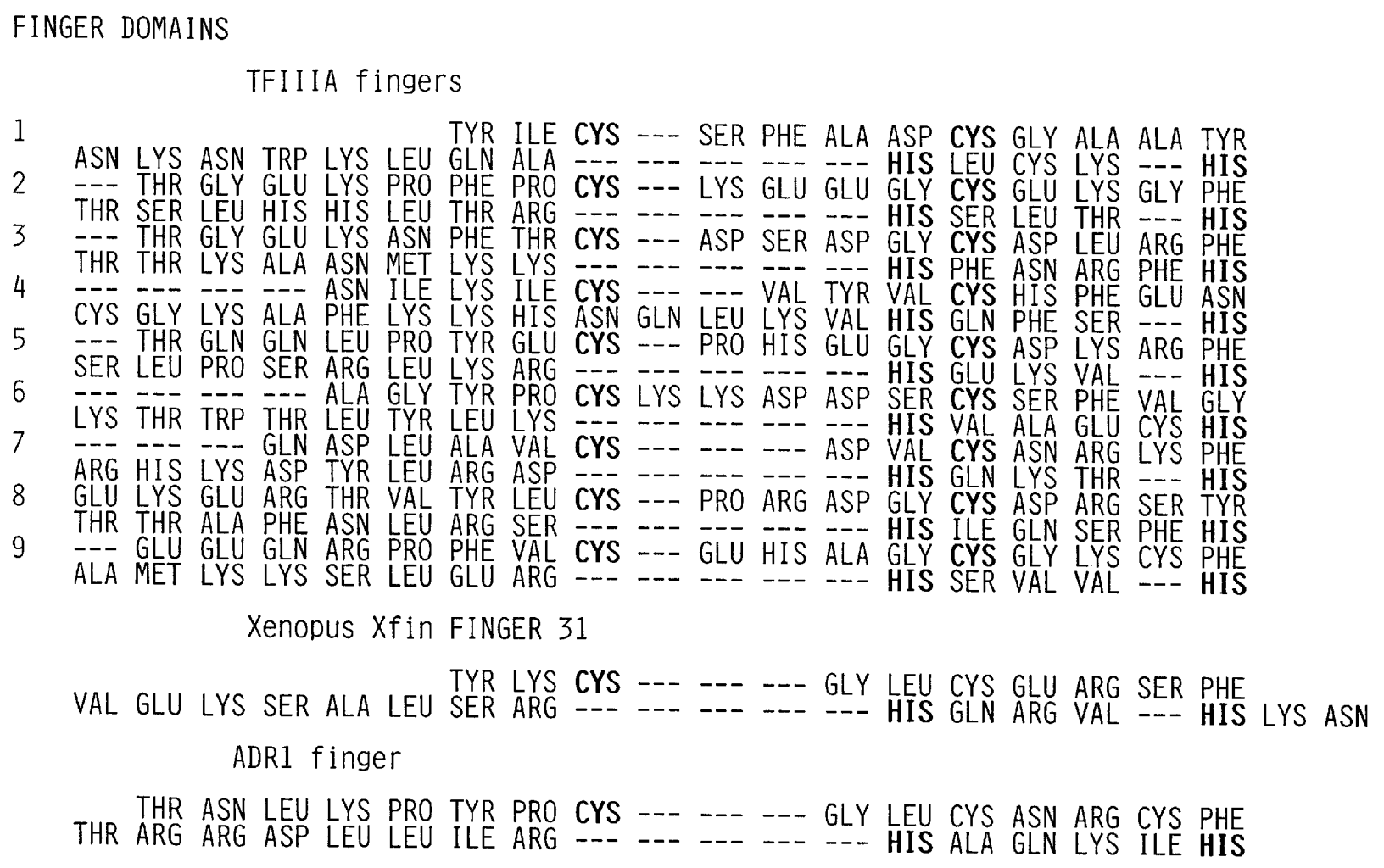

The utility of ZF sequence analysis and alignment is illustrated by FIG. 1. The TFIIIA protein is widely used as a model for ZF proteins both in terms of physical measurement and modification and theoretical data analysis. For each of the nine zinc-finger domains the TFIIIA amino acid sequence in this figure has been aligned so that the zinc-binding amino acids, the two cysteines (CYS) and the two histidines (HIS), are aligned in four columns. In order to achieve this alignment dashes must be inserted into the sequence at various places to provide for domains which have additional amino acids. The same type of alignment has been done for ZF protein MKR2 and the Kruppel proteins. The MKR2 sequence alignment is very compact; there is no need for any insertions, since all of its ZF domains are of the same size. Compared to TFIIIA, MKR2 acts as a much more uniform model for studying the interaction of the amino acids of the protein with the bases of the specific double-stranded DNA. To arrive at the present invention, MKR2 has been used exclusively as the sequence basis for deducing the general rules which govern DBP-DNA interactions.

The crystallographic analysis of a complex containing three ZFs from ZF protein Zif268 and a consensus DNA-binding site helped identify the localization of ZF-B-DNA recognition sub-sites [7]. Because the mutagenesis and sequence investigation results are in accordance with crystal structure data, it is reasonable to expect that the same contact regions also participate in the interaction of other ZF-DNA complexes [5,6,8-10]. Thus, it has been assumed that the following ZF components of a ZF protein play a key role in the anti-parallel DNA reading process: 1) the AA immediately preceding the a-helical region of the protein; 2) the third residue within the a-helical region, i.e., that immediately preceding constant leucine; and, 3) the sixth residue of this region, i.e., that immediately preceding invariant histidine.

These components are indicated below as $Z_3$, $Z_2$ and $Z_1$, respectively, in the generalized ZF sequence (a-helical and b-structural regions are underlined) given in Formula I:

Formula I

Y/F X C X$_{2-4}$ C G/D K/R XF X Z$_3$ X X Z$_2$ L X Z$_1$ H X$_{3-5}$H T/S G/E X$_{0-2}$ E K/R P

β- structural region          α- helix (SEQ ID NO:1)

wherein X is any amino acid; $X_{2-4}$ is a peptide 2 to 4 amino acids in length; $X_{3-5}$ is a peptide 3 to 5 amino acids in length; $X_{0-2}$ is a peptide 0 to 2 amino acids in length and C, D, E, F, G, H, K, L, P, R, S, T and Y designate specific amino acids according to the standard single-letter code. Pairs of letters separated by "/" indicate that the position can be filled by either of the two specific amino acids designated.

Keeping in mind the above formula, one can envision the formation of antiparallel, trinucleotide-peptide complexes with three (first, second and third) contact positions as follows:

5'—N$_1$—N$_2$—N$_3$—3'

COOH—Z$_1$—Z$_2$—Z$_3$—NH$_2$

The crystallographic investigation of the Zif268-DNA complex also gave indications of the way the contact groups interact. Pavletich and Pabo [7] concluded that Zif268 forms 11 critical hydrogen bonds (H-bonds) with the bases of the coding DNA strand in the major groove. Two arginine residues in the first contact positions (see the designations of positions above) make H-bonds with the N7 and O6 atoms of the guanine. Three arginine residues hydrogen bond in the same way with guanine in the third contact position. In addition, each arginine residue in this position forms lateral H-bond, salt bridge interactions with carboxylate groups of aspartic acid occurring as the second residue in the a-helix. The N6 atom of the histidine residue in the middle contact position of the second ZF of Zif268 donates an H-bond to the N7 or O6 atom of guanine. The role of arginine and histidine residues in the interaction with guanine in ZF polypeptide-DNA complexes is confirmed by experiments of directed mutagenesis [5,6,9,14]. The crystallographic investigations of DNA-binding domains of lambda and phage 434 repressors, complexed with corresponding operator sites, revealed that guanine can also be H-bonded by lysine, asparagine, glutamine and serine residues [17,18]. No doubt, the remaining polar AA's—threonine and tyrosine—are able to form analogous bonds with guanine.

In fingers 1 and 3 of the Zif268-DNA complex, the second (middle) critical position is occupied by a glutamic acid that does not contact the cytosine at the corresponding region in the DNA [7]. However, ZF protein-DNA binding assays have shown that in natural binding sites this interaction does occur with both glutamic acid and aspartic acid [5,6,9,14, 19]. Desjarlais and Berg [14] proposed an H-bonding formula for the interaction between cytosine and aspartic acid. The authors emphasized that the preference for aspartic or glutamic acid in the interaction with cytosine depends on the presence of glutamine or arginine in the third contact position ($Z_3$), and serine or aspartic acid in the second position ($Z_2$). The mutagenesis experiments of Nardelli et al. [5] reveal that cytosine can interact with a glutamine residue. This may also be true for asparagine, which has similar polar groups. Cytosine should also be capable of making an H-bond with the hydroxyl oxygen atom in serine and threonine residues.

Thymine in the Zif268-DNA complex does not seem to participate in the recognition process. However, the crystal structure investigations of the lambda repressor, DNA-binding-domain DNA and engrailed homeodomain-DNA complexes, as well as ZF protein-DNA binding assays, demonstrate that thymine can make both hydrophobic contacts with non-polar residues (alanine, leucine, isoleucine, valine) and H-bonds with polar AA's (lysine, arginine, glutamine) [8,11,14,17,20].

The X-ray crystallographic studies of lambda and phage 434 repressor, DNA-binding domain complexes with corresponding operator sites revealed that an adenine base forms two H-bonds to glutamine: 1) the amide $NH_2$-group of the glutamine side chain donates an H-bond to the N7-atom of adenine and 2) the amide O-atom accepts an H-bond from the N6 atom [17,18]. Similar H-bonds have been found between adenine and asparagine residues in the two homeodomain complexes [20,21]. ZF protein-DNA binding assays also indicate, that in ZF contact positions, adenine makes strong interactions with both glutamine and asparagine [8,11,12,14]. Considering that glutamic and aspartic acid carboxylic groups have O-atoms capable of accepting H-bonds as do glutamine and asparagine amide O-atoms, one may suppose that adenine can form a single H-bond with both glutamic and aspartic acid. Indeed, Letovsky and Dynan [19] have shown in a directed mutagenesis investigation that transcription factor Sp1, containing a glutamic acid residue in the central contact position of the ZF, binds only 3-fold more weakly to the adenine-substituted variant (-GAG-) than to the wild consensus recognition site (-GCG-). In addition, Desjarlais and Berg [14] and Berg [8] think it probable that adenine can (like guanine in the Zif268-DNA complex) make one H-bond to a histidine residue. It is likely that not only histidine but also other polar amino acids (arginine, lysine, tyrosine, serine and threonine) are capable of forming an H-bond to atom N7 of adenine.

A database of potential ZF protein domains, containing 1,851 entries, has been assembled. This database was used computationally to observe the homologies between the ZF domains.

Several years ago Seeman et al. [22] concluded that a single H-bond is inadequate for uniquely identifying any particular base pair, as this leads to numerous degeneracies. They proposed that fidelity of recognition may be achieved using two H-bonds, as occurs in the major groove when asparagine or glutamine binds to adenine, and arginine binds to guanine.

On the basis of the above-given results, it was reasonable to test, using the models described herein, base recognition at the ZF contact positions of the following AA's:

1) guanine—R, H, K, Y, Q, N, S, T;
2) cytosine—E, D, Q, N, S, T;
3) thymine—I, L, V, A, R, H, K, Y, Q, N, S, T;
4) adenine—Q, N, E, D, H, R, K, Y, S, T Plastic space-filling atomic-molecular and ionic models [23,24] have been used to build ZF-DNA complex imitations. These molecular models were chosen due to the extraordinary firmness of their connectors, their convenient scale (1 cm=1 Å=0.1 nm) and their improved theoretical parameters which were very suitable for the modeling of macromolecules. New modules of tetrahedral carbon atoms, with bond angles 100° and 105°, dihedral oxygen atoms (120°) and tetrahedral phosphorus atoms (102° and 118°), maintained the exact modeling of deoxyribose puckering and sugar-phosphate chain conformation in the B-DNA model. Peptide bonds in the DBP models were imitated by the fixing, to each other, of special modules of carbon atoms (bond angles 116°, 120.5° and 123.5°) and nitrogen atoms (122° and 119°). The zinc ion was represented in the model by a sphere (R=0.85 cm) fixed tetrahedrally to N and S atom modules of ZF histidine and cysteine residues. A long horizontal 34-base B-form DNA model with laterally-fixed DBP models was used for docking experiments.

In the first stage of the subject investigation, the models of Zif268 fingers 1, 2 and 3 were assembled, and the general spatial orientation of the ZF-B-DNA complex was observed. In the second stage, the steric fitness of all 64 nucleotide triplets to the different combinations of the above-mentioned AA's in the critical positions of the ZF-DNA complex was modeled.

A plastic molecular model of the Zif268 peptide-DNA complex was assembled on the basis of crystallographic data [7]. After the imitating of ZF-DNA backbone contacts and H-bonds between AA and bases in the major groove, it was confirmed that the overall arrangement of Zif268 is antiparallel to the DNA strand. The most steady ZF-DNA, nonspecific interaction seems to be the H-bond between a phosphodiester oxygen atom and the first invariant histidine residue fixed to the $Zn^{2+}$ ion. A conserved arginine on the second b strand also contacts phosphodiester oxygen atoms on the primary DNA strand. However, fingers 2 and 3 of Zif268 contact equivalent phosphates with respect to the 3-bp sub-sites, whereas the finger-1 H-bond is shifted by one nucleotide. Another four ZF-DNA backbone contacts made by arginine and serine residues are even more irregular in relation to the ZF modular structure.

All 11 critical H-bonds found in the Zif268-DNA crystal complex have been observed in the plastic models. As expected, the threonine residue in the first contact position of the second finger was too far from thymine to make an H-bond. However, differing from the results of crystal structure analysis, the model investigation clearly indicated the possibility of hydrogen bonding between a glutamic acid residue and cytosine in the second contact position of fingers 1 and 3.

It is noteworthy that, of the six guanine-AA contacts in recognition positions observed in the Zif268-DNA crystal structure, five were made with arginine and only one with histidine. It is even more interesting that this histidine-guanine interaction was the only one in the central-specific position. Considering the smaller size of histidine in comparison with arginine, it may be supposed that the middle position has steric constraints prohibiting contact between guanine and the larger arginine residue, although, due to its capability of forming two H-bonds, the latter pairing should be energetically favored.

To investigate the spatial conditions in different recognition positions, a B-DNA model was built which contained, in the primary strand, 1) the triplet GGG, and 2) models of ZF α-helical protein fragments (including the AA immediately preceding the a-helix) with a) side groups of the first Zn-binding histidine and b) groups for critical AA triplets $R_1R_2R_3$ and $R_1H_2R_3$. The models of a-helical fragments were fixed to the B-DNA model by an imitation of an H-bond joining a phosphodiester oxygen atom with a histidine residue. Specific base-AA contacts were then tested in these complexes. It was elucidated that only the complex GGG-Ri$H_2R_3$ contains the contact groups in positions corresponding to the distances of critical H-bonds found in the Zif268-DNA crystal structure. The complex GGG-$R_1R_2R_3$ is sterically unfavorable; molecular modeling reveals that, although in the outer contact positions guanine and arginine can be joined by two H-bonds, in the middle position such a pair cannot be included due to the limited space.

Observations derived from the physical models confirmed the supposition of steric constraints for some AA-base contacts in the central contact position. In the case of the complex $G_1G_2G_3$—$R_1H_2R_3$, the following approximate distances from guanine N7 and O6 atoms to the $C_\alpha$ atoms of corresponding AA's have been determined: $G_1N7$—$R_1$=7 Å, $G_1O6$—$R_1$=8 Å, $G_2N7$—$H_2$=5.5 Å, $G_2O6$ $H_2$=6.5 Å, $G_3N7$—$R_3$=8 Å and $G_3O6$—$R_3$=7 Å.

Using the models, the investigation of B-DNA and a-helix basic structure elucidated the molecular basis for steric constraints in the second ZF-DNA recognition position. Joining, by a straight line, the analogous atomic groups (for example, N7 atoms of guanine) of the first and third base in the DNA triplet in the major groove results in the corresponding group of the middle (second) base being distanced from this line by about 1.5 Å. Similarly, joining the $C_\alpha$ atoms of the AA's in the first and third contact positions of the ZF by such a line results in the $C_\alpha$ atom in the middle position also being at a distance of about 1.5 Å. Thus, the space allowed for a critical AA in the middle contact position is compressed from both sides approximately 1.5 Å.

Analysis of the above-given data on the ZF-DNA backbone contacts, as well as observations derived from the models, led to the conclusion that there are considerable differences in spatial conditions between first and third ZF-DNA recognition positions. In the first position the $C_\alpha$ atom of the AA is distanced about 6.5 Å from the phosphodiester oxygen atom where the ZF protein is fixed to the DNA backbone by the invariant histidine residue. Due to the steady fixing of this ZF α-helical part by histidine, the freedom of conformational rearrangements in the first contact position is limited: the $C_\alpha$ atom, with corresponding side chain, can be moved 2–3 Å "up and down" in the plane of the base where it is localized in the primary DNA strand or, alternatively, 1–2 Å perpendicularly to this plane.

On the other hand, the fixing of the N-terminal end of the ZF α-helical region to the DNA backbone seems to be rather loose and variable, therefore allowing relatively large rearrangements for the $C_\alpha$ atom and the corresponding AA in the third contact position. The latter contact position is favored by the fact that the $C_\alpha$ atom in this position is more distant from the main fixation place (about 10.5 Å from the phosphodiester atom bound to the histidine residue), and the corresponding AA in this position is not a part of the α-helix. The most important finding is that, due to the above-described circumstances, the critical AA in the third contact site can apparently occupy very different positions in the corresponding bp plane. This means this residue may, in certain complexes, be very close to the base of the complementary DNA strand. One of the reasons for the appearance of such a geometrical configuration is that the typical, right-handed helical twist of B-DNA makes the complementary base on the nucleic acid second strand in the third contact site even more accessible than the main base on the primary chain. Molecular modeling clearly shows that in the third, and also partially in the second contact position, this DNA strand is capable of participating in the ZF-nucleic acid recognition process. In the Zif268-DNA crystal complex, the α-helix of each ZF domain, which is bound only to the DNA primary strand, is tipped at about a 45° angle with respect to the plane of the base pairs [7]. In cases wherein the second DNA strand, via critical H-bonds involving the third and second contact positions, is involved in the reading process, the direction of the α-helix axis should be even more perpendicular to the base pair plane.

Thus, this more detailed investigation of ZF-DNA-complex imitations, through use of physical molecular models, shows that steric conditions in each of the three contact regions are different. These steric conditions are reflected in the ZF-DNA recognition rules.

On the basis of information obtained above, which yielded a general observation of steric conditions in the ZF-DNA recognition process, an extensive model study of various AA-base combinations in the critical contact positions was undertaken. The results of this investigation are presented both as the ZF-DNA reading code and main rules for recognition (Tables 1, 2 and 3). The rules are in good accordance with crystallographic, directed mutagenesis, DNA-binding and sequence analysis data.

With reference to the sequence of Formula I and the 2-dimensional structure diagram in FIG. 2 (which provides a schematic representation of a zinc-finger domain and its interaction with a DNA strand), the studies confirmed the identity of the three critical contact positions in a given zinc-finger domain as follows:

1) between the first nucleotide in the triplet and the first AA preceding the constant histidine at the COOH end of the α-helix;
2) between the second nucleotide in the triplet and the fourth AA preceding the constant histidine at the COOH end of the α-helix; and,
3) between the third nucleotide in the triplet and the seventh AA preceding the constant histidine at the COOH end of the α-helix.

Steric conditions in the three contact sites of the ZF-DNA recognition complexes are different. The first contact position is relatively large and strictly fixed, which enables the binding of a longer AA to bases on the primary DNA strand with sufficient specificity and affinity. The second position is compressed and can accommodate smaller AA's with somewhat lower specificity and affinity. The third position allows considerable conformational rearrangements including the contacts with the complementary DNA strand.

In Table 1, for each nucleotide of a given DNA triplet on the primary strand, both main (Column A) and alternative (Column B) base-binding AA's are presented. Both specificity and affinity were considered in including a residue in Column A. As was proposed already by Seeman et al. [22], the fidelity of recognition is better maintained, in the case of purine bases (guanine and adenine), because they occupy a greater portion of the major groove and offer more hydrogen bonding sites than the pyrimidines. Therefore, the strongest AA interactions appeared to be those of arginine, glutamine and asparagine, each binding by two H-bonds to either guanine or adenine. The affinities of aspartic acid, glutamic acid, asparagine and glutamine were frequently enhanced by the formation of water bridges between carboxylate or amide oxygen atoms and DNA backbone, phosphodiester oxygen atoms. Although van der Waals interactions are relatively weak, they can play a certain role in recognition of the thymine methyl group by hydrophobic AA's (alanine, valine, leucine and isoleucine).

As indicated in Table 1, in many ZF-DNA complexes the base recognition in the nucleotide triplet of the primary DNA strand occurs not entirely via the primary strand, but by binding simultaneously to both the primary and complementary strands, or even exclusively to the complementary strand. Without "help" from the complementary DNA strand, the binding of critical AA's to nucleotides of the primary DNA chain would be too weak, in the case of several triplets, to realize the recognition process. All possible AA replacements were tested for strength of interaction in the $Z_1$–$Z_3$ positions. Domains with fewer than 2 hydrogen bonds on the primary strand were considered to be unstable.

Table 2 presents the ZF AA triplets having the highest affinity for interaction with corresponding DNA triplets. These ZF triplets contain only the main residues presented in Column A of Table 1. Table 2 also presents the binding energy components (H-bonds, water bridges, van der Waals interactions) maintaining the ZF-DNA recognition process in specific contact regions.

As can be seen from Table 2, the participation of the complementary DNA strand in the process of ZF binding, combined with the number of interactions (H-bonds, water bridges and van der Waals interactions) possible in the three contact regions, when optimal combinations are used, makes it possible to show that a complex formation with all 64 DNA triplets can be achieved. Table 2 shows that the maximal number of H-bonds, the strongest of the three types of interactions, is obtained when the first nucleotide of the triplet is guanine or adenine.

In nucleotide triplets wherein the number of H-bonds possible is less than maximal, the deficiency is often partially compensated by a significant amount of water-bridging between critical AA's and the sugar-phosphate backbone.

Even in cases wherein the first nucleotide of the triplet is thymine, and the number of the H-bonds is lowest, 1) the formation of two ES-bonds between the AA in the $Z_3$ position, and the adenine and complementary thymine in the third contact position, and 2) probably, a single H-bond between thymine and serine or threonine in the second contact position, means that even TTN triplets can bind a ZF protein with sufficient affinity.

In any event, to obtain DBP's of the greatest effectiveness, attention should be paid to having the strongest interactions in the flanking contact points (1 and 3). If weaker combinations must be used, they would have less effect if positioned in the center contact point (2). It is important to note, however, that even weak binding in the contact points is important for establishing specificity.

Table 3 presents the main ZF AA triplets of Table 2, as well as the alternative AA's (shown in Column B of Table 1) which would be also expected to provide effective binding to the respective bases of a given DNA triplet. Table 3 also presents the binding energy components (H-bonds, water bridges, van der Waals interactions) maintaining the ZF-DNA recognition process in specific contact regions.

TABLE 1-Z1

| Codon | Z1 Column A | Z1 Column B | Hydrogen Bonds | Water Contacts | Hydrophobic Contacts |
|---|---|---|---|---|---|
| AAC | Q= | $E^*/R_1$-$K_1$-$N_1$=/$D_1^*$/(H-/Y-/S-/T-) | 6 | 0 | 0 |
| AAG | Q= | $E^*$/R-/K- | 6 | 0 | 0 |
| AAT | Q= | R-/K-/$E^*$ | 6 | 0 | 0 |
| ACC | Q= | $E^*/K_1$- | 6 | 0 | 0 |
| ACT | Q= | E-/$R_1$-/$K_1$- | 6 | 0 | 0 |
| GAA | R= | K-/$H_1$-/$Y_1$-/$Q_1$- | 6 | 0 | 0 |
| GAC | R= | K-/$H_1$-/$Y_1$- | 6 | 0 | 0 |
| GAG | R= | H-/K-/Y-/Q- | 6 | 0 | 0 |
| GAT | R= | H-/K-/Y-/$Q^*$ | 6 | 0 | 0 |
| CCC | R= | H-/K-/Q-/N-/(Y-/S-/T-) | 0 | 0 | |
| GCT | R= | H-/K-/Y-/Q- | 6 | 0 | 0 |
| ACA | Q= | R-/K-/N-/E-/D- | 5 | 1 | 0 |
| ACG | Q= | R-/K-/N-/$E^*$/D- | 5 | 1 | 0 |
| AGA | Q= | $E^*/R_1$-/$K_1$- | 5 | 1 | 0 |
| AGG | Q= | $E^*/R_1$-/$K_1$- | 5 | 1 | 0 |
| CAA | $E^*$ | $Q^*/N_1^*/D_1^*/R_2$-/$K_2$-/$Y_2$-/$S_2$-/$T_2$- | 5 | 1 | 0 |
| CAG | $E^*$ | $Q^*/N^*/D^*/R_2$-/$K_2$- | 5 | 1 | 0 |
| CAT | $E^*$ | $Q^*/R_2$-/$K_2$-/($D^*/N^*$/S-/T-/$Y_2$-) | 5 | 1 | 0 |
| CCC | $E^*$ | $Q^*/N_1^*/D_1^*/R_2$=/$K_2$-/$Q_2^*/N_2^*$ | 5 | 1 | 0 |
| CCT | $E^*$ | $Q^*/R_2$-/$K_2$- | 5 | 1 | 0 |
| GCA | R= | K-/Q-/(H-/Y-/N-/S-/T-) | 5 | 1 | 0 |
| CCG | R= | H-/K-/Y-/Q-/N-/S-/T- | 5 | 1 | 0 |
| CGA | R= | H-/K-/$Q^*/N^*/Y_1$- | 5 | 1 | |
| AAA | R-/K- | | 5 | 0 | 0 |
| AGC | Q= | R-/K-/$E^*$ | 5 | 0 | 0 |
| AGT | Q= | $E^*/R_1$-/$K_1$- | 5 | 0 | 0 |
| GGG | R= | K-/$Q^*$/(H-/Y-/N-) | 5 | 0 | 0 |
| GGG | R= | H-/K-/Y-/$Q^*$N-) | 5 | 0 | 0 |
| GGT | R= | H-/K-/Y-/Q-/N- | 5 | 0 | 0 |
| CAC | $E^*$ | $Q^*/R_2$-/$K_2$- | 4 | 2 | 0 |
| CCA | $E^*$ | $Q^*/R_2$-/$K_2$- | 4 | 2 | 0 |
| CCG | $E^*$ | $Q^*/N^*/D^*/R_2$=/$K_2$- | 4 | 2 | 0 |
| CGA | $E^*$ | $Q^*/N^*/D^*/R_2$=/$K_2$- | 4 | 2 | 0 |
| CGC | $E^*$ | $Q^*/N^*/D^*/R_2$-/$K_2$-/$Y_2$-/$Q_2$-/(S-/T-) | 4 | 1 | 0 |
| CGG | $E^*$ | $Q^*/N^*/D^*/R_2$-/$K_2$-/$Q_3$= | 4 | 1 | 0 |
| CGT | $E^*$ | $Q^*/D_1^*/R_2$=/$K_2$-/$Q_2$- | 4 | 1 | 0 |
| CTA | $E^*$ | $Q^*$ | 3 | 1 | 1 |
| CTC | $E^*$ | $Q^*/N_1$-/$D_1$-/$R_2$-/$K_2$-/$Q_2$-/$N_2$- | 3 | 1 | 1 |
| CTG | $E^*$ | $Q^*/N^*/D^*/R_2$-/$K_2$- | 3 | 1 | 1 |
| CTT | $E^*$ | $Q^*/N^*/D^*/R_2$-/$K_2$-/$Q_3$= | 3 | 1 | 1 |
| TCA | I#/L# | R-/K-/$Q^*$ | 3 | 1 | 1 |
| TCG | I#/L# | R-/K-/$Q^*$ | 3 | 1 | 1 |
| TGA | I#/L# | R-/K-/$Q^*$ | 3 | 1 | 1 |
| TAC | I#/L#/V# | R-/K-/$Q^*$ | 3 | 0 | 1 |
| TGC | I#/$L_1$#/$V_1$# | R-/K-/$H_1$-/$Q_1^*/N_1^*/S_1$-/$T_1$- | 3 | 0 | 1 |
| TCG | I#/L# | R-/K-/$Q^*$ | 3 | 0 | 1 |
| TGT | I# | R-/H-/K-/$Q^*/N^*$/L# | 3 | 0 | 1 |
| TTA | I#/L# | R-/K-/$Q^*/N^*$ | 2 | 0 | 2 |
| TTC | I#/L#/V# | R-/K-/$Q^*/N^*$ | 2 | 0 | 2 |

TABLE 1-Z1-continued

| Codon | Z1 Column A | Z1 Column B | Hydrogen Bonds | Water Contacts | Hydrophobic Contacts |
|---|---|---|---|---|---|
| TTG | I#/L# | R-/K-/Y-/Q* | 2 | 0 | 2 |
| TTT | I#/L# | R-/K-/Q*/N*/$V_1$# | 2 | 0 | 2 |
| ATA | Q= | E*/$R_1$-/$K_1$- | 4 | 0 | 1 |
| ATC | Q= | N-/E*/D*/$R_1$-/$K_1$- | 4 | 0 | 1 |
| ATG | Q= | R-/K-/E-/(H-) | 4 | 0 | 1 |
| ATT | Q= | E*/$R_1$-/$K_1$- | 4 | 0 | 1 |
| GTA | R= | H-/K-/Y-/Q- | 4 | 0 | 1 |
| GTC | R= | H-/K-/Y-/Q* | 4 | 0 | 1 |
| GTG | R= | K-/Q-/$H_1$- | 4 | 0 | 1 |
| GTT | R= | H-/K-/Q-/N-/$Y_1$- | 4 | 0 | 1 |
| TAA | I#/L# | R-/K-/Q-/$V_1$# | 4 | 0 | 1 |
| TAG | I#/L# | R-/K-/Q- | 4 | 0 | 1 |
| TAT | I#/L#/V# | R-/K-/Y-/Q-/N- | 4 | 0 | 1 |
| TCC | I#/L# | R-/H-/K-/Q*/N*/V#/A# | 4 | 0 | 1 |
| TCT | $I_1$#/$L_1$# | R-/H-(K-/Q* | 4 | 0 | 1 | where / separates alternative amino acids
where X without subscript has all its interactions with the primary strand
where $X_1$ has some interactions with the primary strand and some interactions with the complementary strand
where $X_2$ has interaction with the complementary strand
where $X_3$ has interactions with both the primary and complementary strands
where - is one hydrogen bond between the animo acid and the base
where = is two hydrogen bonds between the amino acid and the base
where is one hydrogen bond via a water bridge between the amino acid and the phosphodiester oxygen atom of the backbone
where # is one or more van der Waals contacts between the amino acid and the base
where amino acids in ( ) have interaction with the base of the primary strand where one of two other possible protein-DNA recognition interactions is absent

TABLE 1-Z2

| Codon | Col A | Col B | HB | WC | HC |
|---|---|---|---|---|---|
| CGC | $H_1$- | Q*/N*/S-/T-/$K_1$-/($R_1$=/Y-) | 4 | 1 | 0 |
| CGG | H- | K-/Q*/N*/$R_1$-/(Y-) | 4 | 1 | 0 |
| CCT | H- | Q*/N*/$R_1$-/$K_1$-/(Y-) | 4 | 1 | 0 |
| ATA | I#/L#/V#/A# | S-/T-/$K_1$-/$Q_1$*/$N_1$*/(R-/H-/Y-) | 4 | 0 | 1 |
| ATC | I#/L# | N*/S-/T-/V-/$R_1$-/$H_1$-/$K_1$-/$Y_1$-/$Q_1$*/$R_2$-/$K_2$-/$Q_2$=/$N_2$-/$E_2$*/$D_2$* | 4 | 0 | 1 |
| ATG | I#/L#/V# | S-/T-/$E_2$-/$D_2$-/$Q_3$=/$N_2$=/(R-/H-/K-/Y-) | 4 | 0 | 1 |
| ATT | I#/L#/V# | R-/H-/K-/Y-/Q*/N*/S-/T- | 4 | 0 | 1 |
| GTA | I#/L#/V#/A# | Q*/N*/S-/T-/$R_2$-/$H_1$-/$K_1$-/$E_2$*/$D_2$*/$Q_3$=/$N_3$=/(Y-) | 4 | 0 | 1 |
| GTC | I#/L# | N-/S-/T-/V-/$R_1$-/$H_1$-/$K_1$-/$Q_1$* | 4 | 0 | 1 |
| GTG | I#/L#/V# | Q*/N*/S-/T-/$H_1$-/$K_1$- | 4 | 0 | 1 |
| GTT | I#/L#/V# | Q*/N*/S-/T-/$K_1$-/(R-/H-/Y-/A-) | 4 | 0 | 1 |
| TAA | N= | D*/$R_1$-/$H_1$-/$K_1$-/$Y_1$-/$Q_1$=/$E_1$- | 4 | 0 | 1 |
| TAG | N= | Q=/E*/D*/$R_1$-/$K_1$-/$K_2$- | 4 | 0 | 1 |
| TAT | N= | K-/Q=/N=/E*/D*/S-/T-/$H_2$-/$H_2$-/$K_2$-/$Q_3$=/$N_3$=/(R-/Y-) | 4 | 0 | 1 |
| TCC | $Q_3$=/E* | Q*/N*/D*/S-/T-/$R_2$-/$H_2$-/$K_2$/$Y_2$-/$Q_2$-/$N_2$- | 4 | 0 | 1 |
| TCT | $N_3$=/D* | Q*/N*/D*/S-/T-/$R_2$-/$H_2$-/$K_2$/$Y_2$-/$Q_2$* | 4 | 0 | 1 |
| CTA | I#/L#/V#/A# | S-/T-/$Q_1$=/$N_1$=(H-/K-) | 3 | 1 | 1 |
| CTC | I#/L# | S-/T-/V-/$R_1$-/$H_1$-/$K_1$-/$Y_1$-/$Q_1$*/$N_1$* | 3 | 1 | 1 |
| CTG | I#/L#/V# | N*/S-/T-/$K_1$-/$Q_1$* | 3 | 1 | 1 |
| CTT | I#/L# | Q*/N*/S-/T-/V#/$R_1$-/$H_1$-/$K_1$-/$E_2$-/$D_2$-/$Q_2$=/$N_3$=/(Y-) | 3 | 1 | 1 |
| TCA | D* | Q*/N*/E*/S-/T-/$R_2$=/$H_2$-/$K_2$-/$Y_2$-/$Q_3$=($N_2$= | 3 | 1 | 1 |
| TCG | D* | Q*/N*/E*/S-/T-/$R_2$=/$H_2$-/$K_2$-/$Y_2$-/$S_2$-/$T_2$-/$Q_3$=($N_2$= | 3 | 1 | 1 |
| TGA | N* | Q*/S-/T-/$H_1$-/$K_1$-/(R-/Y-) | 3 | 1 | 1 |
| TAC | N= | D-/$H_1$-/$K_1$-/$Q_1$=/$E_1$*/$k_2$/(R-/Y-) | 3 | 0 | 1 |
| TGC | $H_1$- | Q*/N*/S-/T-/$R_1$=/$K_1$-/$Y_1$- | 3 | 0 | 1 |
| TGG | H- | R-/K-/Q*/N*/$Y_1$- | 3 | 0 | 1 |
| TGT | $H_1$- | N*/S-/T-/$K_1$-/$Y_1$-/$Q_1$*/(R=) | 3 | 0 | 1 |
| TTA | I#/L#/V#/A# | S-/T-/$R_1$-/$H_1$/$K_1$-/$Y_1$-/$E_2$-/$D_2$-/$Q_3$=/$N_3$= | 2 | 0 | 2 |
| TTC | I#/L# | N*/S-/T-V-/A-/$R_1$/$H_1$-/$K_1$-/$Y_1$-/$K_2$-/$Q_3$=/$N_3$= | 2 | 0 | 2 |
| TTG | I#/L#/V# | N*/S-/T-/$H_1$-/$K_1$-/$Q_1$* | 2 | 0 | 2 |
| TTT | I#/L#/V# | Q*/N*/S-/T-/A-/$H_1$-/$K_1$-/(R-/Y-) | 2 | 0 | 2 |
| AAC | $Q_1$= | N=/D*/S-/T-/$R_1$-/$K_1$-/$E_1$*/(H-/Y-) | 6 | 0 | 0 |
| AAG | Q=/N= | R-/H-/K-/E*/D*/$K_2$0 | 6 | 0 | 0 |
| AAT | N= | K-/Q=/E*/D*/$R_1$-/$H_Q$-/$K_2$-/$Q_3$=/$N_3$= | 6 | 0 | 0 |
| ACC | $Q_3$=/E* | D*/S-/T-/$N_3$=/($K_2$-) | 6 | 0 | 0 |
| ACT | $N_3$=/D* | Q*/N*/E*/S-/T-/$K_2$-/$Q_3$= | 6 | 0 | 0 |
| GAA | N= | D*/$R_1$-/$H_1$-/$K_1$-/$Y_1$/$Q_1$=/$E_1$*/$K_2$- | 6 | 0 | 0 |
| GAC | N= | D*/$R_1$-/$H_1$-/$K_1$-/$Y_1$/$Q_1$=/$E_1$*/$K_2$- | 6 | 0 | 0 |
| GAG | N= | Q=/E*/D*/$R_1$-/$H_1$-/$K_1$-/$7_1$-/$K_2$- | 6 | 0 | 0 |
| GAT | Q=/N= | K-/E*/D*/$K_2$-/(R-/H-/Y-) | 6 | 0 | 0 |
| GCC | $Q_3$=/E* | Q*/N*/D*/S-/T-$R_2$/$H_2$-/$K_2$-/$Q_2$-/$N_2$-/$S_2$-/$T_2$- | 6 | 0 | 0 |
| GCT | $N_3$=/D* | Q-/N-/E-/S-/T-/$H_2$-/$K_2$-/$N_2$*/$Q_3$=/($R_2$=/$Y_2$-) | 6 | 0 | 0 |
| ACA | D* | Q*/N*/E*/S-/T-$K_2$- | 5 | 1 | 0 |

TABLE 1-Z2-continued

| Codon | Column A | Column B | Hydrogen Bonds | Water Contacts | Hydrophobic Contacts |
|---|---|---|---|---|---|
| ACG | E*/D* | Q*/N*/S-/T-/R$_2$-/H$_2$/K$_2$-/Y$_2$-/Q$_3$=/N$_3$= | 5 | 1 | 0 |
| AGA | N* | R$_1$-/H$_1$-/K$_1$-/Y$_1$-/Q$_1$* | 5 | 1 | 0 |
| AGG | Q*/N* | R$_1$*/H$_1$*/K$_1$- | 5 | 1 | 0 |
| CAA | N= | D*/S-/T-/R$_1$-/H$_1$-/K$_1$-/Y$_1$-/Q$_1$=/E$_1$* | 5 | 1 | 0 |
| CAG | Q= | N=/E*/D*/R$_1$-/K$_1$-/K$_2$-/Q$_3$= | 5 | 1 | 0 |
| CAT | Q$_1$=/N= | D-/S-/T-/R$_1$-/H$_1$-/K$_1$-/Y$_1$-/E$_1$=/K$_2$-/Q$_3$=N$_3$= | 5 | 1 | 0 |
| CCC | Q$_2$=/E$_1$* | N*/D*/S-/T-/H$_2$-/K$_2$-/N$_3$=/(Y$_2$-) | 5 | 1 | 0 |
| CCT | N$_3$=/D* | Q*/N*/E*/S-/T-/H$_2$-/K$_2$-/Y$_A$-/Q$_3$=/N$_2$= | 5 | 1 | 0 |
| GCA | D* | Q*/N*/E*/S-/T-/R$_2$-/H$_2$-/K$_2$-/Y$_2$-/Q$_3$=/N$_3$= | 5 | 1 | 0 |
| GCG | E*/D* | Q*/N*/S-/T-/K$_2$-/Q$_3$=/N$_3$=/(H$_2$-) | 5 | 1 | 0 |
| GGA | N* | Q*/S-/T-/K$_1$-/(R-/Y-/H-) | 5 | 1 | 0 |
| AAA | N= | D*/R$_1$/H$_1$/K$_1$/Y$_1$/Q$_1$=/E$_1$* | 5 | 0 | 0 |
| AGC | H$_1$- | Q*/N*/S-/T-/R$_1$-/K$_1$-/(R=/Y-) | 5 | 0 | 0 |
| AGT | H$_1$- | Q*/N*/S-/T-/R$_1$-/K$_1$- | 5 | 0 | 0 |
| GGC | H$_1$- | N*/S-/T-/K$_1$-/(R-/K-/7-/Q*) | 5 | 0 | 0 |
| GGG | H- | K-/Q*/N*/S-/T-/Y$_1$-/(R-) | 5 | 0 | 0 |
| GGT | H- | Q*/N*/S-/T-/R$_1$-/K$_1$- | 5 | 0 | 0 |
| CAC | N= | D*/R$_1$-/K$_1$-/Q$_1$=/E$_1$* | 4 | 2 | 0 |
| CCA | D* | N*/S-/T-/Q$_1$*/E$_1$*/K$_2$-/N$_3$= | 4 | 2 | 0 |
| CCG | D* | Q*/N*/E*/S-/T-/K$_2$-/Q$_3$=/N$_3$/(R-/H-/Y-) | 4 | 2 | 0 |
| CGA | N* | Q*/S-/T-/R$_1$=/H$_1$-/K$_1$-/(Y-) | 4 | 2 | 0 | where / separates alternative amino acids
where X without subscript has all its interactions with the primary strand
where X$_1$ has some interactions with the primary strand and some interactions with the complementary strand
where X$_2$ has interaction with the complementary strand
where X$_3$ has interactions with both the primary and complementary strands
where - is one hydrogen bond between the animo acid and the base
where = is two hydrogen bonds between the amino acid and the base
where is one hydrogen bond via a water bridge between the amino acid and the phosphodiester oxygen atom of the backbone
where # is one or more van der Waals contacts between the amino acid and the base
where amino acids in ( ) have interaction with the base of the primary strand where one of two other possible protein-DNA recognition interactions is absent

TABLE 1-Z3

| Z3 Codon | Z3 Column A | Z3 Column B | Hydrogen Bonds | Water Contacts | Hydrophobic Contacts |
|---|---|---|---|---|---|
| AAC | Q= | E*/R$_1$-K$_1$-N$_1$=/D$_1$*/(H-/Y-/S-/T-) | 6 | 0 | 0 |
| AAG | Q= | E*/R-/K- | 6 | 0 | 0 |
| AAT | Q= | R-/K-/E* | 6 | 0 | 0 |
| ACC | Q= | E*/K$_1$- | 6 | 0 | 0 |
| ACT | Q= | E-/R$_1$-/K$_1$- | 6 | 0 | 0 |
| GAA | R= | K-/H$_1$-/Y$_1$-/Q$_1$- | 6 | 0 | 0 |
| GAC | R= | K-/H$_1$-/Y$_1$- | 6 | 0 | 0 |
| GAG | R= | H-/K-/Y-/Q- | 6 | 0 | 0 |
| GAT | R= | H-/K-/Y-/Q* | 6 | 0 | 0 |
| CCC | R= | H-/K-/Q-/N-/(Y-/S-/T-) | 0 | 0 | |
| GCT | R= | H-/K-/Y-/Q- | 6 | 0 | 0 |
| ACA | Q= | R-/K-/N-/E-/D- | 5 | 1 | 0 |
| ACG | Q= | R-/K-/N-/E*/D- | 5 | 1 | 0 |
| AGA | Q= | E*/R$_1$-/K$_1$- | 5 | 1 | 0 |
| AGG | Q= | E*/R$_1$-/K$_1$- | 5 | 1 | 0 |
| CAA | E* | Q*/N$_1$*/D$_1$*/R$_2$-/K$_2$-/Y$_2$-/S$_2$-/T$_2$- | 5 | 1 | 0 |
| CAG | E* | Q*/N*/D*/R$_2$-/K$_2$- | 5 | 1 | 0 |
| CAT | E* | Q*/R$_2$-/K$_2$-/(D*/N*/S-/T-/Y$_2$-) | 5 | 1 | 0 |
| CCC | E* | Q*/N$_1$*/D$_1$*/R$_2$=/K$_2$-/Q$_2$*/N$_2$* | 5 | 1 | 0 |
| CCT | E* | Q*/R$_2$-/K$_2$- | 5 | 1 | 0 |
| GCA | R= | K-/Q-/(H-/Y-/N-/S-/T-) | 5 | 1 | 0 |
| CCG | R= | H-/K-/Y-/Q-/N-/S-/T- | 5 | 1 | 0 |
| CGA | R= | H-/K-/Q*/N*/Y$_1$- | 5 | 1 | |
| AAA | R-/K- | | 5 | 0 | 0 |
| AGC | Q= | R-/K-/E* | 5 | 0 | 0 |
| AGT | Q= | E*/R$_1$-/K$_1$- | 5 | 0 | 0 |
| GGC | R= | K-/Q*/(H-/Y-/N-) | 5 | 0 | 0 |
| GGG | R= | H-/K-/Y-/Q*N-) | 5 | 0 | 0 |
| GGT | R= | H-/K-/Y-/Q-/N- | 5 | 0 | 0 |
| CAC | E* | Q*/R$_2$-/K$_2$- | 4 | 2 | 0 |
| CCA | E* | Q*/R$_2$-/K$_2$- | 4 | 2 | 0 |
| CCG | E* | Q*/N*/D*/R$_2$=/K$_2$- | 4 | 2 | 0 |
| CGA | E* | Q*/N*/D*/R$_2$=/K$_2$- | 4 | 2 | 0 |
| CGC | E* | Q*/N*/D*/R$_2$-/K$_2$-/Y$_2$-/Q$_2$-/(S-/T-) | 4 | 1 | 0 |
| CGG | E* | Q*/N*/D*/R$_2$-/K$_2$-/Q$_3$= | 4 | 1 | 0 |
| CGT | E* | Q*/D$_1$*/R$_2$=/K$_2$-/Q$_2$- | 4 | 1 | 0 |
| CTA | E* | Q* | 3 | 1 | 1 |

TABLE 1-Z3-continued

| Codon | Z3 Column A | Z3 Column B | Hydrogen Bonds | Water Contacts | Hydrophobic Contacts |
|---|---|---|---|---|---|
| CTC | E* | Q*/$N_1$-/$D_1$-/$R_2$=/$K_2$-/$Q_2$-/$N_2$- | 3 | 1 | 1 |
| CTG | E* | Q*/N*/D*/$R_2$-/$K_2$- | 3 | 1 | 1 |
| CTT | E* | Q*/N*/D*/$R_2$-/$K_2$-/$Q_3$= | 3 | 1 | 1 |
| TCA | I#/L# | R-/K-/Q* | 3 | 1 | 1 |
| TCG | I#/L# | R-/K-/Q* | 3 | 1 | 1 |
| TGA | I#/L# | R-/K-/Q* | 3 | 1 | 1 |
| TAC | I#/L#/V# | R-/K-/Q* | 3 | 0 | 1 |
| TGC | I#/$L_1$#/$V_1$# | R-/K-/$H_1$-/$Q_1$*/$N_1$*/$S_1$-/$T_1$- | 3 | 0 | 1 |
| TCG | I#/L# | R-/K-/Q* | 3 | 0 | 1 |
| TGT | I# | R-/H-/K-/Q*/N*/L# | 3 | 0 | 1 |
| TTA | I#/L# | R-/K-/Q*/N* | 2 | 0 | 2 |
| TTC | I#/L#/V# | R-/K-/Q*/N* | 2 | 0 | 2 |
| TTG | I#/L# | R-/K-/Y-/Q* | 2 | 0 | 2 |
| TTT | I#/L# | R-/K-/Q*/N*/$V_1$# | 2 | 0 | 2 |
| ATA | Q= | E*/$R_1$-/$K_1$- | 4 | 0 | 1 |
| ATC | Q= | N-/E*/D*/$R_1$-/$K_1$- | 4 | 0 | 1 |
| ATG | Q= | R-/K-/E-/(H-) | 4 | 0 | 1 |
| ATT | Q= | E*/$R_1$-/$K_1$- | 4 | 0 | 1 |
| GTA | R= | H-/K-/Y-/Q- | 4 | 0 | 1 |
| GTC | R= | H-/K-/Y-/Q* | 4 | 0 | 1 |
| GTG | R= | K-/Q-/$H_1$- | 4 | 0 | 1 |
| GTT | R= | H-/K-/Q-/N-/$Y_1$- | 4 | 0 | 1 |
| TAA | I#/L# | R-/K-/Q-/$V_1$# | 4 | 0 | 1 |
| TAG | I#/L# | R-/K-/Q- | 4 | 0 | 1 |
| TAT | I#/L#/V# | R-/K-/Y-/Q-/N- | 4 | 0 | 1 |
| TCC | I#/L# | R-/H-/K-/Q*/N*/V#/A# | 4 | 0 | 1 |
| TCT | $I_1$#/$L_1$# | R-/H-(K-/Q* | 4 | 0 | 1 | where / separates alternative amino acids
where X without subscript has all its interactions with the primary strand
where $X_1$ has some interactions with the primary strand and some interactions with the complementary strand
where $X_2$ has interaction with the complementary strand
where $X_3$ has interactions with both the primary and complementary strands
where - is one hydrogen bond between the animo acid and the base
where = is two hydrogen bonds between the amino acid and the base
where is one hydrogen bond via a water bridge between the amino acid and the phosphodiester oxygen atom of the backbone
where # is one or more van der Waals contacts between the amino acid and the base
where amino acids in ( ) have interaction with the base of the primary strand where one of two other possible protein-DNA recognition interactions is absent

TABLE 2

| Codon | Z1 Column A | Z2 Column A | Z3 Column A | Hydrogen Bonds | Water Contacts | Hydrophobic Contacts |
|---|---|---|---|---|---|---|
| AAC | Q | Q | R | 6 | 0 | 0 |
| AAG | Q | N/Q | R | 6 | 0 | 0 |
| AAT | Q | N | Q | 6 | 0 | 0 |
| ACC | Q | E/Q | R | 6 | 0 | 0 |
| ACT | Q | D/N | Q | 6 | 0 | 0 |
| GAA | R | N | Q | 6 | 0 | 0 |
| GAC | R | N | E/Q | 6 | 0 | 0 |
| GAG | R | N | R | 6 | 0 | 0 |
| GAT | R | N/Q | Q | 6 | 0 | 0 |
| GCC | R | E/Q | R | 6 | 0 | 0 |
| GCT | R | D/N | Q | 6 | 0 | 0 |
| ACA | Q | D | Q | 5 | 1 | 0 |
| ACG | Q | D/E | R | 5 | 1 | 0 |
| AGA | Q | N | Q | 5 | 1 | 0 |
| AGG | Q | N/Q | R | 5 | 1 | 0 |
| CAA | E | N | Q | 5 | 1 | 0 |
| CAG | E | Q | R | 5 | 1 | 0 |
| CAT | E | N/Q | N/Q | 5 | 1 | 0 |
| CCC | E | E/Q | R | 5 | 1 | 0 |
| CCT | E | D/N | Q | 5 | 1 | 0 |
| GCA | R | D | Q | 5 | 1 | 0 |
| GCG | R | D/E | R | 5 | 1 | 0 |
| GGA | R | N | Q | 5 | 1 | 0 |
| AAA | K/R | N | Q | 5 | 0 | 0 |
| AGC | Q | H | R | 5 | 0 | 0 |
| AGT | Q | H | Q | 5 | 0 | 0 |
| GGC | R | H | R | 5 | 0 | 0 |
| GGG | R | H | R | 5 | 0 | 0 |

TABLE 2-continued

| Codon | Z1 Column A | Z2 Column A | Z3 Column A | Hydrogen Bonds | Water Contacts | Hydrophobic Contacts |
|---|---|---|---|---|---|---|
| GGT | R | H | N/Q | 5 | 0 | 0 |
| CAC | E | N | E | 4 | 2 | 0 |
| CCA | E | D | Q | 4 | 2 | 0 |
| CCG | E | D | R | 4 | 2 | 0 |
| CGA | E | N | Q | 4 | 2 | 0 |
| CGC | E | H | R | 4 | 1 | 0 |
| CGG | E | H | R | 4 | 1 | 0 |
| CGT | E | H | N/Q | 4 | 1 | 0 |
| ATA | Q | A/I/L/V | Q | 4 | 0 | 1 |
| ATC | Q | I/L | E/R | 4 | 0 | 1 |
| ATG | Q | I/L/V | R | 4 | 0 | 1 |
| ATT | Q | I/L/V | Q | 4 | 0 | 1 |
| GTA | R | A/I/L/V | Q | 4 | 0 | 1 |
| GTC | R | I/L | E/R | 4 | 0 | 1 |
| GTG | R | I/L/V | R | 4 | 0 | 1 |
| GTT | R | I/L/V | Q | 4 | 0 | 1 |
| TAA | I/L | N | Q | 4 | 0 | 1 |
| TAG | I/L | N | R | 4 | 0 | 1 |
| TAT | I/L/V | N | Q | 4 | 0 | 1 |
| TCC | I/L | E/Q | R | 4 | 0 | 1 |
| TCT | I/L | D/N | N/Q | 4 | 0 | 1 |
| CTA | E | A/I/L/V | Q | 3 | 1 | 1 |
| CTC | E | I/L | E/R | 3 | 1 | 1 |
| CTG | E | I/L/V | R | 3 | 1 | 1 |
| CTT | E | I/L | Q | 3 | 1 | 1 |
| TCA | I/L | D | Q | 3 | 1 | 1 |
| TCG | I/L | D | R | 3 | 1 | 1 |
| TGA | I/L | N | Q | 3 | 1 | 1 |
| TAC | I/L/V | N | E | 3 | 0 | 1 |
| TGC | I/L/V | H | R | 3 | 0 | 1 |
| TGG | I/L | H | R | 3 | 0 | 1 |
| TGT | I | H | Q | 3 | 0 | 1 |
| TTA | I/L | A/I/L/V | Q | 2 | 0 | 2 |
| TTC | I/L/V | I/L | E/R | 2 | 0 | 2 |
| TTG | I/L | I/L/V | R | 2 | 0 | 2 |
| TTT | I/L | I/L/V | Q | 2 | 0 | 2 | where / separates alternative amino acids

TABLE 3

| Codon | Z1 Column A | Z1 Column B | Z2 Column A | Z2 Column B | Z3 Column A | Z3 Column B | Hydrogen Bonds | Water Contacts | Hydrophobic Contacts |
|---|---|---|---|---|---|---|---|---|---|
| AAC | Q | D/E/H/K/N/R/S/T/Y | Q | D/E/H/K/N/R/S/T/Y | R | D/E/H/K/N/Q/Y | 6 | 0 | 0 |
| AAG | Q | E/K/R | N/Q | D/E/H/K/R | R | D/E/H/K/N/Q/S/T/Y | 6 | 0 | 0 |
| AAT | Q | E/K/R | N | D/E/H/K/N/Q/R | Q | D/E/H/K/N/Q/R/Y | 6 | 0 | 0 |
| ACC | Q | E/K | E/Q | D/K/N/S/T | R | E/K/N/Q/S/T | 6 | 0 | 0 |
| ACT | Q | E/K/R | D/N | E/K/N/Q/S/T | Q | D/E/H/K/N/Q/R/Y | 6 | 0 | 0 |
| GAA | R | H/K/Q/Y | N | D/E/H/K/Q/R/Y | Q | E/H/K/Q/R/Y | 6 | 0 | 0 |
| GAC | R | H/K/Y | N | D/E/H/K/Q/R/Y | E/Q | H/K/N/Q/R/S/T/Y | 6 | 0 | 0 |
| GAG | R | H/K/Q/Y | N | D/E/H/K/Q/R/Y | R | D/E/K/N/Q/S/T | 6 | 0 | 0 |
| GAT | R | H/K/Q/Y | N/Q | D/E/H/K/R/Y | Q | D/E/H/I/K/N/Q/R/Y | 6 | 0 | 0 |
| GCC | R | H/K/N/Q/S/T/Y | E/Q | D/H/K/N/Q/R/S/T | R | D/E/H/K/N/Q/S/T/Y | 6 | 0 | 0 |
| GCT | R | H/K/Q/Y | D/N | E/H/K/N/Q/R/S/T/Y | Q | D/E/H/K/N/Q/R/S/T/Y | 6 | 0 | 0 |
| ACA | Q | D/E/K/N/R | D | E/K/N/Q/S/T | o | D/E/H/I/K/L/N/Q/R/S/T/V/Y | 5 | 1 | 0 |
| ACG | Q | D/E/K/N/R | D/E | H/K/N/Q/R/S/T/Y | R | D/E/H/K/N/Q/S/T/Y | 5 | 1 | 0 |
| AGA | Q | E/K/R | N | H/K/Q/R/Y | Q | A/E/H/I/K/L/N/Q/R/V/Y | 5 | 1 | 0 |
| AGG | Q | E/K/R | N/Q | H/K/R | R | D/E/K/N/Q/Y | 5 | 1 | 0 |
| CAA | E | D/K/N/Q/R/S/T/Y | N | DfE/H/K/Q/R/S/T/Y | Q | E/H/K/Q/R/Y | 5 | 1 | 0 |
| CAG | E | D/K/N/Q/R | Q | D/E/H/K/N/Q/R | R | D/E/H/K/N/Q/S/T/Y | 5 | 1 | 0 |
| CAT | E | D/K/N/Q/R/S/T/Y | N/Q | D/E/H/K/N/Q/R/S/T/Y | N/Q | D/E/H/K/Q/R/Y | 5 | 1 | 0 |
| CCC | E | D/K/N/Q/R | E/Q | D/E/H/K/N/S/T/Y | R | E/H/KfN/Q/S/T/Y | 5 | 1 | 0 |
| CCT | E | K/Q/R | D/N | E/H/K/N/Q/S/T | Q | E/H/K/N/Q/R/S/T/Y | 5 | 1 | 0 |
| GCA | R | H/K/N/Q/S/T/Y | D | E/H/K/N/Q/R/S/T/Y | Q | A/E/H/I/K/L/N/Q/R/S/T/V/Y | 5 | 1 | 0 |
| GCG | R | H/K/N/Q/S/T/Y | D/E | H/K/N/Q/S/T | R | D/E/H/K/N/Q/S/T/Y | 5 | 1 | 0 |
| GGA | R | H/K/N/Q/Y | N | H/K/Q/R/S/T/Y | Q | A/D/E/H/I/K/L/N/Q/R/V/Y | 5 | 1 | 0 |
| AAA | K/R |  | N | D/E/H/K/Q/R/Y | Q | D/E/H/I/K/L/N/Q/R/Y | 5 | 0 | 0 |
| AGC | Q | E/K/R | H | K/N/Q/R/S/T/Y | R | D/E/H/K/N/Q/Y | 5 | 0 | 0 |
| AGT | Q | E/K/R | H | K/N/Q/R/S/T | Q | D/E/H/I/K/L/N/Q/R/S/T/Y | 5 | 0 | 0 |
| GGC | R | H/K/N/Q/Y | H | K/N/Q/R/S/T/Y | R | D/E/H/K/N/Q/S/T/Y | 5 | 0 | 0 |
| GGG | R | H/K/N/Q/Y | H | K/N/Q/R/S/T/Y | R | D/E/H/K/N/Q/S/T/Y | 5 | 0 | 0 |
| GGT | R | H/K/N/Q/Y | H | K/N/Q/R/S/T | N/Q | D/E/K/N/Q/R/S/T | 5 | 0 | 0 |

TABLE 3-continued

| Codon | Z1 Column A | Z1 Column B | Z2 Column A | Z2 Column B | Z3 Column A | Z3 Column B | Hydrogen Bonds | Water Contacts | Hydrophobic Contacts |
|---|---|---|---|---|---|---|---|---|---|
| CAC | E | K/Q/R | N | D/E/K/Q/R | E | H/K/Q/R/Y | 4 | 2 | 0 |
| CCA | E | K/Q/R | D | E/K/N/Q/S/T | Q | A/E/H/I/K/L/N/Q/R/S/T/V/Y | 4 | 2 | 0 |
| CCG | E | D/K/N/Q/R | D | E/H/K/N/Q/R/S/T/Y | R | D/E/H/K/N/Q | 4 | 2 | 0 |
| CGA | E | D/K/N/Q/R | N | H/K/Q/R/S/T/Y | Q | A/D/E/H/I/K/L/N/Q/R/S/T/V/Y | 4 | 2 | 0 |
| CGC | E | D/K/N/Q/R/S/T/Y | H | K/N/Q/R/S/T/Y | R | D/E/H/K/N/Q/Y | 4 | 1 | 0 |
| CGG | E | D/K/N/Q/R | H | K/N/Q/R/Y | R | D/E/H/K/N/Q/S/T/Y | 4 | 1 | 0 |
| CGT | E | D/K/Q/R | H | K/N/Q/R/Y | N/Q | D/E/H/K/N/Q/R/Y | 4 | 1 | 0 |
| ATA | Q | E/K/R | A/I/L/V | H/K/N/Q/R/S/T/Y | Q | E/H/I/K/L/O/R/V/Y | 4 | 0 | 1 |
| ATC | Q | D/E/K/N/R | I/L | D/E/H/K/N/Q/R/S/T/V/Y | E/R | H/K/N/Q/R/Y | 4 | 0 | 1 |
| ATG | Q | E/H/K/R | I/L/V | D/E/H/K/N/Q/R/S/T/Y | R | D/E/H/K/N/Q/Y | 4 | 0 | 1 |
| ATT | Q | E/K/R | I/L/V | H/K/N/Q/R/S/T/Y | Q | D/E/H/K/N/Q/R/S/T/Y | 4 | 0 | 1 |
| GTA | R | H/K/Q/Y | A/I/L/V | D/E/H/K/N/Q/R/S/T/Y | Q | A/D/E/H/I/K/L/N/Q/R/S/T/V/Y | 4 | 0 | 1 |
| GTC | R | H/K/Q/Y | I/L | H/K/N/Q/R/S/T/V | E/R | H/K/N/Q/S/T/Y | 4 | 0 | 1 |
| GTG | R | H/K/Q | E/L/V | H/K/N/Q/S/T | R | D/E/H/K/N/Q/S/T/Y | 4 | 0 | 1 |
| GTT | R | H/K/N/Q/Y | I/L/V | A/H/K/N/Q/R/S/T/Y | Q | D/E/H/I/K/L/N/Q/R/V/Y | 4 | 0 | 1 |
| TAA | I/L | K/O/R/V | N | D/E/H/K/Q/R/Y | Q | A/E/H/I/K/L/Q/R/V/Y | 4 | 0 | 1 |
| TAG | I/L | K/Q/R | N | D/E/K/Q/R | R | D/E/H/K/N/O/Y | 4 | 0 | 1 |
| TAT | E/L/V | K/N/Q/R/Y | N | D/E/H/K/N/Q/R/S/T/Y | Q | D/E/H/I/K/L/N/O/R/S/T/V/Y | 4 | 0 | 1 |
| TCC | E/L | A/H/*K/N/Q/R/V | E/Q | D/H/K/N/Q/R/S/T/Y | R | E/H/K/N/Q/S/T/Y | 4 | 0 | 1 |
| TCT | I/L | H(K/Q/R | D/N | E/H/K/N/Q/R/S/T/Y | N/Q | D/E/H/K/Q/R/Y | 4 | 0 | 1 |
| CTA | E | Q | A/I/L/V | H/K/N/Q/S/T | Q | A/E/I/K/L/N/Q/R/S/T/V | 3 | 1 | 1 |
| CTC | E | D/K/N/Q/R | I/L | H/K/N/Q/R/S/T/V/Y | E/R | D/H/*K/N/Q/Y | 3 | 1 | 1 |
| CTG | E | D/K/N/Q/R | I/L/V | K/N/Q/S/T | R | D/E/K/N/Q/Y | 3 | 1 | 1 |
| CTT | E | D/K/N/Q/R | I/L | D/E/H/K/N/Q/R/S/T/V/Y | Q | D/E/H/K/N/Q/R/Y | 3 | 1 | 1 |
| TCA | I/L | K/Q/R | D | E/H/K/N/Q/R/S/T/Y | Q | A/E/H/I/K/L/N/Q/R/S/T/V/Y | 3 | 1 | 1 |
| TCG | E/L | K/O/R | D | E/H/K/N/Q/R/S/T/Y | R | D/E/H/K/N/Q/S/T/Y | 3 | 1 | 1 |
| TGA | E/L | K(Q/R | N | H/K/Q/R/S/T/Y | Q | D/E/H/K/N1O/R/Y | 3 | 1 | 1 |
| TAC | I/L/V | K/Q/R | N | D/E/H/K/Q/R/Y | E | H/K/N/Q/R/Y | 3 | 0 | 1 |
| TGC | E/L/V | H/K/N/Q/R/S/T | H | K/N/Q/R/S/T/Y | R | D/E/H/K/N/O/Y | 3 | 0 | 1 |
| TGG | I/L | K/Q/R | H | K/N/Q/R/Y | R | D/E/H/K/N/Q/S/T/Y | 3 | 0 | 1 |
| TGT | I | H/K/L/N/Q/R | H | K/N/Q/R/S/T/Y | Q | E/H/E/K/L/N/Q/R/Y | 3 | 0 | 1 |
| TTA | I/L | K/N/Q/R | A/I/L/V | D/E/H/K/N/O/R/S/T/Y | Q | A/E/H/I/K/L/N/R/S/T/V/Y | 2 | 0 | 2 |
| TTC | E/L/V | K/N/Q/R | I/L | A/H/K/N/Q/R/S/T/V/Y | E/R | D/H/K/N/Q/S/T/Y | 2 | 0 | 2 |
| TTG | I/L | K/Q/R/Y | I/L/V | H/K/N/Q/S/T | R | D/E/H/K/N/Q/Y | 2 | 0 | 2 |
| TTT | I/L | K/N/Q/R/V | I/L/V | A/H/K/N/Q/R/S/T/Y | Q | D/E/H/K/N/Q/R/Y | 2 | 0 | 2 | where / separates alternative amino acids

The results of the molecular modeling analysis of various ZF a-helix complexes with the 64 different DNA triplets (Tables 1, 2 and 3), and the findings of spatial peculiarities in the three contact positions, are reflected in the ZF-DNA recognition rules. On the basis of the rules set forth in Tables 1, 2 and 3, DBP's with optimal binding affinity for any target DNA sequence can be designed. The "Column A" designations, i.e., the "A Rules," in Tables 1–3, show the amino acids with optimal binding for a given codon (triplet). The "Column B" designations, i.e., the "B rules," in Tables 1 and 3, show the amino acids with secondary, but still significant, binding affinity for a given triplet.

The column A rules range from the strongest triplet recognition with six H-bonds, zero water contracts and zero hydrophobic contacts with an evaluated energy of $(5 \times 6)+(2 \times 0)+(\times 0)=30$ to two hydrogen bonds, zero water contacts and two hydrophobic contacts with an evaluated energy of $(5 \times 2)+(2 \times 0)+(1 \times 2)=12$. The Column A rules ordinarily have a choice of just one or two amino acids in positions $Z_1$, $Z_2$ and $Z_3$. The column B rules, by comparison, have from three possible amino acids in each of the $Z_1$, $Z_2$ and $Z_3$ positions to as many as eighteen amino acids in different contacting arrangements in each of the $Z_1$, $Z_2$ and $Z_3$ positions. In the evaluation of the column B energies, there are a large number different groupings of three amino acids in positions $Z_1$, $Z_2$ and $Z_3$. The minimum energy is three hydrogen bonds, zero water contacts and zero hydrophobic contacts with an evaluated energy of $(5 \times 3)+(2 \times 0)+(1 \times 0)=15$. The maximum energy evaluation for these combinations is, on average, three hydrogen bonds and either two water contacts or two hydrophobic contacts, with an evaluated energy of from $(5 \times 3)+(2 \times 2)+(1 \times 0)=19$ down to $(5 \times 3)+(2 \times 0)+(1 \times 2)=17$. Thus, the column B rules have a narrower energy range (i.e., from 19 down to 15) than do the column A rules, which have an energy range from 30 down to 12. The narrow energy range for the column B rules means that the 64 different rules do not distinguish on the basis of energy as well as the 64 column A rules.

For example, as set forth in Table 2, a DBP which binds optimally to the DNA base triplet guanine-cytosine-cytosine (GCC) is one wherein the portion of the protein responsible for the binding to the triplet is a ZF domain within which is contained a segment having the sequence $Z_3XXZ_2LXZ_1H$ (SEQ ID NO: 2), wherein $Z_1$ is an arginine which interacts with position 1 of the DNA triplet; $Z_2$ is a glutamine or a glutamic acid which interacts with position 2 of the DNA triplet; $Z_3$ is an arginine which interacts with position 3 of the DNA triplet; X is an arbitrary amino acid; L is leucine and H is histidine.

As set forth in Table 1 or 3 (see the "column B" entries for the $Z_1$, $Z_2$, and $Z_3$ positions for a given codon), a DBP which effectively, if not optimally, binds to the DNA base triplet guanine-cytosine-cytosine (GCC) is one wherein the portion of the protein responsible for the binding to the triplet is a ZF domain within which is contained a segment having the sequence $Z_3XXZ_2LXZ_1H$ (SEQ ID NO: 2), wherein $Z_1$ is an amino acid selected from the group consisting of histidine, lysine, glutamine, asparagine, tyrosine, serine and threonine which interacts with position 1 of the DNA triplet; $Z_2$ is an amino acid selected from the group consisting of glutamine, asparagine, aspartic acid, serine, threonine, arginine, histidine, and lysine which interacts with position 2 of the DNA triplet; $Z_3$ is an amino acid selected from the group consisting of glutamine, asparagine, glutamic acid, aspartic acid, histidine, lysine, tyrosine, serine and threonine which interacts with position 3 of the DNA triplet; X is an arbitrary amino acid; L is leucine and H is histidine.

It will be appreciated, of course, that DBP's of intermediate affinity, i.e., ones wherein the $Z_1$, $Z_2$ and $Z_3$ contact amino acids are selected according to a combination of the "A" and "B Rules," can be designed. For example, in the segment $Z_3XXZ_2LXZ_1H$ (SEQ ID NO: 2) within a ZF domain for binding to the triplet GCC, $Z_1$ could be an arginine; $Z_2$ could be a glutamnine or a glutamic acid; and $Z_3$ could be selected from the group consisting of glutamine, asparagine, glutamic acid, aspartic acid, histidine, lysine, tyrosine, serine and threonine.

The basic building block for such proteins is denoted by the formula:

$$NH_2—ZiF_c—COOH,$$

where $ZiF_c$ is a ZF domain of the form

Y/FXCX$_{2-4}$ CG/D K/RXFXZ$_3$XXZ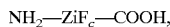HSEQ ID NO: 1), where $Z_1$, $Z_2$ and $Z_3$ are amino acids chosen from Table 1, 2 or 3 to correspond to the three bases of the DNA triplet, and the remaining components of the formula are as described earlier in the description of Formula I.

In the preferred embodiment of the invention, a zinc-finger domain for binding to a given DNA triplet is designed by selection of the appropriate AA's in Table 2 or in column A of Table 1 or Table 3. In another embodiment of the invention, the ZF domain is designed by selection from among the AA's set forth for a given DNA triplet in column B of Table 1 or 3.

One such domain is required for each triplet of the target sequence; for a target string of only 3 bases, the above formula defines the protein.

If the target string of DNA is 6 bases, the DBP design is extended as follows:

$$NH_2—ZiF_1—\{linker\}—ZiF_2—COOH$$

where $ZiF_1$ and $ZiF_2$ are ZF domains designed, as shown above for ZiFC, to bind to the first and second triplets of the six bases, and (linker) is an amino acid sequence conforming to the pattern T/S G/E X$_{0-2}$E K/R P    (sites 21–26 of SEQ ID NO: 1), again wherein the components are as defined previously in Formula I.

If 1) the target string of DNA contains 9, 12, or a higher multiple of 3 bases; 2) it is required to design a DBP for 3n+3 bases; and 3) the DBP for the first 3n bases is given by the sequence:

$$NH_2—ZiF_1—\{linker\}—ZiF_2—\{linker\}—\ldots—\{linker\}—ZiFn—COOH$$

then the DBP design is extended recursively and the required DBP is specified by the sequence:

$$NH_2—ZiF_1—\{linker\}—ZiF_2—\{linker\}—\ldots$$
$$\ldots—\{linker\}—ZiF_n—\{linker\}—ZiF_{n+1}——COOH$$

where $ZiF_{n+1}$ is a ZF domain designed, as shown above for ZiFC, to bind with the $n^{th}+1$ triplet of the target sequence of base pairs.

Figure 3:
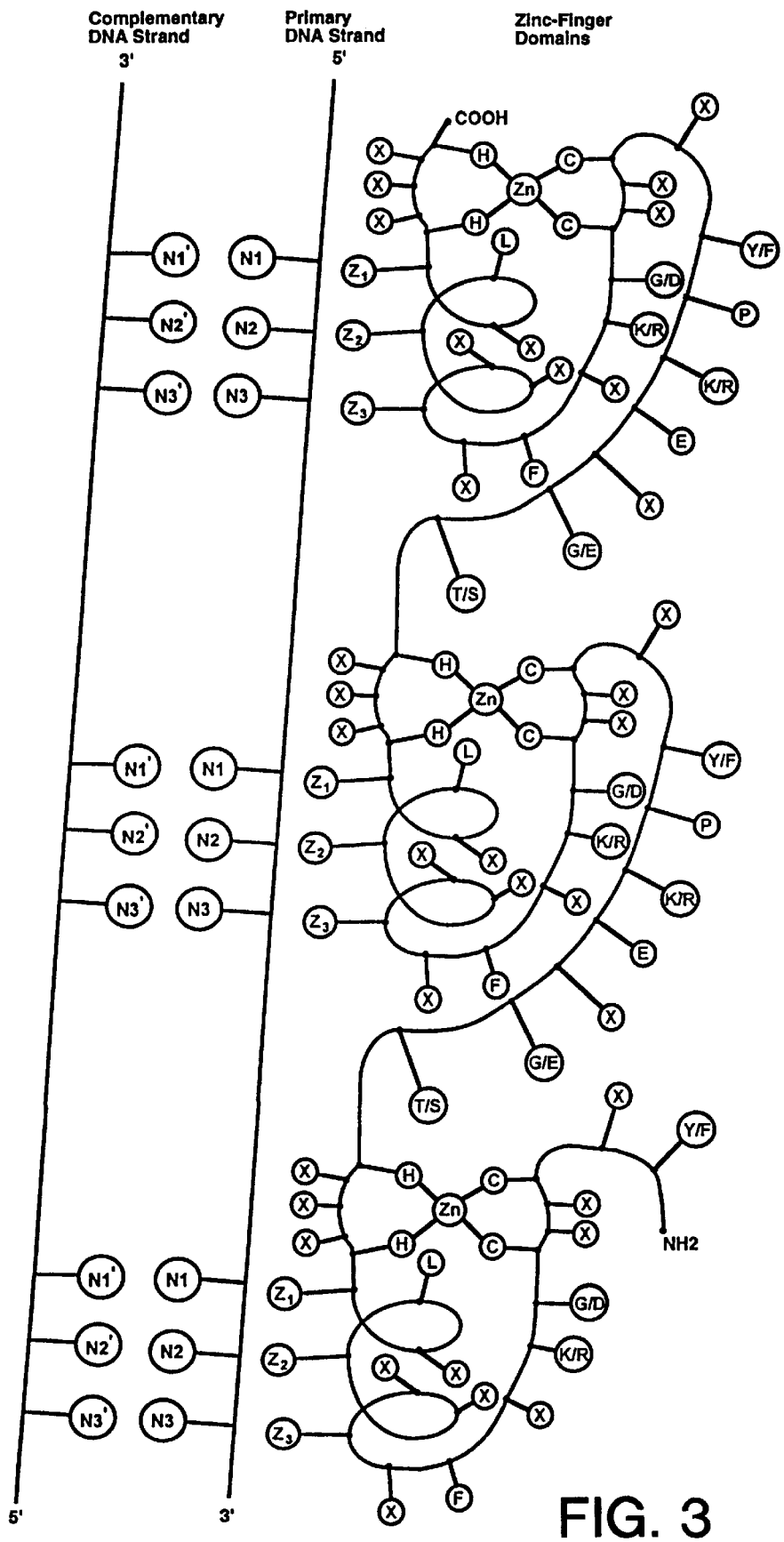
FIG. 3 is a schematic representation of the interaction between a target DNA string of 9 bases and a three-domain DBP.

FIG. 3 provides a schematic representation of a ZF protein wherein n=3, i.e., one which has 3 ZF domains (i.e., n=3) connected by linker sequences and is designed to bind to a target DNA string of 9 (3n) bases.

The above rules enable ready determination of the optimal amino acid(s) for binding to any given DNA triplet and thus the identification and positioning of the 3 amino acids in a ZF domain which would be the ideal component of a DBP for binding to the DNA triplet.

The application of the rules can then be extended to design of a DBP containing a set number, $n_d$, of ZF domains, which DPB binds to a target stretch of $3n_d$ nucleotides within a given DNA sequence. The target $3n_d$ stretch of nucleotides, and the collection and order of $n_d$ domains in the DBP, are such that the binding energy for the DPB and target DNA sequence is the highest possible for any pairing of a DBP containing the set number, $n_d$, of ZF domains with any stretch of $3n_d$ nucleotides within the entire DNA molecule being screened.

Accordingly, the embodiment of the invention of primary importance is a method for designing such a DBP for a DNA sequence of any length. The method employs the rules disclosed above in combination with a means of screening and ranking all possible segments of $3n_d$ nucleotides within the sequence by their affinities for DBP's containing $n_d$ ZF domains to determine a unique DBP with the desired properties.

More particularly, the invention is directed to a method for designing a DBP, with multiple ZF domains connected by linker sequences, that binds selectively to a target DNA sequence within a given gene, each of said ZF domains having the formula $A_1XCX_{2-4}CA_2A_3XFXZ_3XXZ_2LXZ_1HX_{3-5}H$    (SEQ ID NO: 3)

and each of said linkers having the formula $A_4A_5X_{0-2}EA_6P$    (SEQ ID NO: 4), wherein (i) X is any amino acid; (ii) $X_{2-4}$ is a peptide from 2 to 4 amino acids in length; (iii) $X_{3-5}$ is a peptide from 3 to 5 amino acids in length; (iv) $X_{0-2}$ is a peptide from 0 to 2 amino acids in length; (iv) $A_1$ is selected from the group consisting of phenylalanine and tyrosine; (v) $A_2$ is selected from the group consisting of glycine and aspartic acid; (vi) $A_3$ is selected from the group consisting of lysine and arginine; (vii) $A_4$ is selected from the group consisting of threonine and serine; (viii) $A_5$ is selected from the group consisting glycine and glutamic acid; (ix) $A_6$ is selected from the group consisting of lysine and arginine; (x) C is cysteine; (xi) F is phenylalanine; (xii) L is leucine; (xiii) H is histidine; (xiv) E is glutamic acid; (xv) P is proline; and (xvi) $Z_1$, $Z_2$ and $Z_3$ are the base-contacting amino acids, comprising the steps of:

(a) setting a genome to be screened;
(b) selecting the target DNA sequence in the genome for binding;
(c) setting the number of zinc-finger domains to $n_d$;
(d) dividing the target DNA sequence into nucleotide blocks wherein each block contains $n_z$ nucleotides using a first routine where $n_z$ is determined using the following relationship:

$n_z=3n_d$;

(e) assigning base-contacting amino acids at $Z_1$, $Z_2$ and $Z_3$ to each ZF domain, according to the A Rules and/or B Rules set forth in Tables 1–3, of a DBP which binds to the first nucleotide block from step (d) as numbered from the first 5' nucleotide of the target gene sequence to generate a block-specific DBP and calculating the binding energy, Binding Energy block, of each ZF domain of each such block-specific DBP as the product of the binding energies, Binding Energy$_{domain}$, of all zinc-finger domains of the polypeptide, each determined using the formula:

Binding Energy$_{domain}$=(5×the number of hydrogen bonds)+(2×the number of H$_2$O contacts)+(the number of hydrophobic contacts);

(f) subdividing the DBP from step (d) into blocks using a second routine to generate a subdivided DBP having three ZF domains;

(g) screening the subdivided DBP from step (f) against the genome using a third routine to determine the number of binding sites in the genome for each subdivided DBP in the genome and assigning a binding energy for each such site using the following formula:

Binding Energy$_{site\ n}$=(5×the number of hydrogen bonds)+(2×the number of H$_2$O contacts)+(the number of hydrophobic contacts);

(h) calculating a ratio of binding energy, $R_b$, using a fourth routine for each nucleotide-block-specific DBP from step (e) using the following formula:

$R_b$=Binding Energy$_{block}$/the sum of all Binding Energy$_{site\ n}$'s for all subdivided DBP's from step (g);

(i) repeating steps (f) through (h) for each subdivided DBP wherein $n_d \geq 4$;

(j) repeating steps (d) through (i) for each nucleotide block in the target DNA sequence containing $n_z$ nucleotides;

(k) rank-ordering $R_b$ numerical values obtained from step (h); and (l) selecting a DBP with an acceptable $R_b$ value.

Preferred embodiments of this aspect of the invention are:

1) the design method as set forth above wherein the DBP $R_b$ numerical value is the highest numerical value for all DBP's in step (h) that bind to the target DNA sequence.

2) the method above wherein the DBP $R_b$ numerical value determined in step (h) is at least 10,000.

3) the method above wherein the number of ZF domains, $n_d$, is nine.

4) the method above wherein the rules for assigning base-contacting amino acids at $Z_1$, $Z_2$ and $Z_3$ for each nucleotide block in step (e) are selected from rule set A.

The invention is further directed to a computer system for designing a DBP, with multiple ZF domains connected by linker sequences, that binds selectively to a target DNA sequence within a given gene, each of said ZF domains having the formula

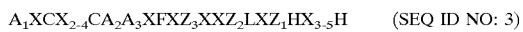  (SEQ ID NO: 3)

and each of said linkers having the formula

  (SEQ ID NO: 4), wherein (i) X is any amino acid; (ii) $X_{2-4}$ is a peptide from 2 to 4 amino acids in length; (iii) $X_{3-5}$ is a peptide from 3 to 5 amino acids in length; (iv) $X_{0-2}$ is a peptide from 0 to 2 amino acids in length; (iv) $A_1$ is selected from the group consisting of phenylalanine and tyrosine; (v) $A_2$ is selected from the group consisting of glycine and aspartic acid; (vi) $A_3$ is selected from the group consisting of lysine and arginine; (vii) $A_4$ is selected from the group consisting of threonine and serine; (viii) $A_5$ is selected from the group consisting glycine and glutamic acid; (ix) $A_6$ is selected from the group consisting of lysine and arginine, (x) C is cysteine; (xi) F is phenylalanine; (xii) L is leucine; (xiii) H is histidine; (xiv) E is glutamic acid; (xv) P is proline; and (xvi) $Z_1$, $Z_2$ and $Z_3$ are the base-contacting amino acids, comprising the steps of:

(a) setting a genome to be screened;

(b) selecting the target DNA sequence in the genome for binding;

(c) setting the number of ZF finger domains to $n_d$;

(d) dividing the target DNA sequence into nucleotide blocks wherein each block contains $n_z$ nucleotides using a first routine where $n_z$ is determined using the following relationship:

$n_z = 3n_d$;

(e) assigning base-contacting amino acids at $Z_1$, $Z_2$ and $Z_3$ to each ZF domain, according to the A Rules and/or B Rules set forth in Tables 1–3, of a DBP which binds to the first nucleotide block from step (d) as numbered from the first 5' nucleotide of the target gene sequence to generate a block-specific DBP and calculating the binding energy, Binding Energy$_{block}$, of each ZF domain of each such block-specific DBP as the product of the binding energies, Binding Energy$_{domain}$, of all domains of the DBP, each determined using the formula:

Binding Energy$_{domain}$=(5×the number of hydrogen bonds)+(2×the number of H$_2$O contacts)+(the number of hydrophobic contacts);

(f) subdividing the DBP from step (d) into blocks using a second routine to generate a subdivided DBP having three ZF domains;

(g) screening the subdivided DBP from step (f) against the genome using a third routine to determine the number of binding sites in the genome for each subdivided DBP in the genome and assigning a binding energy for each such site using the following formula:

Binding Energy$_{site\ n}$=(5×the number of hydrogen bonds)+(2×the number of H$_2$O contacts)+(the number of hydrophobic contacts);

(h) calculating a ratio of binding energy, $R_b$, using a fourth routine for each nucleotide block-specific DBP from step (e) using the following formula:

$R_b$=Binding Energy$_{block}$/the sum of all Binding Energy$_{site\ n}$'S for all subdivided DBP's from step (g);

(i) repeating steps (f) through (h) for each subdivided DBP wherein $n_d \geq 4$;

(j) repeating steps (d) through (i) for each nucleotide block in the target DNA sequence containing $n_z$ nucleotides;

(k) rank-ordering $R_b$ numerical values obtained from step (h);

(l) selecting a DBP with an acceptable $R_b$ value.

According to the instant invention, $R_b$, as defined in (h) above for both the design method and computer system, has a lower limit of 10,000. Preferably $R_b$ is greater than $10^6$.

Preferred embodiments of this aspect of the invention are:

1) the computer system as set forth above wherein the DBP $R_b$ numerical value is the highest numerical value for all DBP's in step (h) that bind to the target DNA sequence.
2) the computer system above wherein the DBP $R_b$ numerical value determined in step (h) is at least 10,000.
3) the computer system above wherein the number of ZF domains, $n_d$, is nine.
4) the computer system above wherein the rules for assigning base-contacting amino acids at $Z_1$, $Z_2$ and $Z_3$ for each nucleotide block in step (e) are selected from rule set A.

The method and computer system of the instant invention are further illustrated by the block flow diagrams of FIGS. 4–9.

Figure 4:
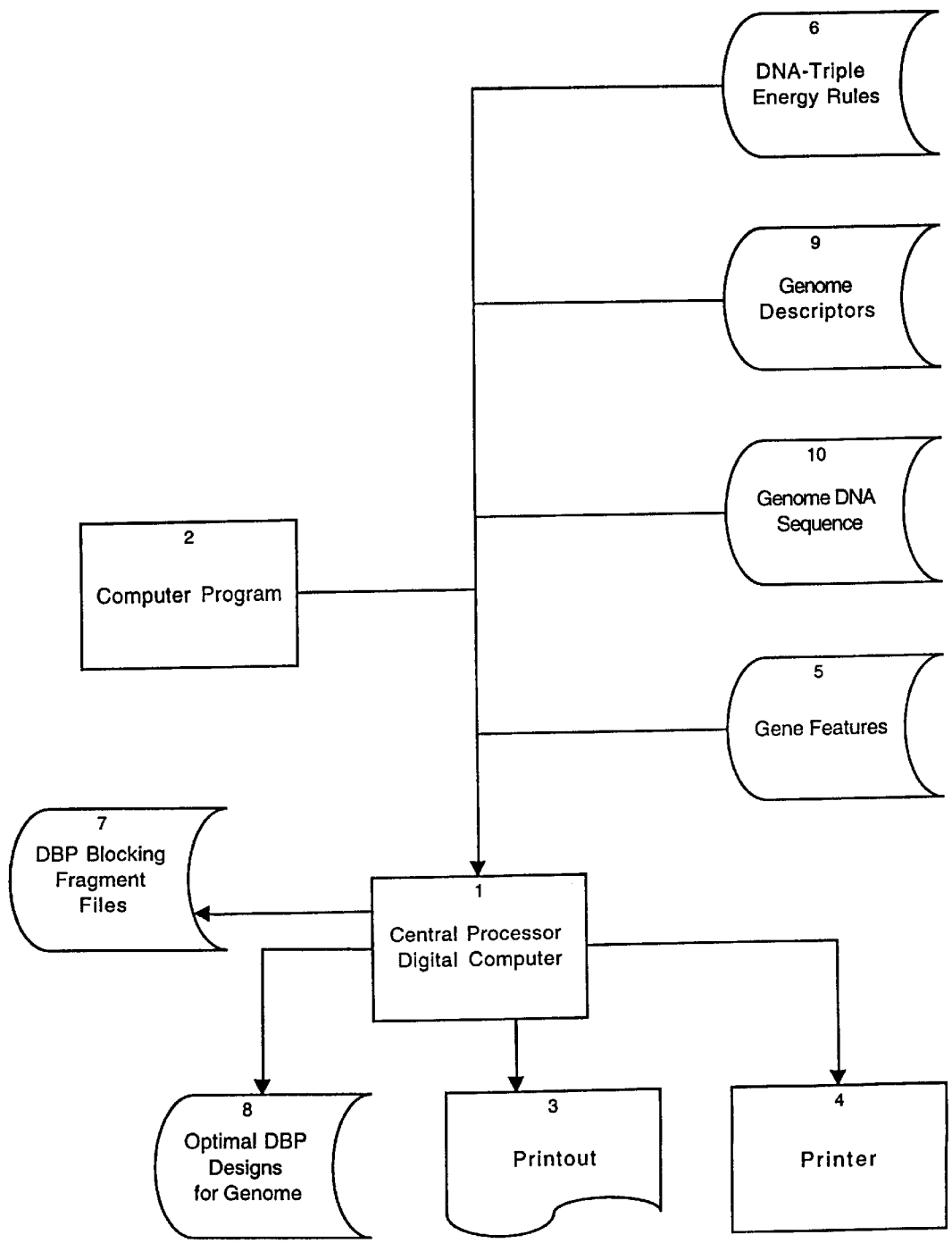
FIG. 4 is a block flow diagram of the computer system by which the instant DBP design process is implemented.

FIG. 4 shows the components of the computer system on which the DBP design process is implemented. A Central Processor Digital Computer (1) of any manufacture is provided with a Computer Program (2) written by the inventors. This Computer Program (2) reads a series of files described as DNA-Triple Energy Rules (6), Genome Descriptors (9), Genomic DNA Sequence (10) and Gene Features (5). The Central Processor (1) transforms this information into the DBP Blocking Fragment Files (7) and the Optimal DBP Designs for Genome (8).

Figure 5:
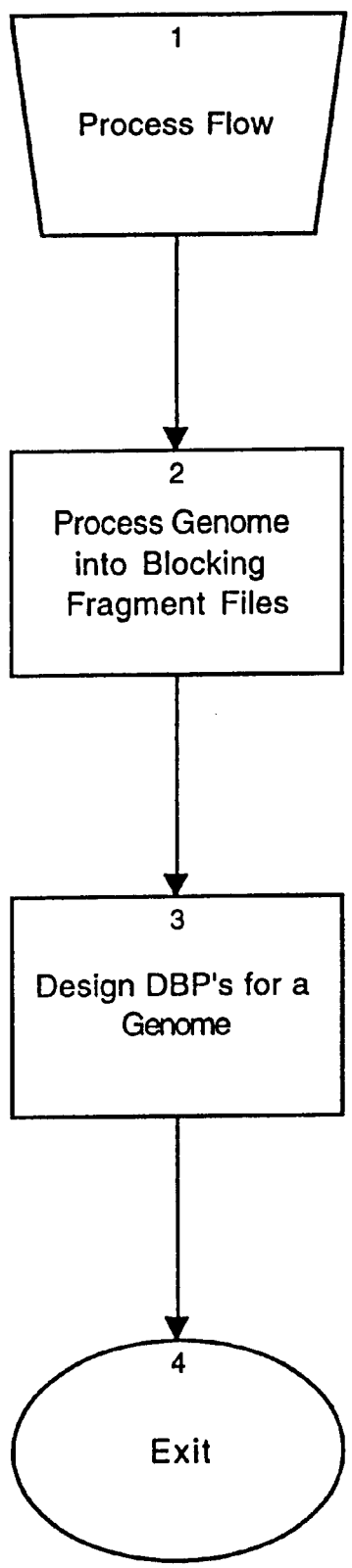
FIG. 5 is a block flow diagram wherein the Computer Program block (2) of FIG. 4 is further broken down.
Figure 6A:
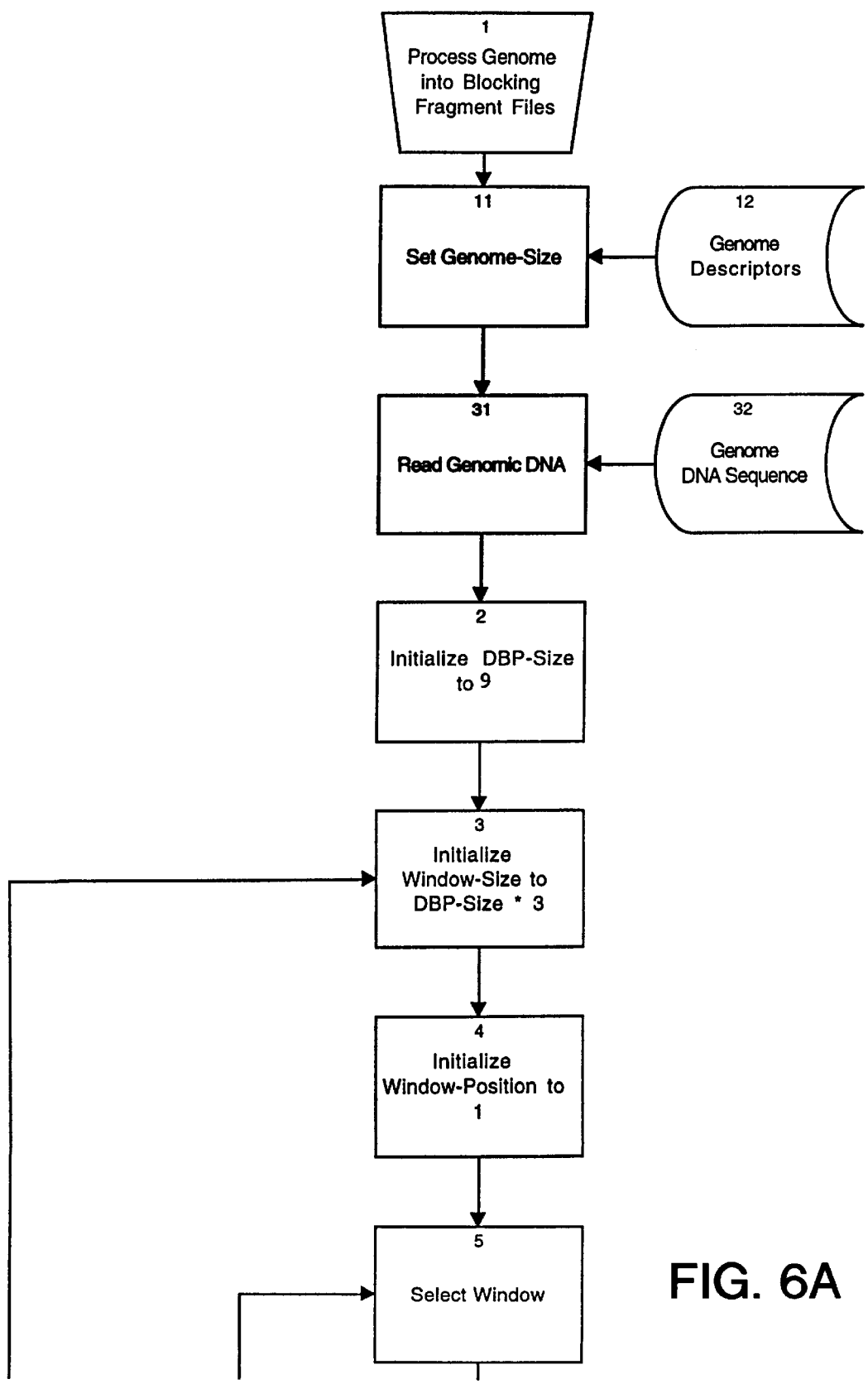
FIG. 6 is a block flow diagram wherein the Process Genome into Blocking Fragment Files block (2) of FIG. 5 is further broken down.
Figure 6B:
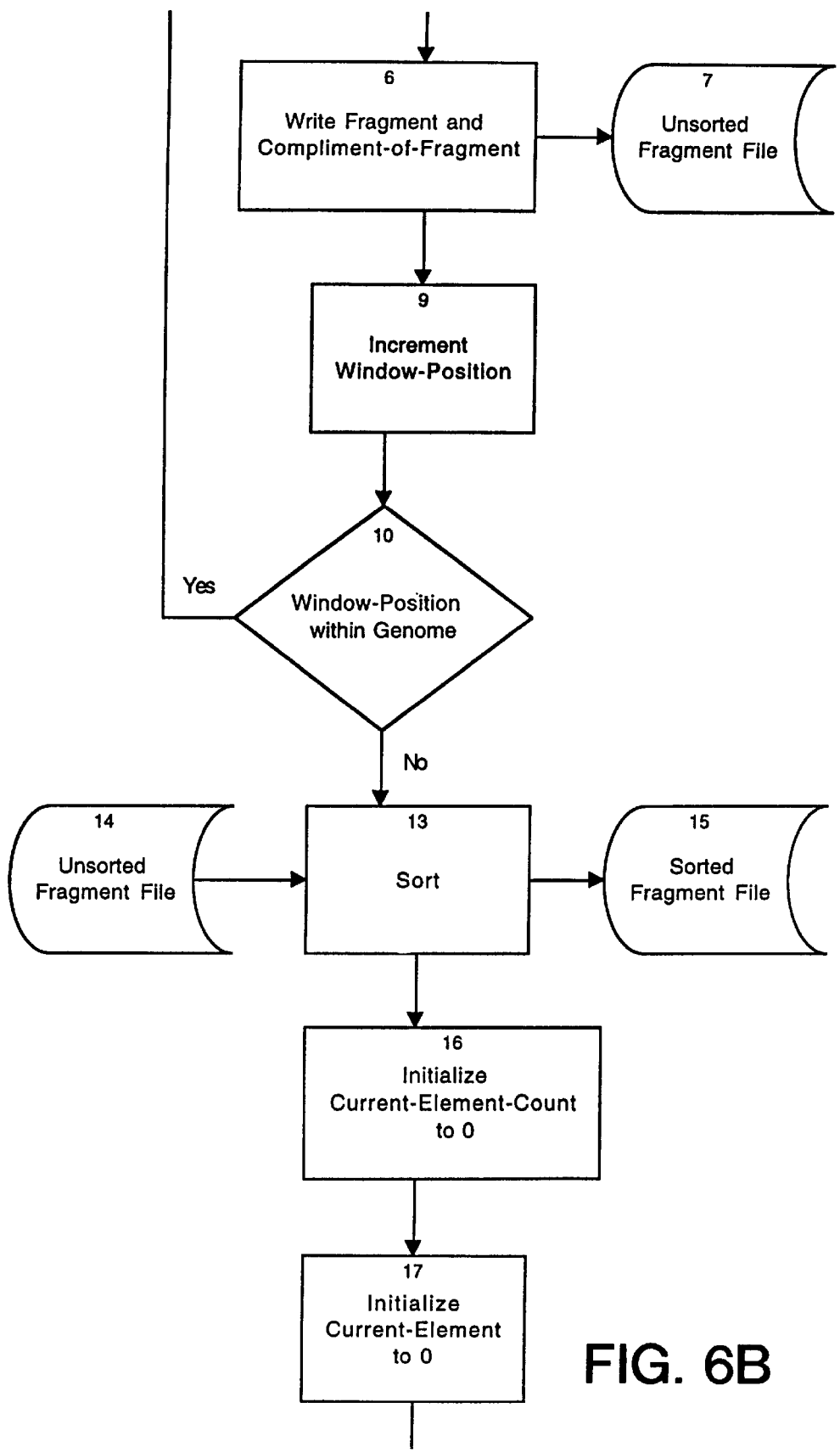
Figure 6C:
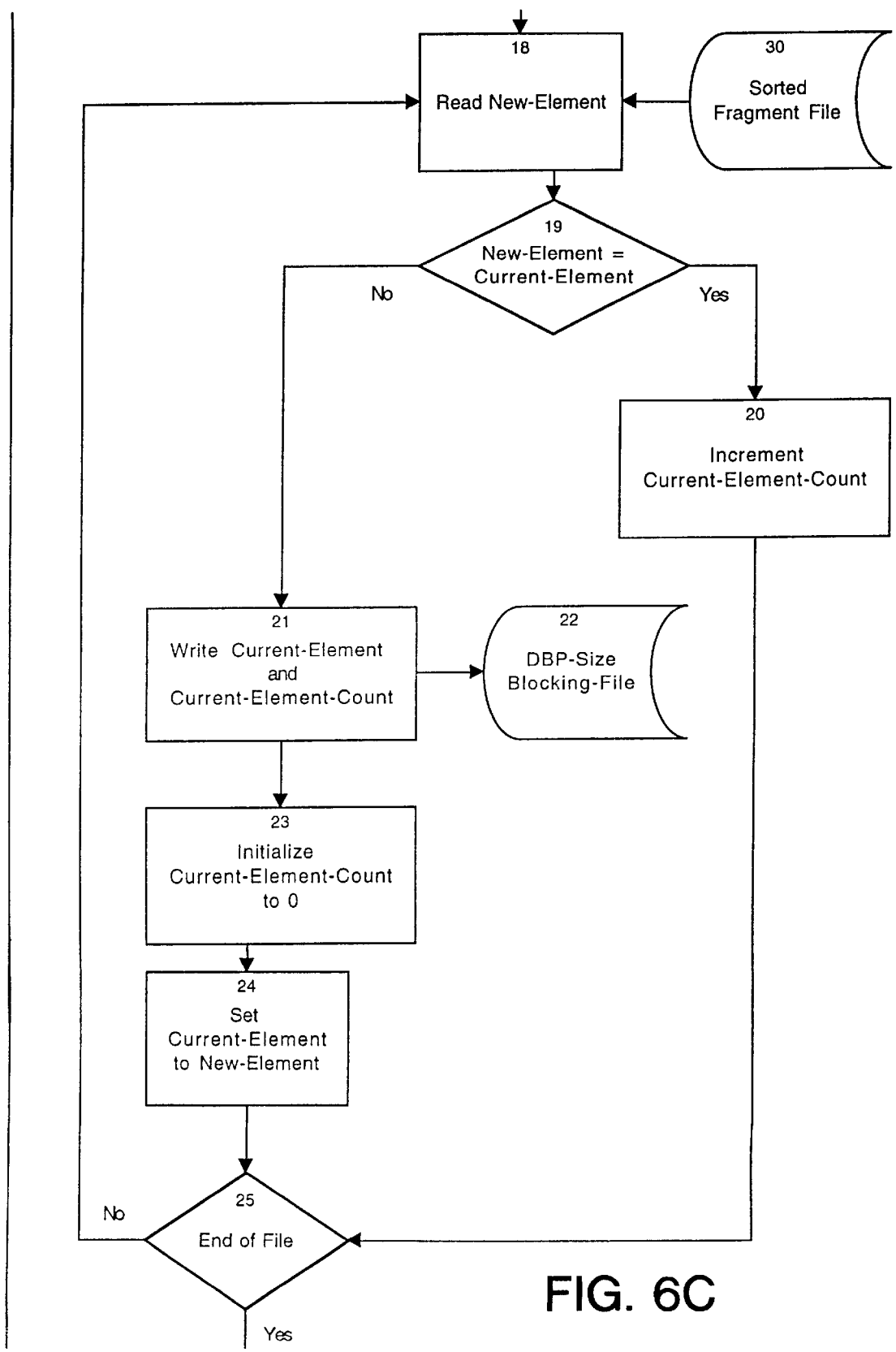
Figure 6D:
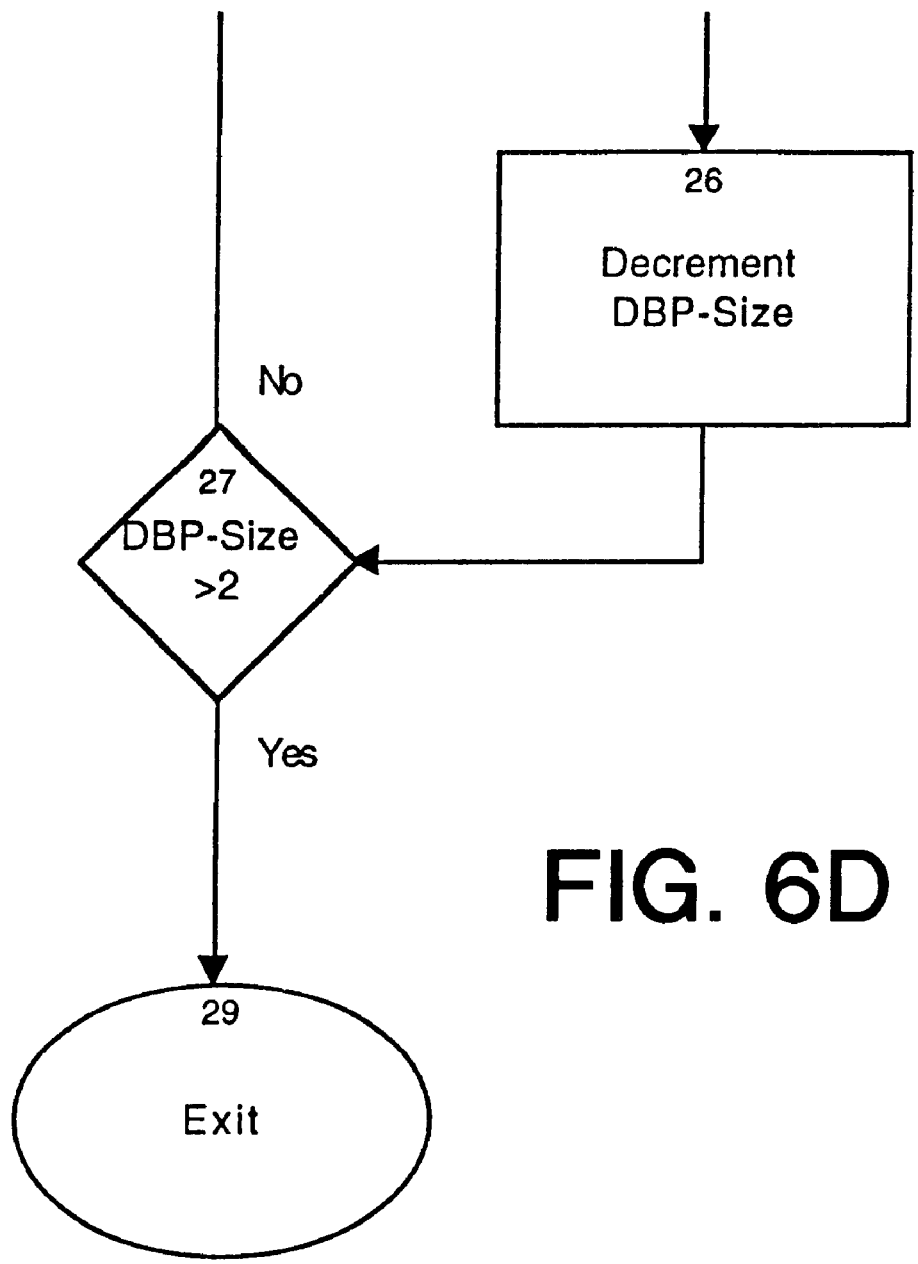
Figure 7A:
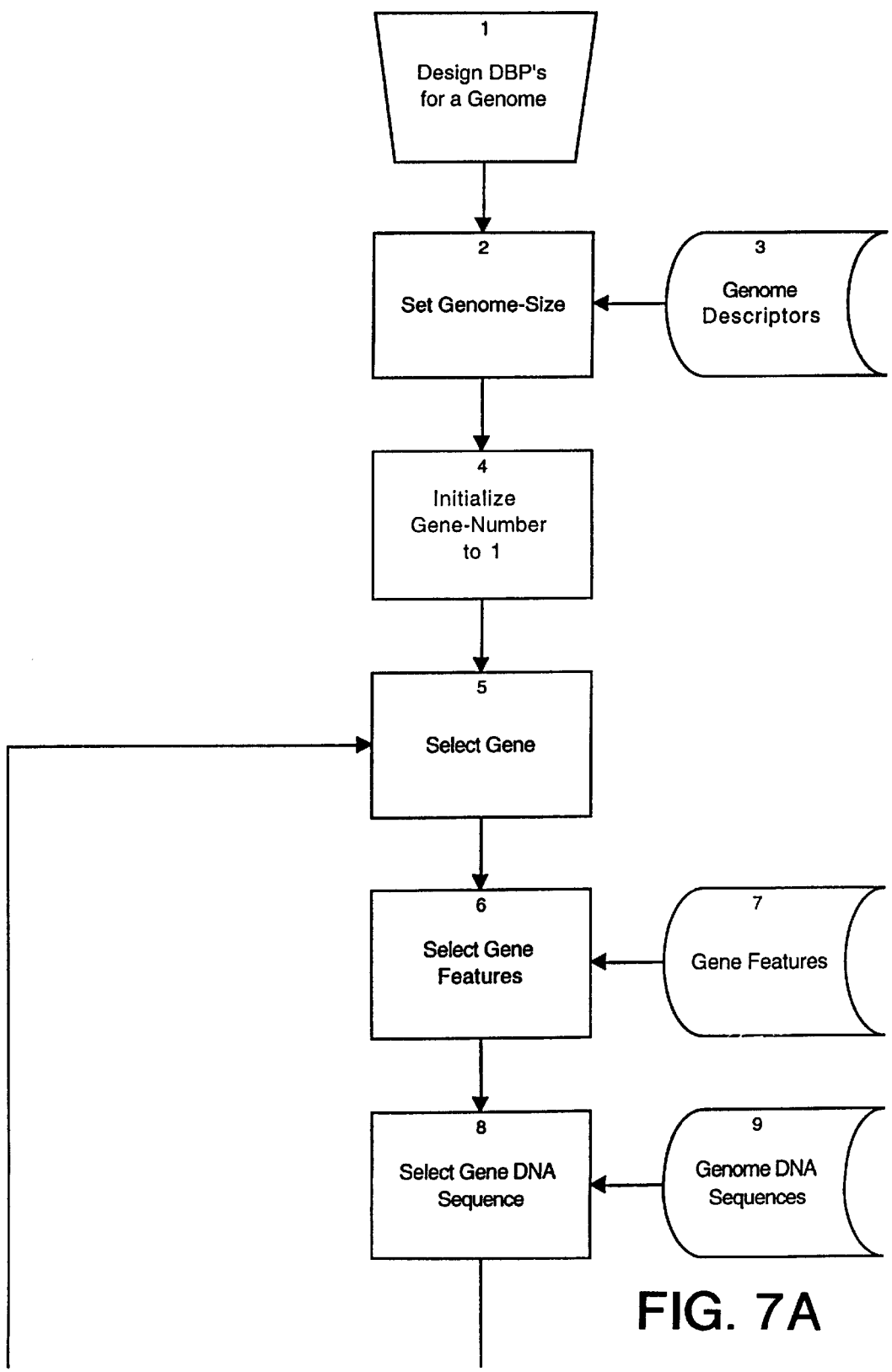
FIG. 7 is a block flow diagram wherein the Design DBP's for a Genome block (3) of FIG. 5 is further broken down.
Figure 7B:
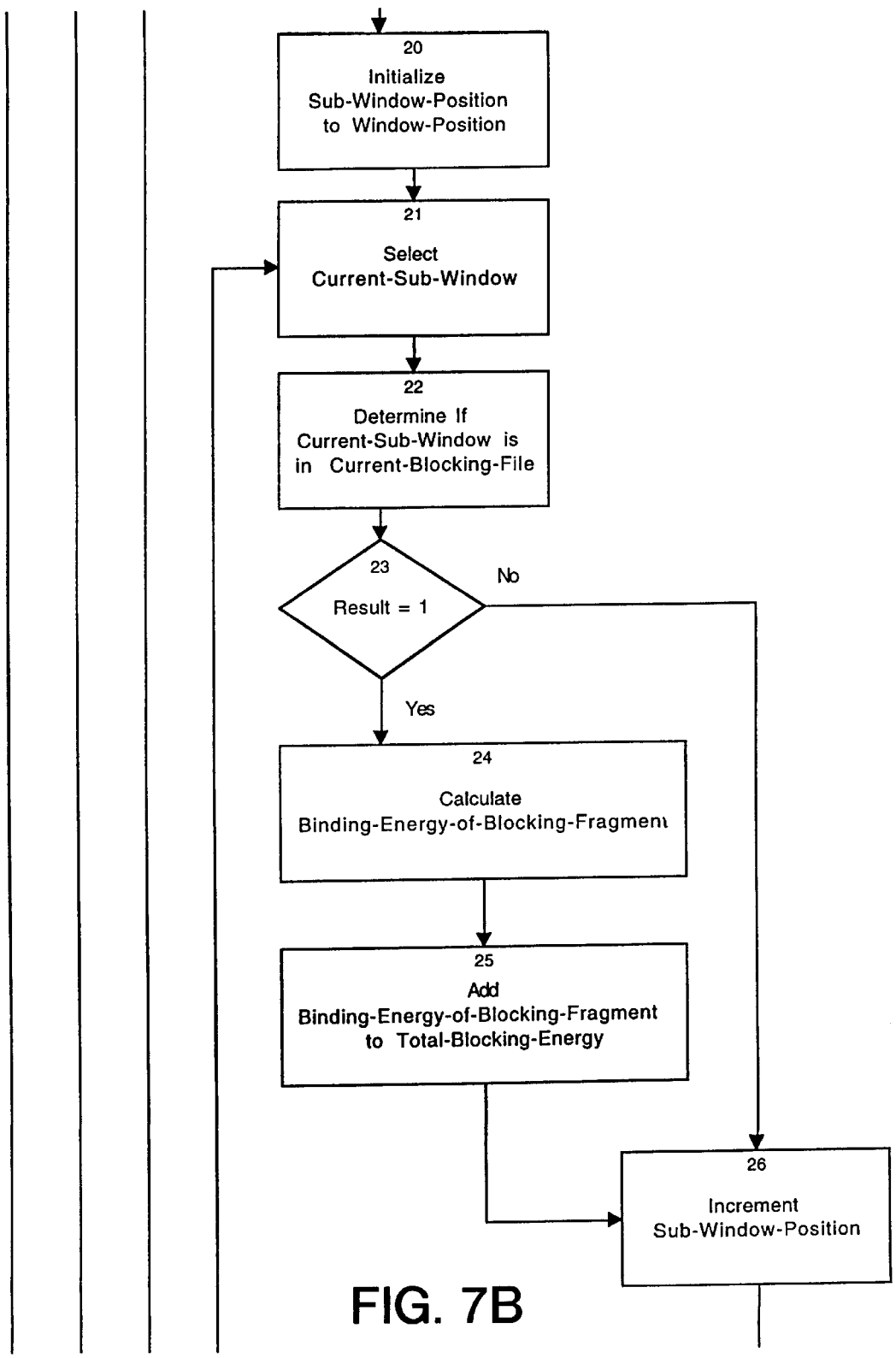
Figure 7C:
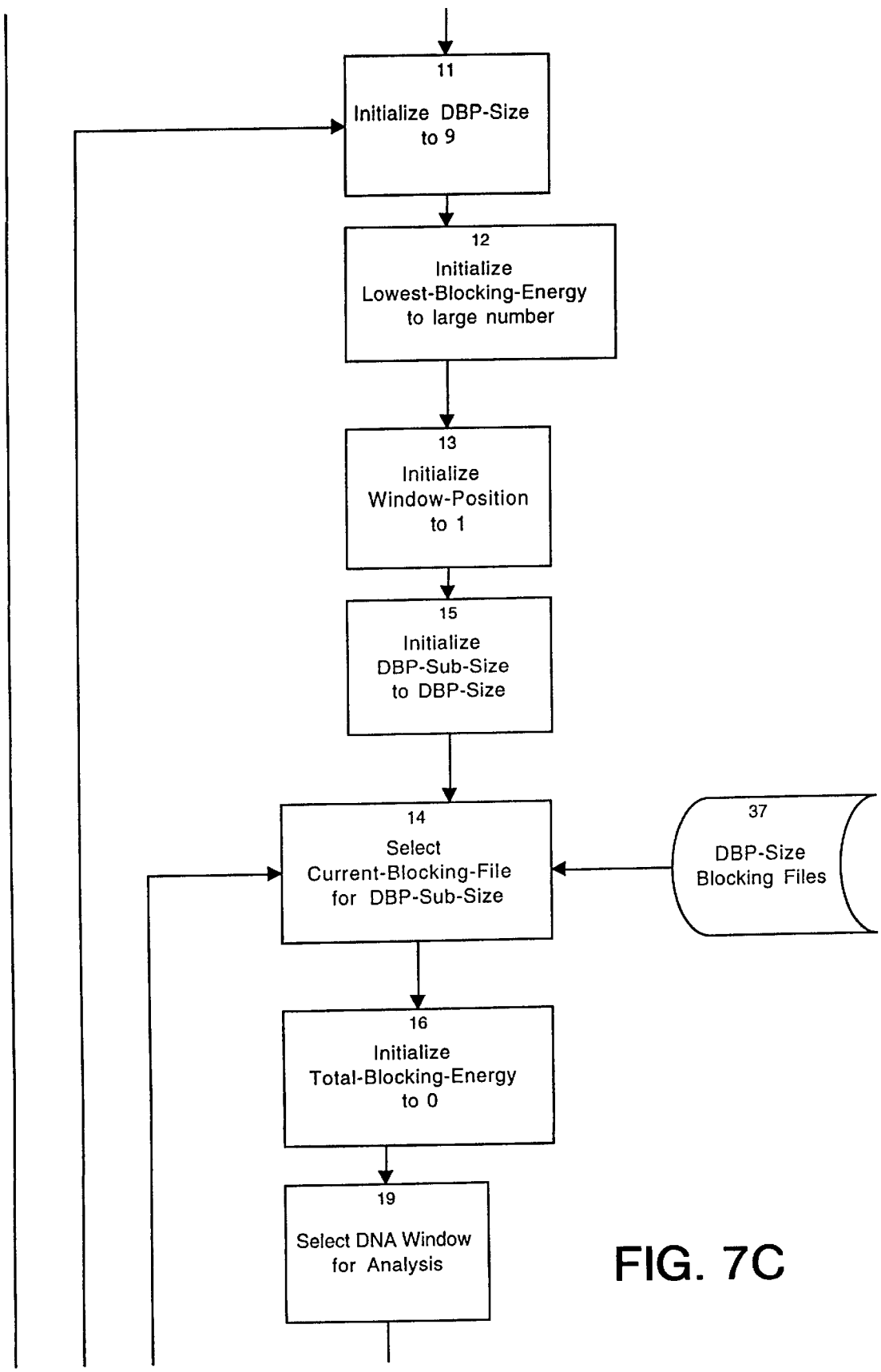
Figure 7D:
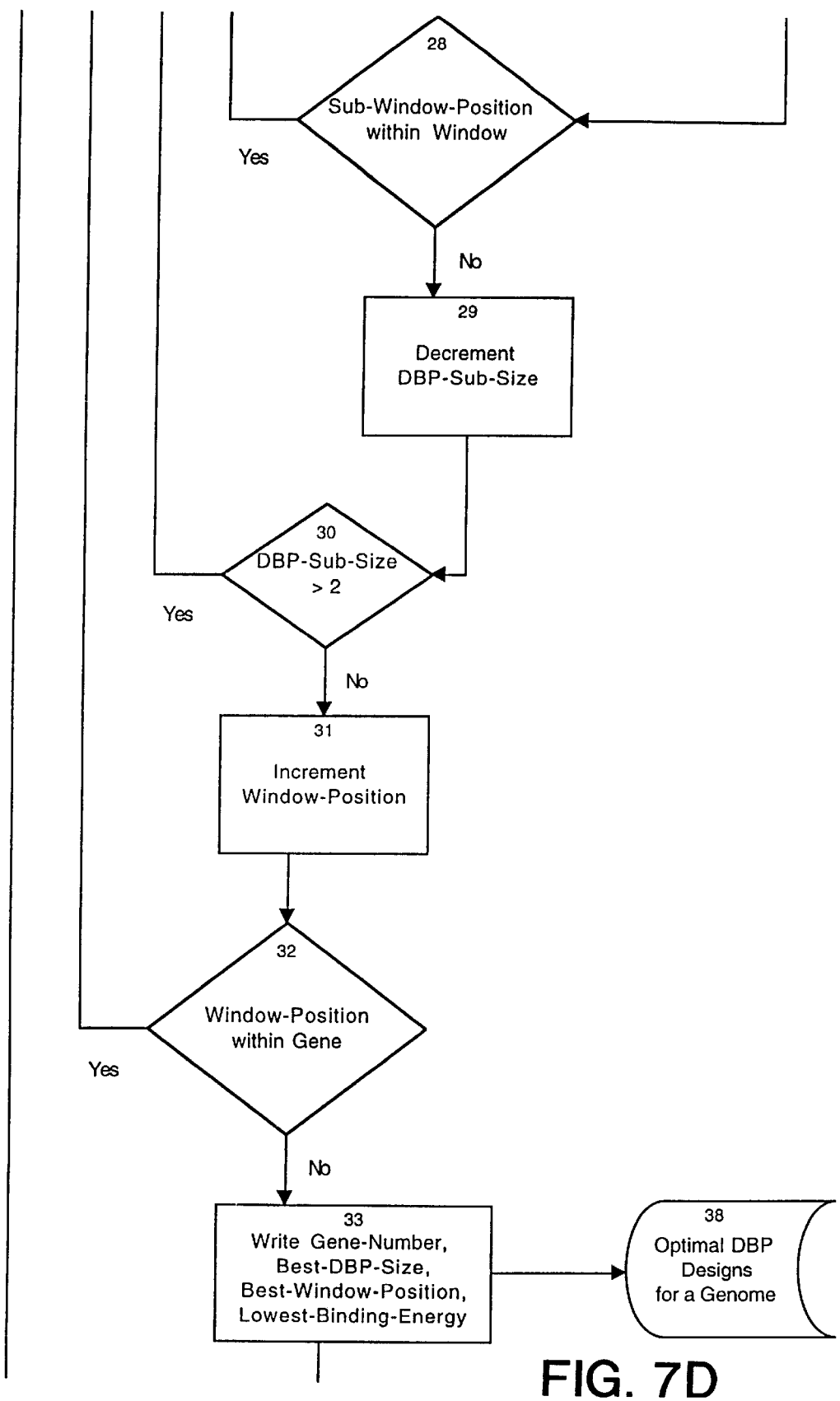
Figure 7E:
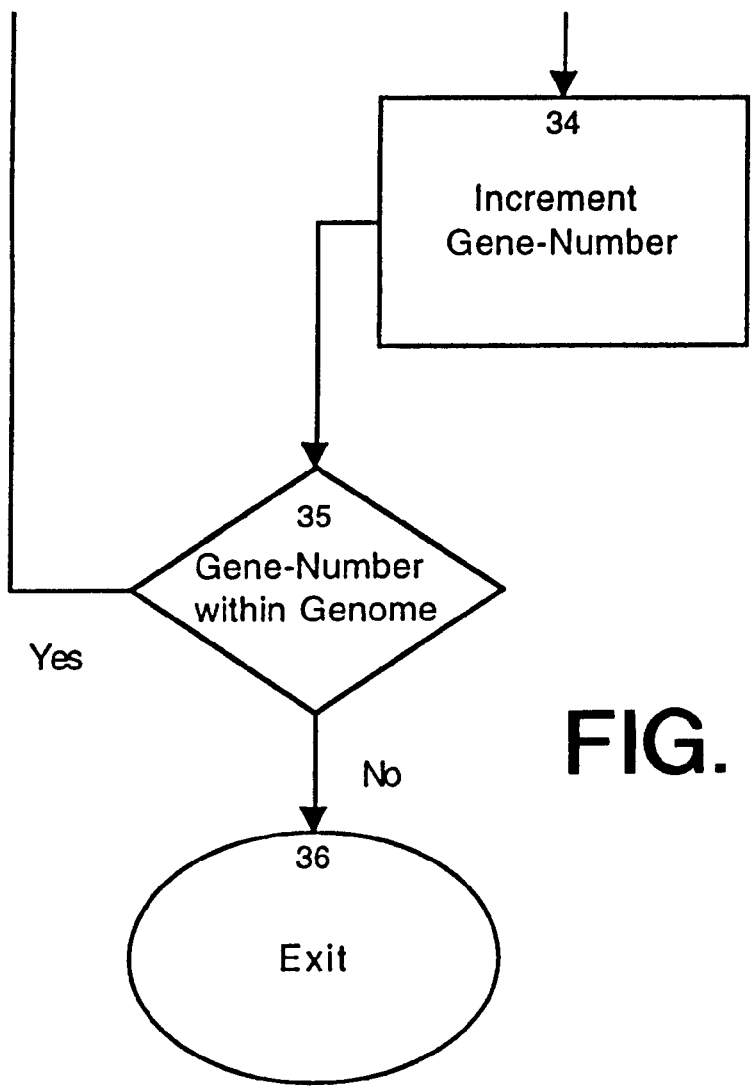

FIG. 5 shows that the Computer Program (2) in FIG. 4 has two portions. The genomic data is first transformed by the Process Genome into Blocking Fragment Files function (2). These files are then used by the Design DBP's for a Genome function (3).

The Process Genome into Blocking Fragment Files block (2) of FIG. 5 is represented in greater detail in FIG. 6. For every $n_d$ from 11 down to 3 the Genome Descriptors file (12) and the Genome DNA Sequence file (32) are read and transformed into the Unsorted Fragment File (7). This same Unsorted Fragment File (14) is transformed by the Sort function (13) provided by the computer manufacturer into the Sorted Fragment file (15). The same Sorted Fragment File (30) is read and transformed eventually into the DBP-Size Blocking File (22).

The Design DBP's for a Genome block (3) of FIG. 5 is represented in greater detail in FIG. 7. The Genome Descriptors file (3), the Gene Features file (7), the Genome DNA Sequence file (9) and the DBP-Size Blocking Files (37) corresponding to the $n_d$'s from 11 down to 3 are read and used to transform the genomic DNA first into genes and then into a file of the Optimal DBP Designs for a Genome (38). The transformation and design process is done for all the genes in a genome.

Figure 8:
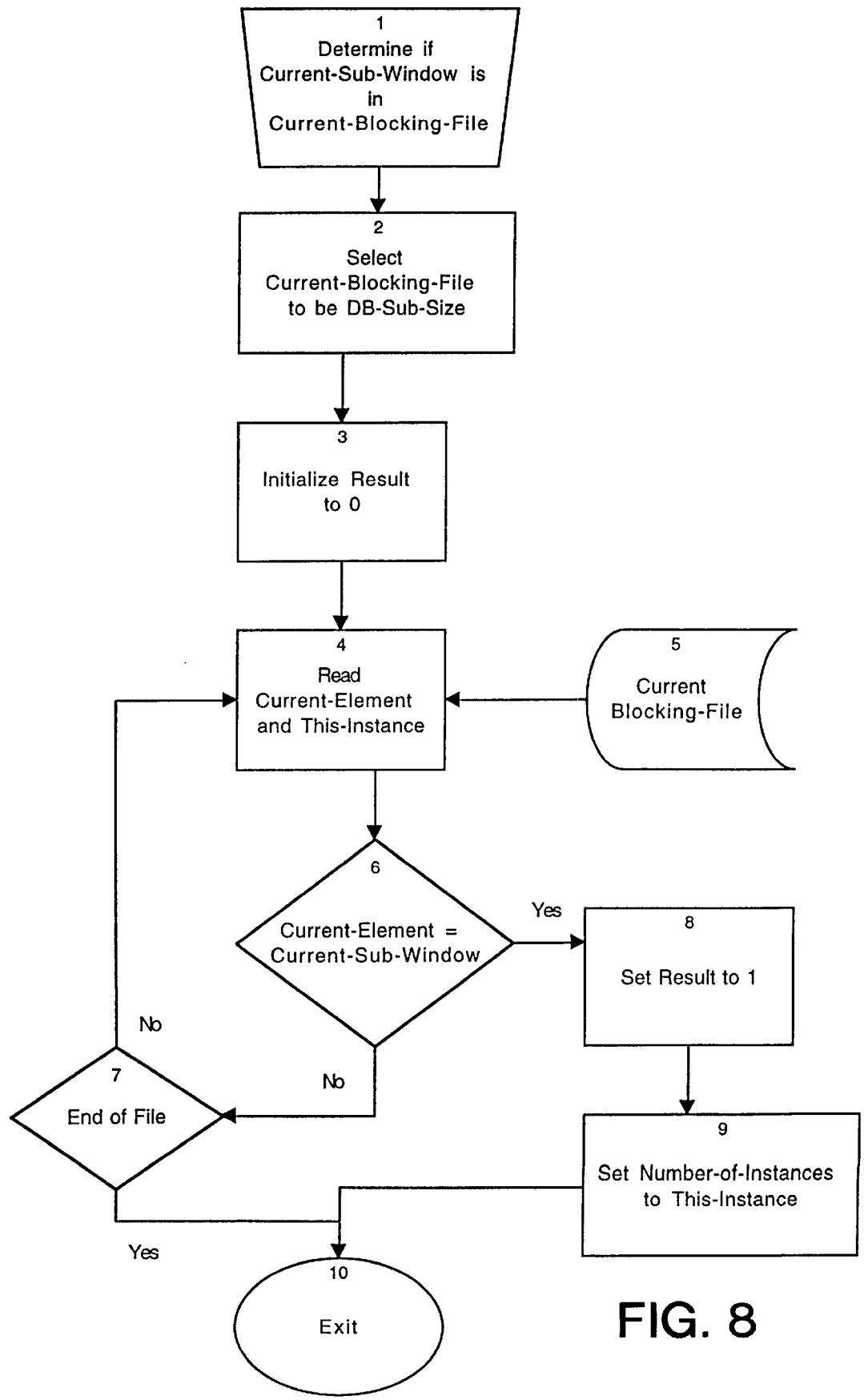
FIG. 8 is a block flow diagram wherein block (22) of FIG. 7 is further broken down.

The "Determine if Current-Sub-Window is in Current-Blocking-File" block (22) in FIG. 7 is expanded in greater detail in FIG. 8.

Figure 9A:
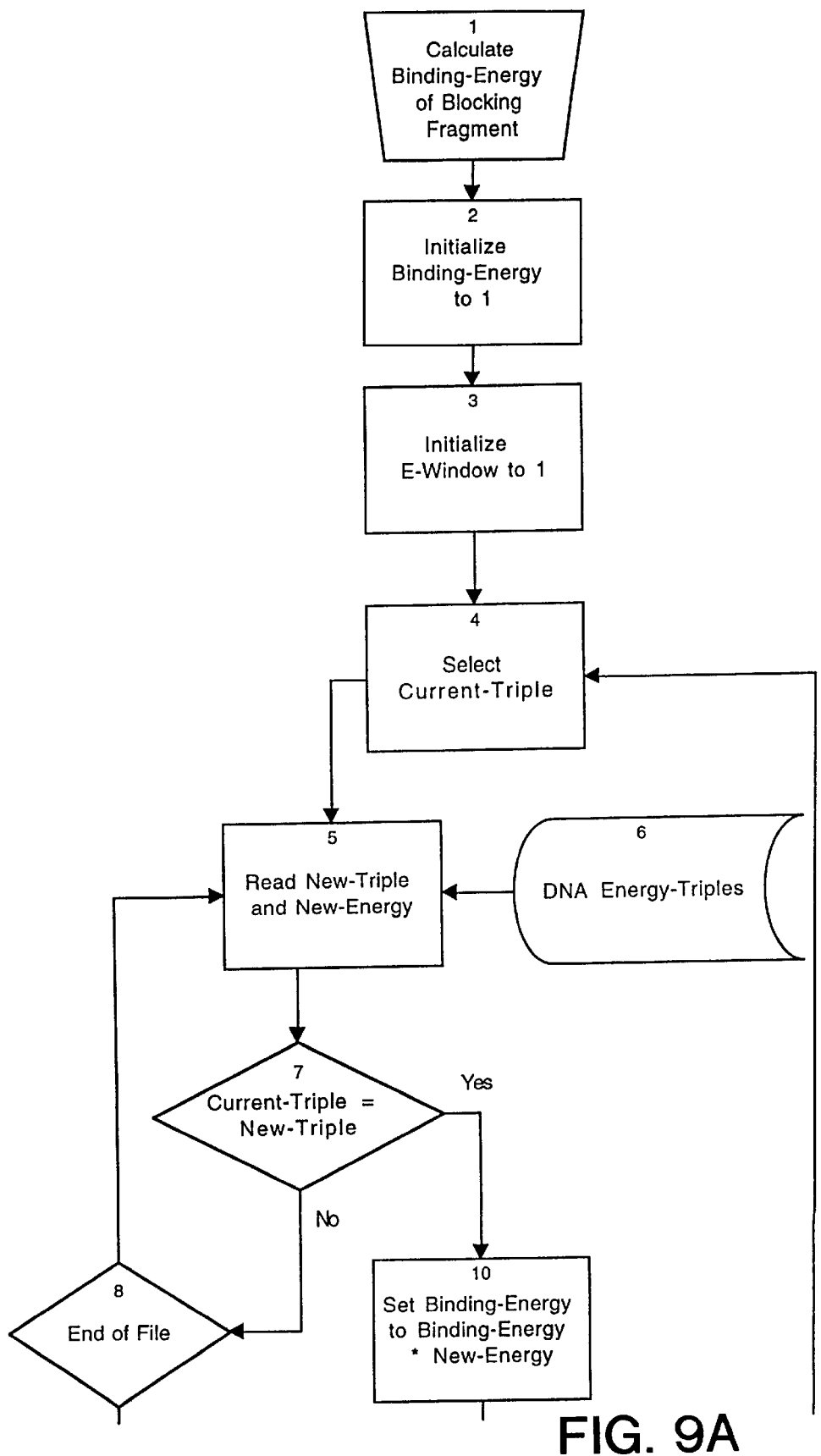
FIG. 9 is a block flow diagram wherein block (24) of FIG. 7 is further broken down.
Figure 9B:
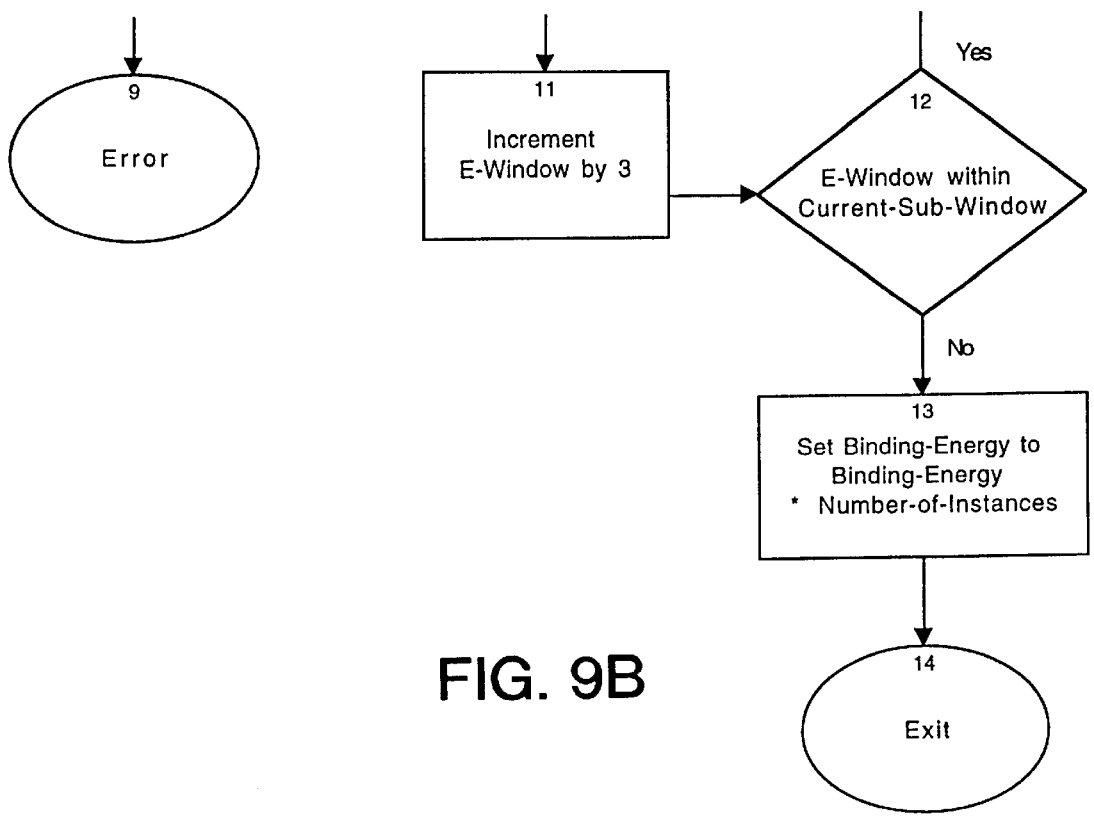

The "Calculate Binding-Energy-of-Blocking-Fragment" block (24) in FIG. 7 is expanded in greater detail in FIG. 9.

By applying the algorithm to a variety of DBP's of varying $n_d$, it was experimentally determined that a value for $n_d$ of 9 is the best starting point in the algorithm, i.e., the process should begin with the search for 9-finger DBP's.

This can be better understood in terms of the selection criterion, $R_b$, used in evaluating various DBP's. In short DBP's, e.g., ones wherein $n_d$=4 or 5, Binding Energy block, which increases geometrically as the product of all Binding Energy$_{domain}$'s, is significantly lower, and Binding Energy$_{site\ n}$ values are relatively large. However, as $n_d$ increases, the numerator of $R_b$ increases dramatically, while, it has been observed, the denominator, representing "background" or "noise," does not significantly change. Thus, the case of $n_d$=9 provides assurance of high affinity and specificity of binding without also bringing on the possibility of undue computational needs.

However, it should also be emphasized that the present invention is not limited to the design of DBP's wherein $n_d \leq 9$. For that matter, it will also be appreciated that, while $n_d$=9 has been found to be the best starting point, the best DBP for a given situation may turn out to be one wherein $n_d$<9, the length of the target DNA sequence notwithstanding. The concept of the invention can be applied to the design of DBP's of any length as required.

In any event, for a given DNA sequence of N nucleotides, there are N-27, 9-finger DBP sequences. Each of these can be ordered in terms of strength of binding by evaluating the energy function for each 3-nucleotide segment as set forth in part (e) of the design method disclosed above.

In initial computational experiments, a selectable sequence could have no 8, 7, 6, 5, and 4-finger subsites; however, with the present system, only the sum of the subsite binding energies need be minimized. As a result, it does not matter whether the subsite binding energy comes from 3-finger subsites, 4-finger subsites or even (in principle) larger subsites. This simple change from logical exclusion to energetic exclusion has been mandated not so much by examination of the yeast genome, but more by examination of the worm genome.

The central portion of the instant algorithm is, in the case of finding an acceptable $n_d$-finger site (e.g., a 27-base segment for a 9-finger DBP), the search against all other $n_d$-finger sites in the entire genome to see if there are any similar sites. If such turns out to be the case, the DBP with the highest $R_b$ value is selected. Furthermore, the algorithm checks to see if there are any equivalent 8-finger, 7-finger, 6-finger, 5-finger and 4-finger subsites in the whole genome for a given 9-finger site. In the event no acceptable 9-finger site is found, the algorithm then searches for a suitable 8-finger site. If necessary, the search is continued for a 7-finger site and so on, until an acceptable DBP binding site is found.

Within the search for a 9-finger DBP, the algorithm looks at all 27-base sequences, which are called "frames." Each frame is evaluated to determine its interaction with DNA and the interaction of all other subframes down to 3-finger subsites. The number of instances of each frame and subframe in the genome has been recorded during the genome processing phase of the execution of the software. The sequence of the frame or subframe is evaluated as a product of the binding energy of each ZF. Each ZF domain recognizes three DNA bases. The underlying DNA sequence that a ZF recognizes determines how many hydrogen bonds, water contacts and hydrophobic contact exist between the ZF and the DNA.

The way the algorithm detects whether a given $n$,-base site occurs in other places in the genome is by looking in a B-tree for the site. The whole genome is processed for each of the $n_d$-finger sites. The algorithm contains means for sorting and merging the myriad fragments and, in the end, there is produced an ordered list of all the blocking fragments for all the different finger sizes.

EXAMPLE 1

The following is given as an example of how the search for, and design of, a DBP is typically carried out. It involves screening for 9-finger DBP's (i.e., $n_d$=9) to bind to a target DNA sequence of 100 nucleotides (i.e, N=100). The sequence is screened, beginning with position 1, for every 27-nucleotide sequence, i.e., 1–27, 2–28, 3–29 etc., in the entire 100-nucleotide sequence. Once this has been done, the 9-fingers are broken down into 3-finger sections, i.e., 1–3, 2–4, 3–5 etc. The algorithm scans and looks for relative strengths of binding. The idea is to maximize the ratio of DBP binding to subsite binding, $R_b$, thus eliminating those 9-mers interacting with the greatest numbers of subsites.

The algorithm of the present invention was applied to the genomes of S. cerevisiae and C. elegans as illustrated by the following examples:

EXAMPLE 2

The algorithm has been applied to the screening of the yeast genome. Two chromosomes of yeast, containing 110 and 447 genes, respectively, have been processed. For each gene the algorithm selected the $n_d$-finger sequence with the lowest sum of subsite binding energies. In yeast the number of 3-finger blocking fragments is almost maximal (i.e., $4^9$, versus $4^{12}$ maximal). In the worm genome (see Example 3), the 3-finger blocking sequences are absolutely maximal. In yeast the 4-finger blocking sequences are large in number but the population of 5-finger blocking sequences is relatively small. In worm the 4-finger blocking sequences are larger in number than the 5-finger blocking sequences, but the latter are larger in number relative to yeast. In going in the future from worm to human, one can expect that the 4-finger blocking sequences might come close to saturation (i.e. close to $4^{12}$) The algorithmic analysis was performed for 2 of the 16 chromosomes of yeast. The 557 cenes in the first two chromosomes seem to present a realistic picture of properties of all the chromosomes in the yeast genome. Sample calculations have been run on the whole yeast genome but these results are not different from those produced by calculating the properties of just two chromosomes' worth of genes. The results of the analysis of 100 yeast genes, typical of the findings throughout the analysis of the yeast genome, are presented in Table 4.

The power of the algorithm is further demonstrated in the results displayed in FIGS. 10–14. The figures display results obtained for all 557 genes of the two yeast chromosomes on which the studies were focused.

Figure 10:
FIG. 10 shows the distribution of binding strengths of acceptable 9-finger DBP's across the yeast genes analyzed.

The strength of each acceptable 9-finger DBP can be calculated. FIG. 10 shows that the strengths of binding of all the acceptable 9-finger DBP's are uniformly distributed. If this curve were bowed down, then the stronger frames would be more preferred. If this curve were bowed up, then the weaker frames would be preferred.

Figure 11:
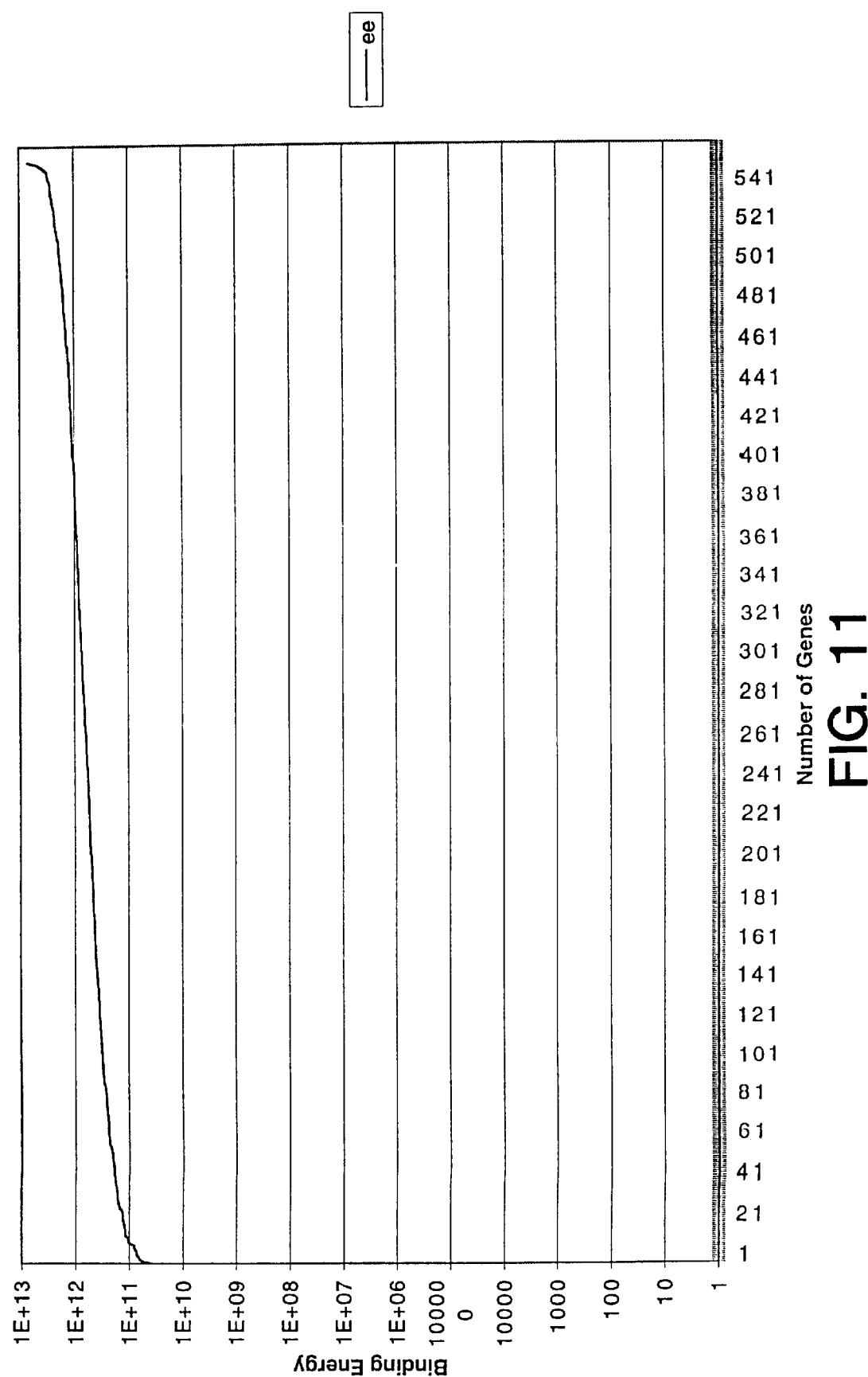
FIG. 11 shows the values of the binding energies of the acceptable 9-finger DBP's found for the yeast genes analyzed.

FIG. 11 shows that the binding energies (Binding Energy$_{block}$'s) of the acceptable 9-finger DBP's are uniformly distributed between $10^{11}$ and $10^{13}$ binding units.

Figure 12:
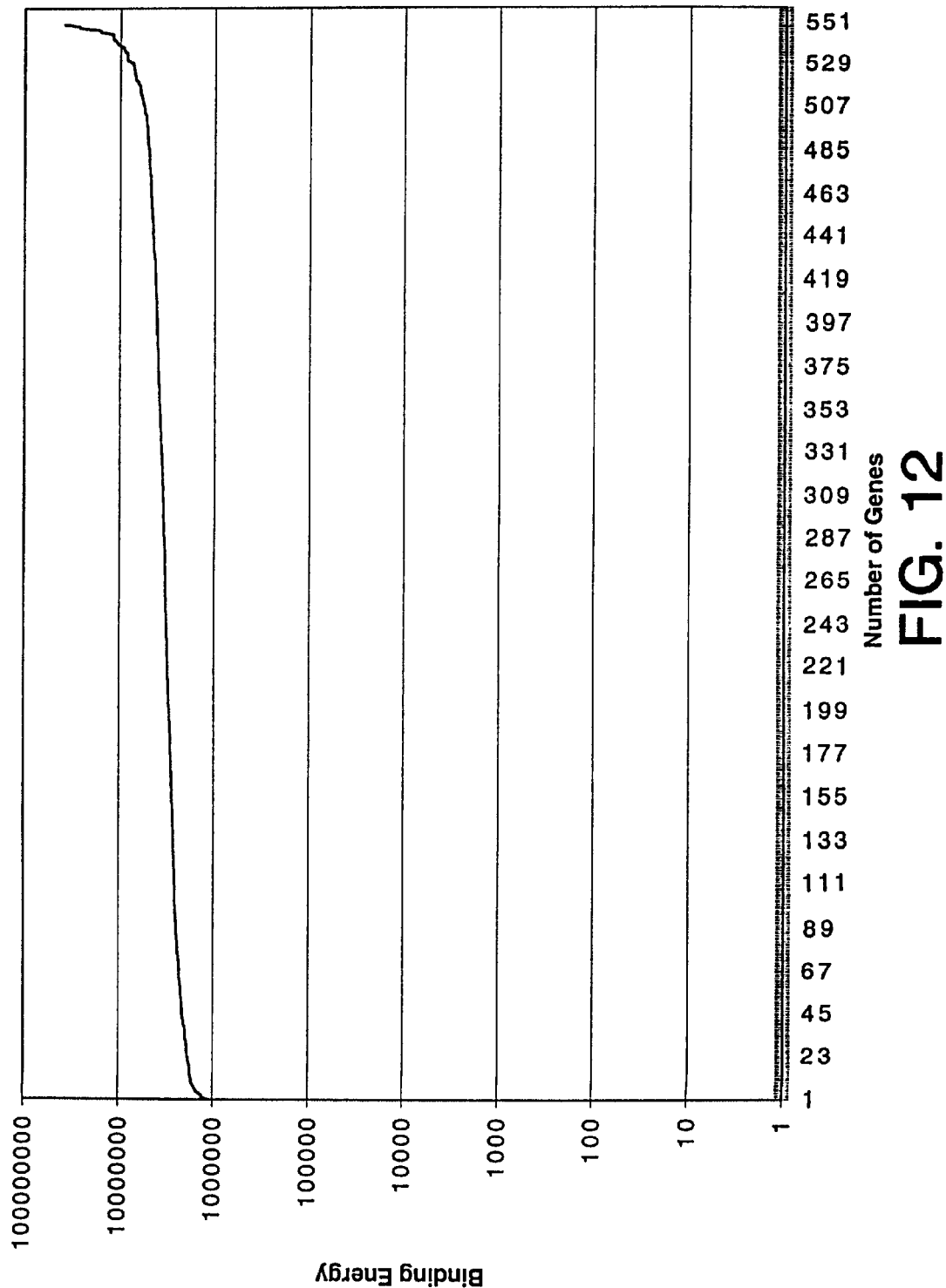
FIG. 12 shows the distribution of DBP subsite (spurious) binding energies across the yeast genes analyzed.

FIG. 12 shows that the distribution of the sum of the spurious subsite binding energies (Binding Energy$_{site}$'s) is itself uniform in the range of $10^6$ to $10^8$ binding units.

Figure 13:
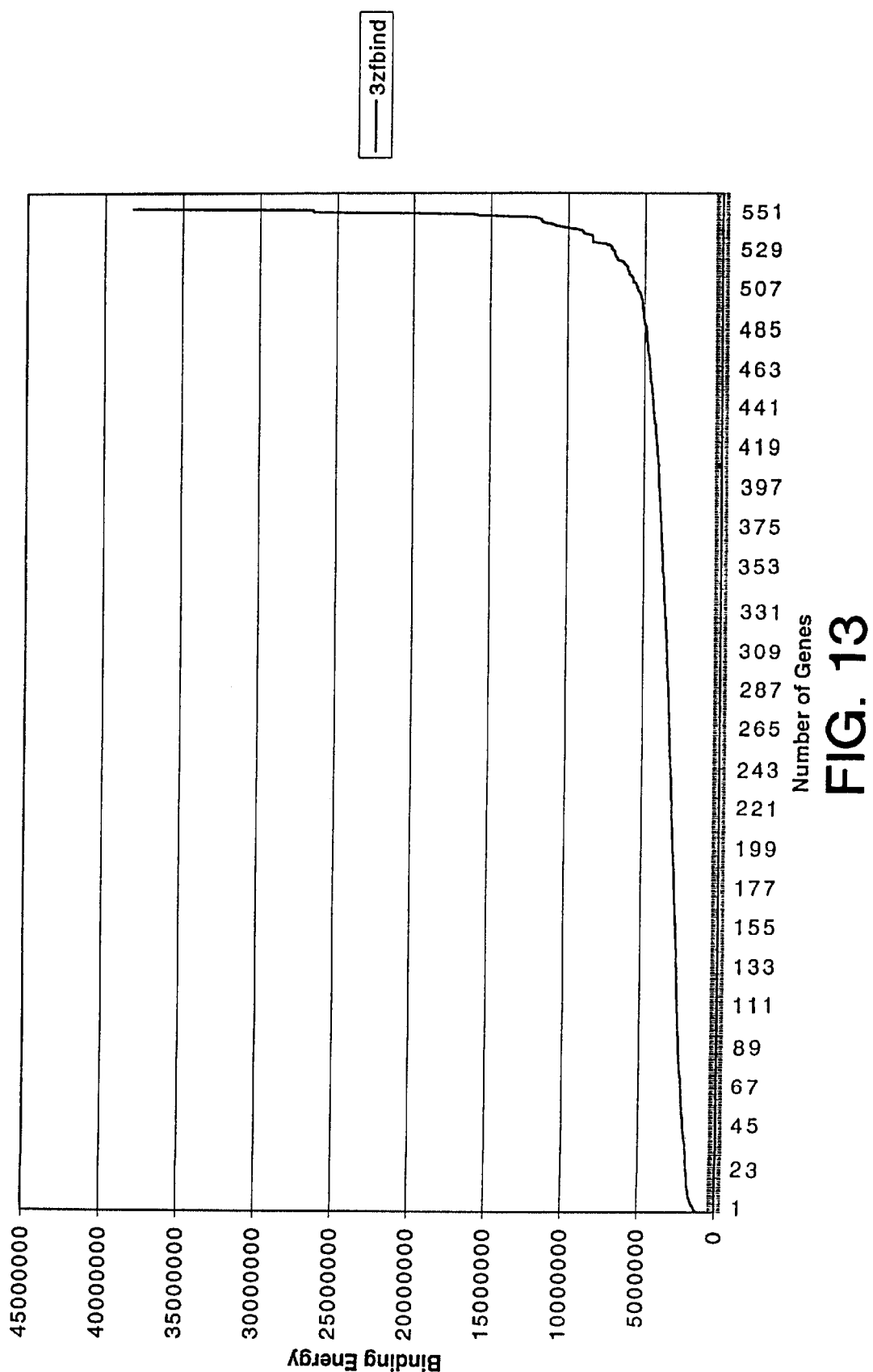
FIG. 13 shows, in nonlogarithmic fashion, the distribution depicted in FIG. 12.

FIG. 13 is a nonlogarithmic version of FIG. 12. It shows that most of the acceptable 9-finger DBP's have spurious subsite binding energies of less than $5\times10^6$.

Figure 14:
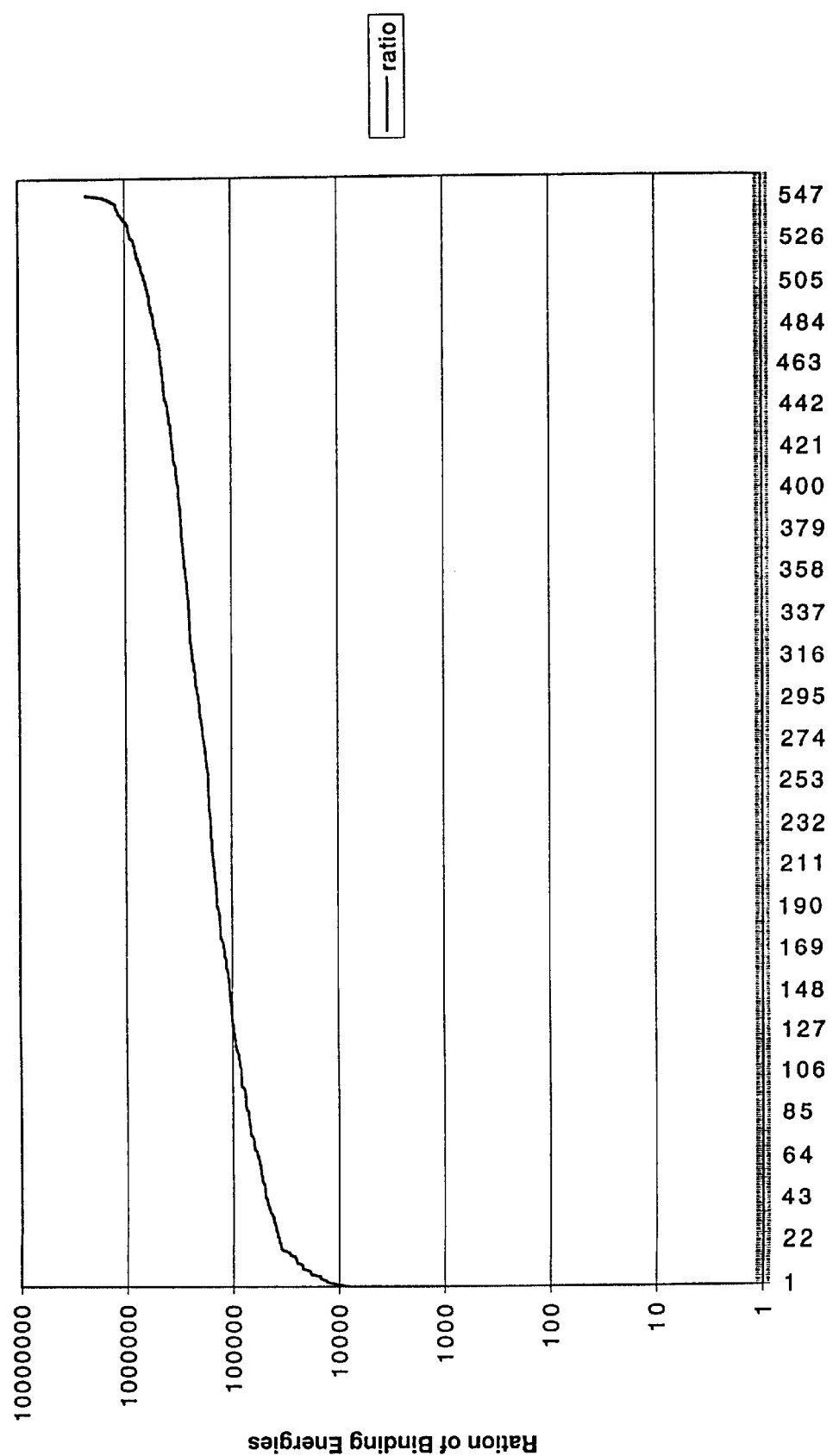
FIG. 14 shows the ratios of binding energy to subsite (spurious) binding energy, across the yeast genes analyzed, for the acceptable 9-finger DBP's.

FIG. 14, produced by taking the ratios of the FIG. 11 values to those of FIG. 12, is a graph of the $R_b$'s for the 9-finger DBP's. This chart shows that the ratio of the DBP binding strength of the acceptable 9-finger DBP's to the sum of the binding energies of the spurious subsite interactions varies from $10^4$ to $10^6$.

Figure 15:
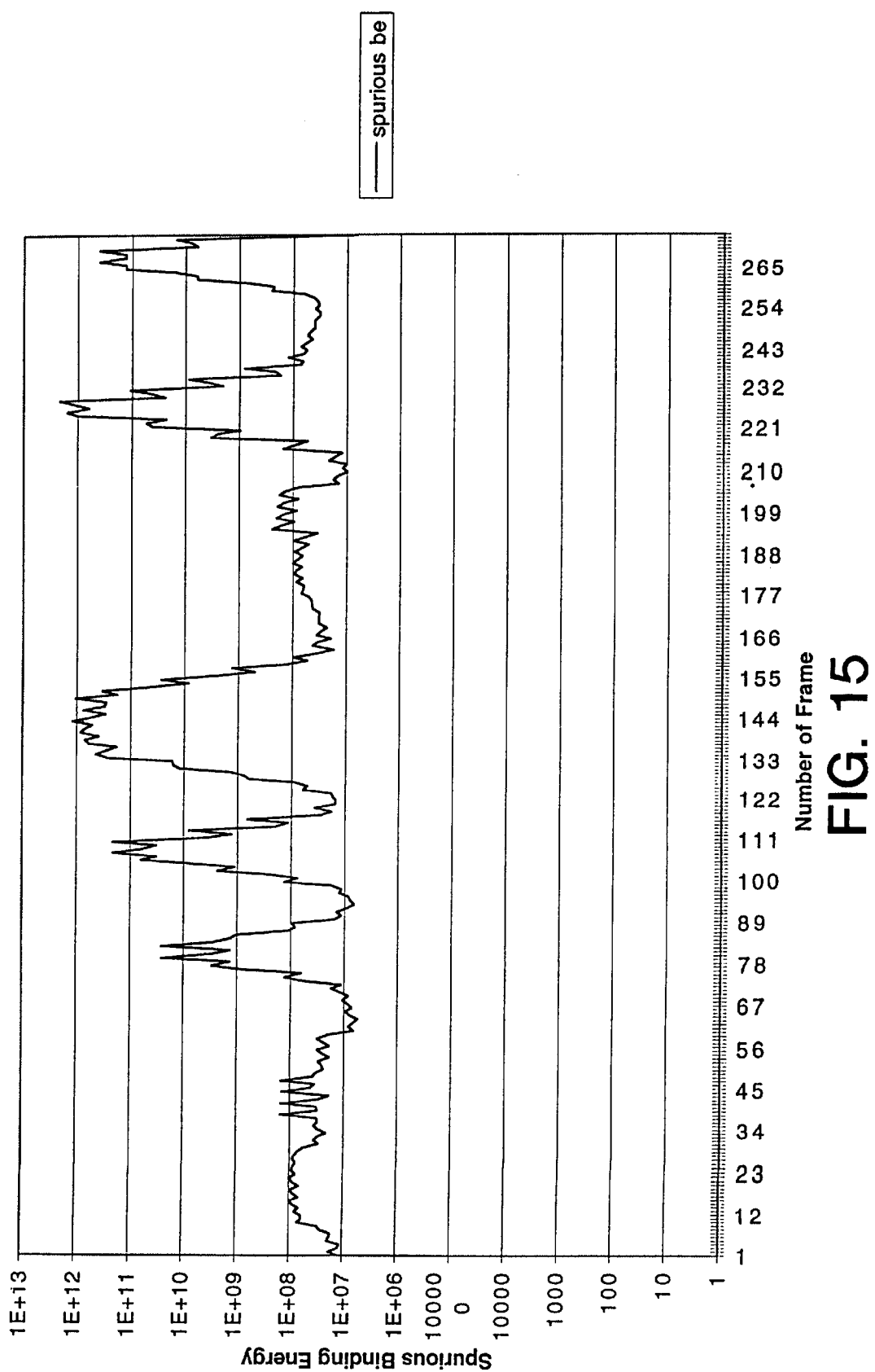
FIG. 15 shows the values of the spurious binding energies for each of the 27-base-pair (bp) frames of the 300-bp promoter region of yeast gene YAR073.
Figure 16:
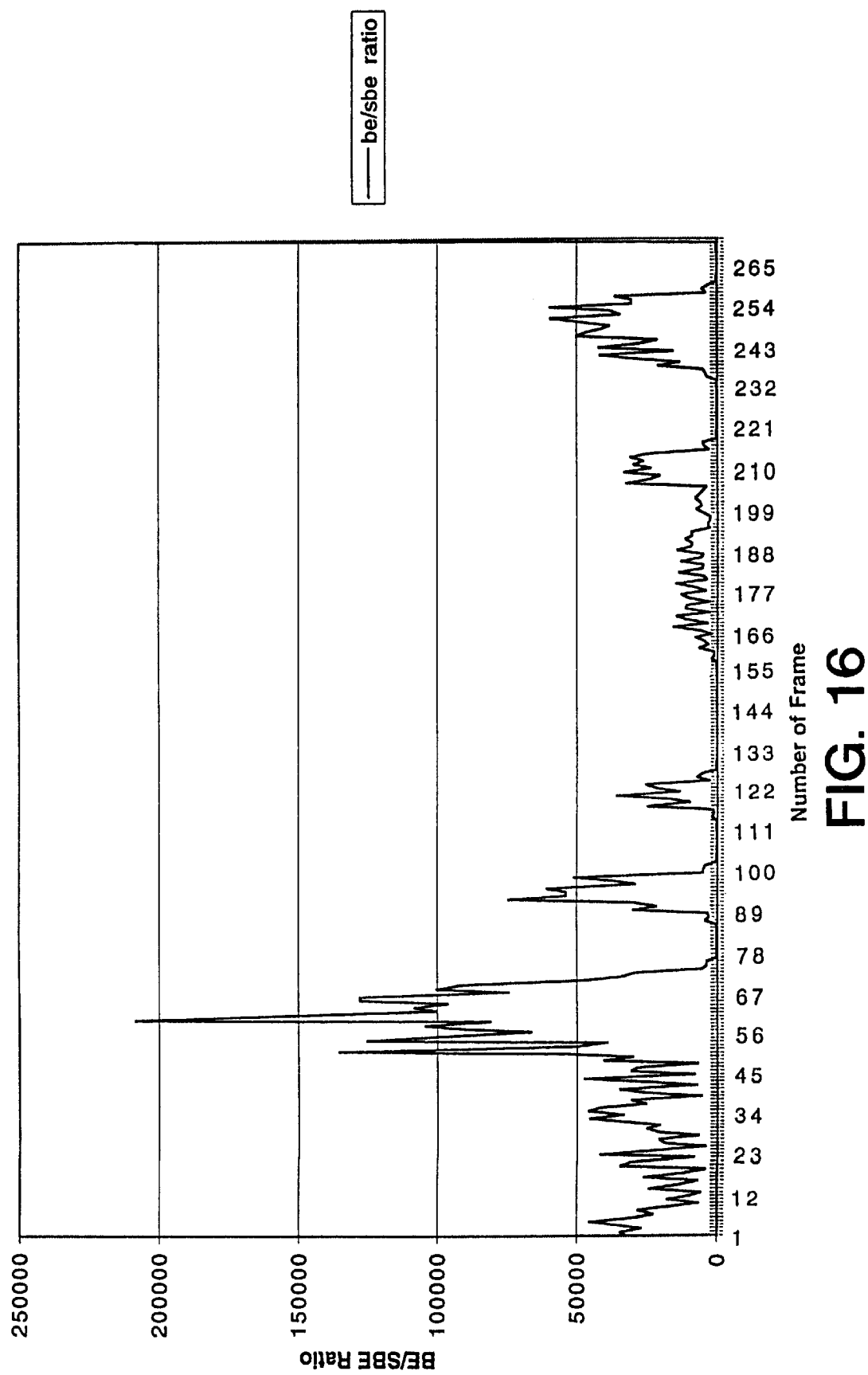
FIG. 16 shows the ratios of binding energy to subsite (spurious) binding energy for each of the 27-base-pair (bp) frames of the 300-bp promoter region of yeast gene YAR073.

The analytical tools of the present invention were also employed in the further analysis of a single yeast gene, YAR073, in particular the 300-bp region of the promoter immediately upstream of the coding region. The full sums of the subsite binding energies (SBE's) for each 27-base frame in this portion of the gene were determined; the results are depicted graphically in FIG. 15. The primary binding energies (BE's) were also determined, and a correlation was found between the SBE values and the values of the ratios of BE:SBE ($R_b$). Still further (FIG. 16), it was seen that the peaks of the plot of the $R_b$ values correspond to the footprints of the transcription factors of the same gene (determined in a separate study).

EXAMPLE 3

Application of the algorithm according to the instant invention to 100 genes in C. elegans showed that the system can be applied as successfully to C. elegans as to S. cerevisiae. The results of analysis of the 100 C. elegans genes are presented in Table 5.

Figure 17:
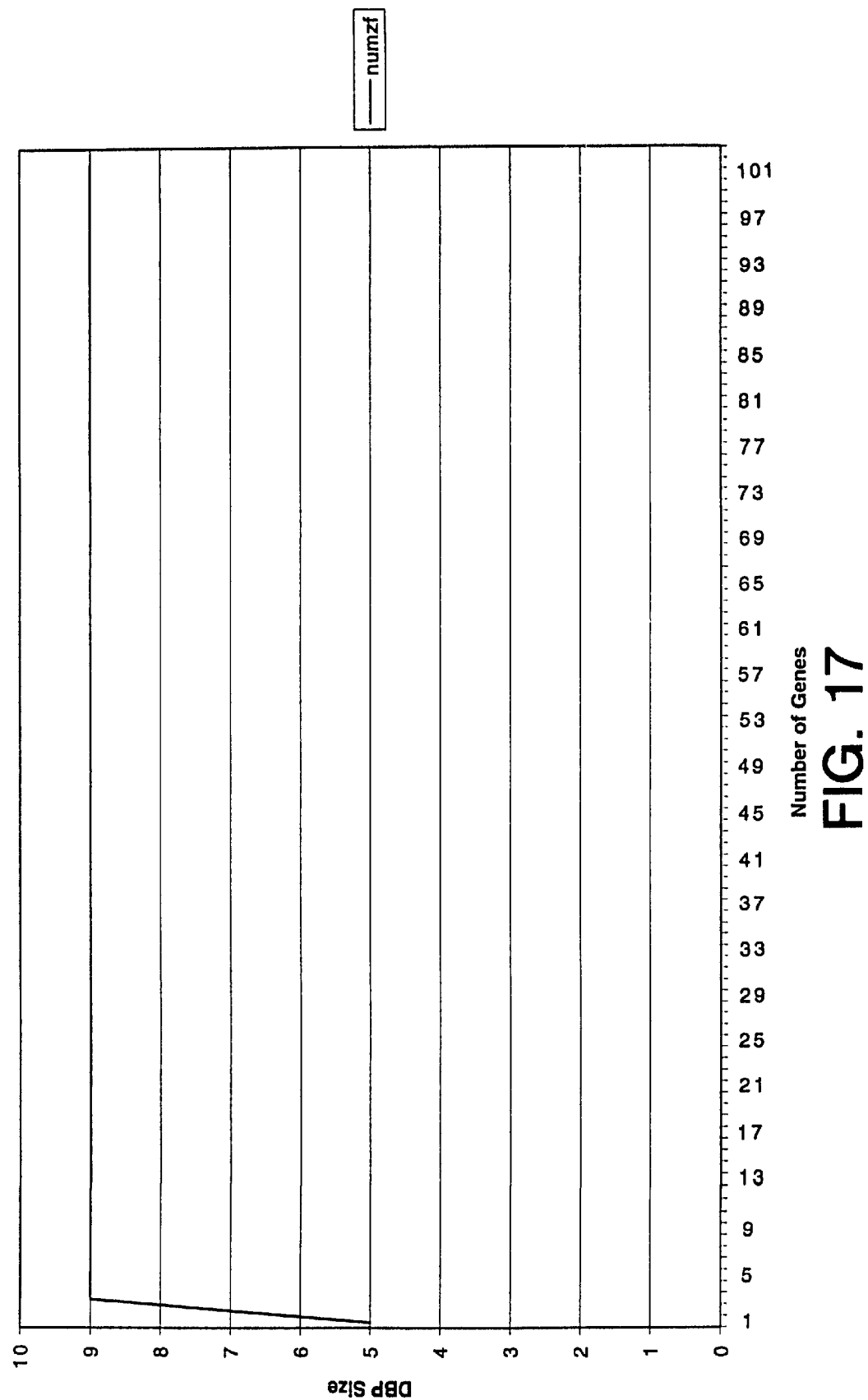
FIG. 17 shows the distribution of sizes of acceptable DBP's across the C. elegans genes analyzed.

In FIG. 17, it can be seen that, for one of the analyzed C. elegans genes, only a 5-finger DBP could be designed. For another gene, only a 7-finger DBP could be designed. These two genes, 2 and 32, are not seen in Table 5, since it presents results of the analysis only for those genes (98 out of 100) for which a 9-mer could be designed. In any event, the results depicted in FIG. 17 are in keeping with the expectation for analysis of the entire C. elegans genome namely, that the distribution of 5- through 9-finger DBP's is somewhat different than in S. cerevisiae.

Figure 18:
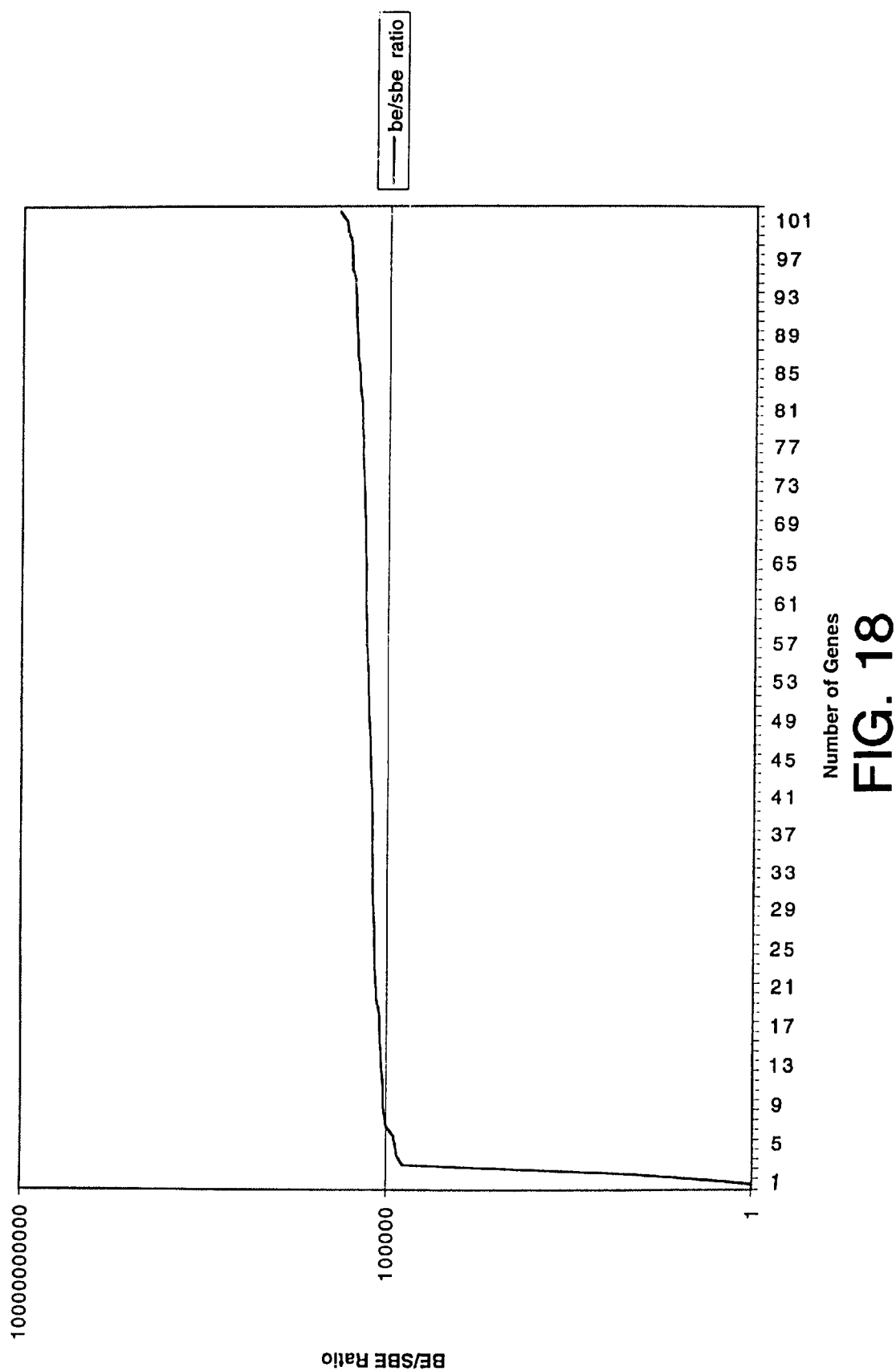
FIG. 18 shows the ratios of binding energy to subsite (spurious) binding energy, across the C. elegans genes analyzed, for the acceptable DBP's.

FIG. 18 represents the same analysis for the C. elegans genes as was depicted in FIG. 14 for S. cerevisiae genes. FIG. 18 shows a similar $R_b$ value distribution to that seen in FIG. 14.

Examples 2 and 3 demonstrate the applicability of the instant invention to the design of DBP's for the genomes of two widely disparate organisms. The various results of the application of the algorithm to the yeast genome, in particular, and also to the worm genome, show the power of the algorithmic tool and demonstrate its foundation in reality, i.e., that it does not merely provide a random and/or theoretical analysis. It is to be expected, on the basis of these analyses, that the inventive algorithm can be extended to the design of DBP's for any desired segment of the genome of any organism of interest, including that of a human.

Although the instant algorithm involves a search against the entire genome of an organism, the results of the present studies strongly indicate that lack of complete knowledge of the genome of a given organism would not constitute an impediment to application of the present invention to the design of DBP's for that organism. One would expect to be able to use the knowledge of block sequences obtained in the studies presented herein on S. cerevisiae (a unicellular organism) and C. elegans (a multicellular organism) to form valid estimates of allowable sequences for the systems of higher eukaryotes.

For example, the present studies on yeast and worm indicate that the genomic "noise," in this context the spurious binding site energies, is relatively constant, and this can be projected to higher, more complex organisms as well. In other words, one would expect from the demonstrated combinatorics of DNA sequences to be able to extrapolate, or extend, the present algorithm to the analysis of more complex genomes, however much is known of the specific sequences therein, with the object of designing effective DBP's. Furthermore, as the entire genomes of larger organisms, e.g., *D. melanogaster*, become known, they will provide further keys to the analysis of the genomes of higher organisms, including humans.

A DBP as specified above may be built by using standard protein synthesis techniques; or, employing the standard genetic code, may be used as the basis for specifying and constructing a gene whose expression is the DBP.

Proteins so designed can be used in any application requiring accurate and tight binding to a DNA target sequence. For example, a DBP, according to the instant invention, can be coupled with a DNA endonuclease activity. When the resultant molecule binds to the target DNA, said DNA can be cut at a fixed displacement from the DBP binding site.

Similarly, in instances in which the target DNA sequence is a promoter, one can produce a promoter-specific DBP which, when bound, will act to alter (i.e., enhance, attenuate or even terminate) expression of a given gene or, alternatively, genes under control of that promoter.

As another application, a DBP could be designed to bind specific DNA sequences when attached to solid supports. Such solid supports could include styrene beads, acrylamide well-plates or glass substrates.

In order to realize the specific applications mentioned above, as well as the full scope of applications possible through the instant invention, the DBP can be designed as set forth above to include the added feature of a pre- and/or postdomain amino acid sequence of arbitrary length. This would include, for example, the coupling of the basic DBP to an endonuclease or to a reporter or to a sequence by which the DPB could be coupled to a solid support.

Accordingly, the instant invention includes DBP's that bind to a predetermined target double-stranded DNA sequence of 3n (where $n \geq 1$) base pairs in length of the form:

$$NH_2-X_{0-m}-ZiF_1-[\{linker\}-ZiFi]\ldots-[\{linker\}-ZiF_n]-X_{0-p}-COOH$$

wherein each $ZiF_1$ to $ZiF_n$ is a ZF domain of the form set forth above; {linker} is an amino acid sequence as set forth above; $X_{0-m}$ stands for a sequence of from 0 to m amino acids and $X_{0-p}$ stands for a sequence of from 0 to p amino acids. The values for m and p and the identities of the amino acids are determined by the particular protein(s) or amino acid sequence(s) to be coupled to the DBP for a given application.

In a further embodiment of the invention, the $Zn^{+2}$ atom, which forms a complex with the two cysteine and two histidine amino acids in a specific ZF motif, can be substituted by a $Co^{+2}$ or a $Cd^{+2}$ atom, thus making a "cobalt finger" or a "cadmium finger."

The rules presented in Table 2 ("rule set A") are to be regarded as the "first choice" rules for optimal combinations in ZF-DNA recognition. However, it should be emphasized, as indicated in column B ("rule set B") of Table 1 or Table 3, that there are many alternative AA combinations that would also be expected to be important in the design of DNA-binding proteins capable of forming useful ZF-DNA complexes.

TABLE 4

Scanning the complete *S. Cerevisiae* genome for conflicts — DBP's designed against the coding region of each gene

| Chromosome | Gene | Optimal DNA Sequence in Gene* | Zf1 Z1 | Z2 | Z3 | Zf2 Z1 | Z2 | Z3 | Zf3 Z1 | Z2 | Z3 | Zf4 Z1 | Z2 | Z3 | Zf5 Z1 | Z2 | Z3 | Zf6 Z1 | Z2 | Z3 | Zf7 Z1 | Z2 | Z3 | Zf8 Z1 | Z2 | Z3 | Zf9 Z1 | Z2 | Z3 | DBP Binding Energy | Binding Energy | Ratio of Binding Energy to Spurious |
|---|---|---|---|---|---|---|---|---|---|---|---|---|---|---|---|---|---|---|---|---|---|---|---|---|---|---|---|---|---|---|---|---|
| 1 | 1 | CCT ACT CTC AGA TTC CAC TTC ACT CCA | E | N3 | Q2 | Q | N3 | Q2 | E | I | I | Q | N | Q | I | I | R2 | E | N | E | I | I | R2 | Q | N3 | E | E | Q | 7374132 | 132836 |
| 1 | 2 | TCA GAG CTC ACT TAG CCC AAT ACT ACA | I | D | Q | R | N | R | E | E | E | Q | Q | R2 | N | R | R | E | Q3 | R2 | N | N3 | Q3 | Q | N3 | Q | D | Q | 24192270 | 166073 |
| 1 | 3 | GCC GCT TGG GAC GTC GGA GAA GGA GCC | R | Q3 | Q3 | R | N3 | Q2 | H | I | H | R | N3 | N | R | I | R2 | R | D | Q | R | N | Q | R | N | Q3 | R2 | 8480520 | 701860 |
| 1 | 4 | GAA AAG CAT ACA GCT ATA TDC GAT ACA TCA | R | N | Q | R | Q | R | E | Q1 | O2 | Q | I | N3 | R | I | N3 | I | I1 | Q3 | R | N | Q | R | D | Q | R2 | Q | 19226970 | 313442 |
| 1 | 5 | AGT AGC ATA ATA GGA TCT AGT ACT GDC | Q | H1 | Q2 | H1 | I | Q | I | H1 | R2 | Q | H1 | H1 | R | I1 | R2 | R | H1 | H1 | R | N | R | H | N3 | D | Q3 | R2 | 15168192 | 176738 |
| 1 | 6 | GCC GTG GAA ACA ATT GCA GAG GAG ATG | R | Q3 | R2 | R | R | R2 | R | R | R2 | Q | Q | Q | R | I | R2 | R | R | Q2 | R | R | R2 | R | N | R | I | R | 309413791 | 176738 |
| 1 | 7 | CCA AGT CGA GCT TAA AGT TAA GTG | E | D | Q | Q | H1 | Q2 | R | R | R | Q | Q | Q | N | Q | Q3 | R | Q3 | Q2 | N | H1 | Q2 | I | N | Q | R | I | R | 9355725 | 320720 |
| 1 | 8 | GAC TAC ACC GGC ATG CCT GDC AGC AAA | R | N | Q3 | I | N | E | N | Q | H1 | R | H1 | R2 | I | N3 | N | E | N3 | Q3 | R | H1 | Q3 | Q | H1 | I | R | 6539130 | 487737 |
| 1 | 9 | ACT TGG ACT GCC GAG GTC GAT CAA | Q | N3 | Q2 | I | H | R | Q | N3 | Q2 | R | R | Q2 | R | N | R | E | H | R | R | I | R2 | R | Q | N | Q3 | 442890 | 1094811 |
| 1 | 10 | GAC CCA ACT GCG GCT GDC AAG GAG | R | N | Q3 | N | D | Q | Q | N3 | Q2 | R | E | R2 | R | E | E | R | N3 | R2 | R | Q3 | R2 | Q | I | R | R | 112136401 | 011037 |
| 1 | 11 | CCT GCC AGC AGT TGT CCG GAC CTG CAT | R | N3 | Q2 | N | H1 | Q2 | Q | H1 | R2 | R | H1 | R2 | I | H1 | Q2 | R | E | E | R | N3 | Q3 | E | I | R | E | Q1 | Q2 | 6292670 | 563027 |
| 1 | 12 | GAT AAC ACA GTG CAG AAG ACT CCT ACA | R | Q | Q2 | R2 | Q | R2 | Q | D | Q | R | H1 | R2 | R | E | Q | R | Q | Q | R | N3 | Q2 | R | I | R2 | R | Q | 18371043 | 492068 |
| 1 | 13 | TAT GCA DCC GAT ACA GGT GTC GAG | I | N | Q3 | R | D | Q | E | Q3 | R2 | R | Q | Q2 | D | Q | R | E | H | H1 | Q3 | R | H1 | Q2 | I | R2 | R | 7619823 | 768933 |
| 1 | 14 | CAA GAG CAC GGC CGC AGT AAG CAC | E | N | Q3 | E | N | Q3 | E | N | Q3 | E | H1 | Q2 | H1 | R2 | N | Q3 | R | Q | R | H1 | Q2 | Q | R | E | N | E | 4512410 | 1279511 |
| 1 | 15 | GAG ATA CCC GTG ATA CGT CGC GGT AAA | R | N | R | Q | I | Q | Q | Q3 | R2 | R | I | R2 | Q | Q | R2 | Q | R2 | R | R | R | H1 | Q2 | R | H | R | E | Q1 | Q | 2512107 | 903296 |
| 1 | 16 | AAT GGG GCA CCT DCA GAG GGT GAT | Q | N | Q3 | N | N | Q | E | Q3 | R2 | N | E | N | E | N3 | Q2 | R | Q | Q2 | R | N | Q3 | R | R | H | N | Q | 10115586 | 700491 |
| 1 | 17 | GAG AGA CDC CAG GCG TGA GAC ACG TCT | R | N | R | R | N | Q | E | Q3 | R2 | Q | E | R2 | E | R | E | R | Q | R | N | N3 | Q3 | Q | E | R | I1 | N3 | Q2 | 44303761 | 101825 |
| 1 | 18 | ACC TCC GCT GTC ATG GGT ACG GGT GGC | Q | Q3 | R2 | I | Q3 | R2 | R | N3 | Q2 | I | N | R | E | I | R | E | R | H1 | Q2 | E | R | H1 | R2 | 4927770 | 713565 |
| 1 | 19 | GAA CCG AGT GGG TAG CGA TCT AAG CGA | R | N | Q | E | Q3 | R2 | R | H1 | Q2 | N | R | H | R | N | Q | I1 | N3 | Q2 | H1 | R2 | 2905470 | 1180262 |
| 1 | 20 | GAT GGA ACA CCC AAG GGT CCT GAA | R | Q | Q | E | D | Q | D | Q | D | Q | R | Q | R | Q2 | R | E | Q2 | H | Q2 | H1 | E | N | Q | 11022512 | 583391 |
| 1 | 21 | ACC GAC CAT ACA GGA CGT CCT GDC ACC | Q | Q3 | R2 | R | N | Q | E | Q1 | Q2 | Q | D | Q | R | N | Q | R | E | Q | N3 | Q2 | R | Q3 | R2 | Q3 | R2 | 9693576 | 1085516 |

TABLE 4-continued

Scanning the complete S. Cerevisiae genome for conflicts – DBP's designed against the coding region of each gene

| Chromosome | Gene | Optimal DNA Sequence in Gene* | Specific Amino Acids in DBP | | | | | | | | | | | | | | | | | | | | | | | | | DBP Binding Energy | Binding Energy | Ratio of Binding Energy to Spurious |
|---|---|---|---|---|---|---|---|---|---|---|---|---|---|---|---|---|---|---|---|---|---|---|---|---|---|---|---|---|---|---|
| | | | Zf1 | | | Zf2 | | | Zf3 | | | Zf4 | | | Zf5 | | | Zf6 | | | Zf7 | | | Zf8 | | | Zf9 | | | | |
| | | | Z1 | Z2 | Z3 | Z1 | Z2 | Z3 | Z1 | Z2 | Z3 | Z1 | Z2 | Z3 | Z1 | Z2 | Z3 | Z1 | Z2 | Z3 | Z1 | Z2 | Z3 | Z1 | Z2 | Z3 | Z1 | Z2 | Z3 | | |
| 1 | 22 | GAA AGA CGG AAG CTC GAT CCT AAC GCT | R | N | Q | Q | N | Q | E | H | R | Q | Q | R | E | I | R | Q | I | R | N3 | Q2 | Q | Q1 | R2 | R | N3 | Q2 | 12066840 | 645941 |
| 1 | 23 | AGT CAA CTG GGA AGG GTC CGG CAT CAT | Q | H1 | Q2 | E | N | Q3 | E | I | R | R | R | R | I | Q | R | I | R | R2 | H | E | H | R | E | Q1 | Q1 | Q2 | 7060608 | 422504 |
| 1 | 24 | AGG GTA CGT GGC ACG GGA CCA TCT CAT | Q | Q | R | Q | I | R | R | I | Q | Q | N | Q | Q | Q | R | E | I | R | N | H | R | Q1 | D | Q | I1 | N3 | Q2 | 4607532 | 626666 |
| 1 | 25 | ATG GAC CAC CCG CAT GCC CGC TGT GAG | Q | I | R | R | R | R | E | N | E | E | H | Q | R | E | Q | E | R | R2 | H1 | I | H1 | Q2 | Q | R | N | R | 2450880 | 1266455 |
| 1 | 26 | AAG ACC CDC ACG CCC GTG TCC GCA CCT | Q | Q | R2 | Q | Q3 | Q2 | E | Q3 | R2 | E | Q3 | R2 | Q1 | Q3 | R2 | Q1 | I | Q3 | D | Q | E | N3 | Q2 | 5803812 | 981266 |
| 1 | 27 | GAT CAG CCC GCC GGC CCT GGT GCG GAC | R | Q | R | E | Q | R | E | E | R | Q3 | R | R | N3 | H1 | R | N3 | I | R | R | E | R | N | Q3 | 2742660 | 3269843 |
| 1 | 28 | AGT CCG CAC GAG GGC CGG CGG GCT GAT | Q | H1 | Q2 | E | D | R | R | Q | E | R | E | R2 | H1 | H1 | R2 | N3 | H1 | R2 | E | R | R2 | Q | N | Q2 | 2263544 | 1870532 |
| 1 | 29 | AAT GGC GCT AAC CGG GAC AGC GAC | Q | N | Q3 | R | H1 | N3 | E | N | N3 | E | R | R | H | N3 | R | H | H1 | R | E | H | R | N | N3 | 6611550 | 1263414 |
| 1 | 30 | GCC ACT GCC GDC TCT GTC AGC GCT GCC | R | Q3 | R2 | N3 | R | Q | N3 | Q3 | Q3 | Q1 | I1 | N3 | H1 | R | R | Q | H1 | Q2 | Q | H1 | R2 | R | H1 | N3 | Q2 | 10878345 | 738828 |
| 1 | 31 | ACT CCG AGG CGA GDG CAA AGC GGA ACA | Q | N3 | R2 | D | E | D | Q | Q | Q | R2 | N3 | R2 | E | I1 | N3 | N | E | N | N3 | N | R2 | Q | D | Q | 4999968 | 1239753 |
| 1 | 32 | ACC GTC GCT GCC TCC GCT GTC GCT GCT | Q | Q3 | R2 | I | N | D | N3 | Q3 | Q3 | Q3 | N3 | R2 | Q | R | Q | R | H1 | R2 | R | N | Q | N3 | Q2 | 9376290 | 720036 |
| 1 | 33 | ACG TAG CCA GAC GAG CTC AGT CAA GAG | Q | E | R | H1 | E | R | I1 | R | R | I | I | R | Q | H1 | Q | Q | H1 | R2 | Q | R | Q | N | R | 6475788 | 77552 |
| 1 | 34 | ACC ACC CTG GTT ACC GTC DCC GGT GTC | Q | Q3 | R2 | Q3 | Q | R | H | Q | Q3 | H | R | R2 | R | Q3 | R2 | Q3 | R2 | H | Q2 | R | H | Q2 | 3659040 | 830292 |
| 1 | 35 | ACA ACC CAG GAA AAC GCC TCC GAA GCC | Q | D | R | Q3 | Q | Q | Q | R | H | Q3 | Q1 | Q | N | Q | H | Q | I | Q2 | Q | D | R | R2 | 15634620 | 713817 |
| 1 | 36 | CAA CAA GCG AGA TGG GCG GAT ATC CCA | E | N | Q3 | E | N | E | R | Q | H | R | R | R | R | E | R | E | E | H | I | R2 | R | E | Q | 6125355 | 566708 |
| 1 | 37 | GCC GTC GCT GCC GTC GCT CAA GAG | Q | Q3 | R2 | Q3 | H1 | H1 | R2 | R2 | Q3 | R2 | R2 | Q3 | R2 | R | Q | H1 | Q2 | Q | D | Q | 5445990 | 1053906 |
| 1 | 38 | AAA GGT ACC GCT ACG CCA CCT ACG GGT | R | N | Q | E | R | R | R | R | R | R | R | R | R | E | Q | E | R | R | H | N | Q2 | 6989373 | 950445 |
| 1 | 39 | ACT GAT CGT GAA CCC CGT CAA GGT AAG | Q | N3 | Q3 | Q3 | Q3 | H | R | N3 | Q3 | Q3 | Q1 | Q3 | N | N3 | R2 | H1 | R2 | Q | Q | R | 9882648 | 722977 |
| 1 | 40 | CAA CGG GAC TCC GCA GAC GGG AGC AAT | E | N | Q3 | E | I | R | Q | D | Q | Q | Q | Q | H | R | H1 | R2 | Q | N | Q3 | 3614610 | 1572359 |
| 1 | 41 | CAA CCC GTA CCC CTA GAT CAC TAT | E | Q3 | R2 | R | R | R | R | Q3 | Q3 | R2 | E | Q | Q2 | E | N | E | I | N | Q3 | 5069652 | 739622 |
| 1 | 42 | GAC CCT TAT GCT CTA TCC CAC CAC GAT | R | Q | R2 | E | N3 | Q2 | I | N | R | N3 | Q2 | I | Q | I | Q3 | R2 | R | N | E | R | Q | Q2 | 6148980 | 677592 |

TABLE 4-continued

Scanning the complete *S. Cerevisiae* genome for conflicts – DBP's designed against the coding region of each gene

| Chrom-osome | Gene | Optimal DNA Sequence in Gene* | Zf1 Z1 | Zf1 Z2 | Zf1 Z3 | Zf2 Z1 | Zf2 Z2 | Zf2 Z3 | Zf3 Z1 | Zf3 Z2 | Zf3 Z3 | Zf4 Z1 | Zf4 Z2 | Zf4 Z3 | Zf5 Z1 | Zf5 Z2 | Zf5 Z3 | Zf6 Z1 | Zf6 Z2 | Zf6 Z3 | Zf7 Z1 | Zf7 Z2 | Zf7 Z3 | Zf8 Z1 | Zf8 Z2 | Zf8 Z3 | Zf9 Z1 | Zf9 Z2 | Zf9 Z3 | DBP Binding Energy | Binding Energy | Ratio of Binding Energy to Spurious |
|---|---|---|---|---|---|---|---|---|---|---|---|---|---|---|---|---|---|---|---|---|---|---|---|---|---|---|---|---|---|---|---|---|
| 1 | 43 | CAA GGT GGA CAG CCG AAC ATA GCT GGT | E | N | Q3 | R | H | Q2 | R | N | Q | Q | E | R | E | D | R | R | Q1 | R2 | Q | I | Q | R | N3 | Q2 | Q | H | Q2 | 6691509 | 833912 |
| 1 | 44 | CCG GAT TAC ACG TCT GCC TCG ACC GCA | E | D | R | R | Q | R | I | N | E | E | Q | Q | I1 | N3 | R2 | R | Q3 | R2 | I | D | R | Q | Q3 | Q3 | R | D | Q | 27652514 | 1034213 |
| 1 | 45 | GGT GCC GAT ACG GAT AAT GCG GTA ACT | R | H | Q2 | R | R | Q2 | R | R | Q2 | E | E | Q | R | Q | Q2 | Q | N | Q | R | E | E | R | I | Q | Q | N3 | Q2 | 11200230 | 830360 |
| 1 | 46 | ATC AGC GAC TCT AGG CCG CAC GTT CAG | Q | I | R2 | R | Q | R2 | R | R | Q3 | I1 | N3 | Q3 | R | Q | Q | E | D | R | E | N | E | R | I | Q3 | E | Q | R | 3766644 | 774309 |
| 1 | 47 | ACG CCT GAA AGA GCG CAC ACT CCT GCC | Q | E | R | E | E | R | R | N | Q | Q | Q | N | R | R | R | E | N | E | N | E | E | R | N3 | Q2 | R | Q3 | R2 | 10318266 | 901129 |
| 1 | 48 | TCT AGT GCC CGG AAC ACA CQG AGA GCA | I1 | N3 | Q2 | H1 | R2 | Q2 | N | R | Q3 | Q | I1 | R2 | Q | Q1 | Q | D | H | R2 | E | H | R | Q | E | Q | D | D | Q | 32312521 | 293053 |
| 1 | 49 | AGC GCT GAG AGA GAC GCG GAA GAT | Q | H1 | R2 | R | N3 | Q2 | N | H1 | Q2 | H | E | R2 | N | Q1 | Q | N | R | R | R | D | R | N | Q | Q | Q | Q | Q2 | 17979930 | 777874 |
| 1 | 50 | ACC GCC GCA CCA ACG GCA CTC GCC ACG | Q | Q3 | Q3 | N3 | Q3 | R2 | Q | Q | D | N | D | Q2 | E | Q | Q | N | Q3 | Q | E | H | R2 | E | E | R | E | R | 5487912 | 1015572 |
| 1 | 51 | ACG GGA GAT AGC ACT CCC TCA GGC ACG | Q | E | R | N | R | R | R | H1 | Q | R | Q2 | Q2 | N3 | N3 | R2 | E | Q3 | R2 | E | I | D | R | E | H1 | E | E | R | 5807160 | 9266587 |
| 1 | 52 | GAC GAG GGC GGC GCA GAC CGC ATA GTG | R | N | Q3 | N | R | Q | R | H1 | R2 | D | H1 | R2 | R | Q | R | H1 | I | Q | R | H | R | N | E | R | D | Q | 25793441 | 371038 |
| 1 | 53 | ACC GCT GGC GCA GAC GCC ACT ACC AAG | Q | Q3 | R2 | N | R | N3 | R | D | N3 | N | R | Q3 | R | N3 | Q3 | R | Q3 | R2 | N3 | H | Q2 | R | N3 | Q | Q | N | R | 7686450 | 1600463 |
| 1 | 54 | TAT GAG CCG TAC CAG ATA CGT GCT AAT | I | N | Q3 | N | R | Q | E | E | R | H1 | N | Q2 | Q | E | R | Q | H | Q | R | E | Q | Q | E | Q3 | R | Q | Q3 | 6770394 | 401149 |
| 1 | 55 | CAG ACA CCG AGC CCC GAT CAA GAG | E | Q | R | Q | Q3 | R2 | N | D | R | N | D | R | E | H1 | Q2 | E | Q3 | R2 | E | H | R2 | E | N3 | R2 | R | N | Q | 9717264 | 708788 |
| 1 | 56 | CAT CGC GTT GGC ACT CGG TCC AAG | Q1 | Q2 | R2 | H1 | Q | Q | I | R | D | H1 | R | Q3 | H1 | I | R2 | H | Q | R | I | Q3 | R | R | I | Q3 | E | Q | R | 29375521 | 059390 |
| 1 | 57 | GCT ATT GGG CCT GCC CGG TGT ACG GCC | R | N3 | Q3 | N3 | I | Q3 | H | R | N | E | N3 | Q2 | R | Q3 | R2 | R | Q3 | Q2 | I | H1 | Q2 | Q | Q | Q | R | R | R2 | 30941251 | 175589 |
| 1 | 58 | ATT CCT GAT ACG GCG GTT GAC AAG GAG | Q | I | Q3 | E | Q3 | R2 | Q | Q | Q1 | E | Q2 | Q2 | R | R | R | R | I | R | I | H1 | Q2 | Q | N | Q3 | R | N | R | 12276765 | 572705 |
| 1 | 59 | GAC GCC AGG GAC GAG CAA GGG GAC GAA | R | N | Q3 | R | R | Q3 | R | Q | Q | R | Q2 | R2 | E | R | N | E | N | H | R | H | Q2 | R | R | N | R | N | Q | 68526001 | 938830 |
| 1 | 60 | GTC GCC AAC GCT CAC GGT GTG GAA ACC | R | I | R2 | R | R | Q3 | R2 | R2 | Q1 | N | N3 | Q2 | N | E | R | N | H | Q2 | R | I | H | R | I | Q3 | R | D | Q3 | 7299000 | 880912 |
| 1 | 61 | AGA AGG GGC AAG CGT GGT CGT GAC GAT | Q | N | Q | R | R | Q3 | R | Q | R | Q | Q | N | E | H | Q2 | H | Q2 | R2 | E | H | Q2 | R | R | N3 | Q | Q3 | Q2 | 5511175 | 1080370 |
| 1 | 62 | CAG CAG ACC GAC TAA ACT ACT GCA CGA | E | Q | R | E | E | Q | Q | R | R | N | R2 | R2 | N | N | Q | E | R | Q2 | R | N3 | Q2 | R | D | Q | E | N | Q | 10230030 | 654559 |
| 1 | 63 | CAG CAG ACC GAC TAA ACT ACT GCA CGA | E | Q | R | E | E | Q | Q | R | R | N | R2 | R2 | N | N | Q | E | R | Q2 | R | N3 | Q2 | R | D | Q | E | N | Q | 10230030 | 654559 |

Specific Amino Acids in DBP

TABLE 4-continued

Scanning the complete S. Cerevisiae genome for conflicts – DBP's designed against the coding region of each gene

| Chromosome | Gene | Optimal DNA Sequence in Gene* | Specific Amino Acids in DBP Zf1 Z1 Z2 Z3 | Zf2 Z1 Z2 Z3 | Zf3 Z1 Z2 Z3 | Zf4 Z1 Z2 Z3 | Zf5 Z1 Z2 Z3 | Zf6 Z1 Z2 Z3 | Zf7 Z1 Z2 Z3 | Zf8 Z1 Z2 Z3 | Zf9 Z1 Z2 Z3 | DBP Binding Energy | Binding Energy | Ratio of Binding Energy to Spurious |
|---|---|---|---|---|---|---|---|---|---|---|---|---|---|---|
| 1 | 64 | GAT GTG GGG AAC CAT GCC CAG GAT GAT | R Q Q2 | R I R | R H R | Q Q1 Q | E E Q1 | R Q3 R | E E Q | R R Q | R Q Q2 | 10264770 | 906033 | |
| 1 | 65 | ACT GTG GGC AAC AGT ACG GCA ATT ACC | Q N3 Q2 | R I R | R H R2 | Q Q1 Q | E H1 Q | Q E R | R R Q | Q Q Q | Q Q3 R2 | 10593486 | 512119 | |
| 1 | 66 | ACT GAC GAG CAT GAA GCT GAT GTC AAT | Q N3 Q2 | N N R | N N Q | E Q1 R | N N Q | R R Q2 | R D Q | R I Q3 | Q Q N Q3 | 31895100 | 3888784 | |
| 1 | 67 | GAC CCA GAA GTG CAG GCT GAC ATG AAG | R N Q3 | D E Q | R R Q | I I R | Q E R | N3 N3 R | R Q Q3 | R H R | R Q R | 14004360 | 495857 | |
| 1 | 68 | GAT CAT TAG CAA AGT GAG CAA CAC ACG | R Q Q2 | E E Q1 | I I R | E N R | H1 Q R | N R N | E N E | Q N E | Q E R | 21159954 | 2844809 | |
| 1 | 69 | GAT CGG AAG TAA GAC CCC CGA TAT GAC | R Q Q2 | H D Q | R Q Q | H I R | N Q R | E Q3 N3 | E H E | N I N | I N R | 8164692 | 708759 | |
| 1 | 70 | GGT GCT CGG CAT ACA GCC CTG ATT GTT | R H Q2 | R N3 N3 | E H R | E Q1 R | D D N3 | R Q3 R2 | E H Q | Q I R | R I Q3 | 4056912 | 706071 | |
| 1 | 71 | CAT GTC AGC ACT GCA CAG CAG CCG AAA | E Q1 Q2 | R I H1 | Q H1 R2 | N3 N3 Q | D D Q | Q Q R2 | E I N | E D R | N Q Q | 5930865 | 940863 | |
| 1 | 72 | GCT ACC GCT GTG CCT TCC GCT CCC | R N3 Q2 | N Q N3 | Q N3 R2 | Q N3 Q | I R N3 | N3 I R2 | R R N | E R N3 | E Q3 R2 | 10216521 | 637218 | |
| 1 | 73 | GAT CGT GAA GCT ACC TTT AGA GAC GCC | R Q Q2 | E H1 R2 | R N3 R2 | Q N3 Q | Q3 H1 Q2 | I N3 Q3 | N N N | R N N3 | R Q3 R2 | 11804220 | 440208 | |
| 1 | 74 | AAC GTT GCT GAG AGT CCT GGA ACG GGC | Q Q1 R2 | Q H1 Q2 | Q3 N N | N N R | H1 N H1 | N3 E N3 | Q N Q | N N3 N | H1 R R2 | 11792148 | 492924 | |
| 1 | 75 | GCT GAA GCC GAC TAT GCC GAT GAG | R N3 Q2 | N I Q3 | Q3 Q3 Q | R R R | N H1 Q3 | N3 H N3 | R E R2 | R E R | R N R | 9898740 | 835143 | |
| 1 | 76 | GAA TAA CAT TAG ACC GGG GCG CCA AAC | R N Q | N N Q | E D I | I I R | I N R | I E I | R R R | E E D | I Q1 Q | 9295611 | 466898 | |
| 1 | 77 | CAA TGC ACA GAC AAA TTC GAT ACT CAC | E N Q3 | H1 I1 H1 | I R2 Q | N N R | H1 N H1 | N3 I N3 | Q Q2 Q | N3 N3 N3 | N N E | 38166822 | 59410 | |
| 1 | 78 | No DBP possible | | | | | | | | | | | | |
| 1 | 79 | GCT AAT CAC GTC GAC GTC GGG CAT GGA | R N3 Q | N Q N | E N Q | I R E | N R N3 | R R I | R H R | E Q1 E | R R N | 9510655 | 945100 | |
| 1 | 80 | CCT GCC CAG GCC GCT GAG CTG GTG GGT | E N3 Q2 | Q3 R Q3 | N Q E | I Q3 Q3 | N3 R R2 | N R Q3 | E I D | R I R | R R H | 5592240 | 997835 | |
| 1 | 81 | ACC CAG GCA GTG CAG GAG CGA GCC AGG | Q Q3 Q3 | Q H E | R D Q | I I R | N N R2 | N R Q2 | E H D | R Q3 R2 | Q Q Q2 | 6631281 | 1211740 | |
| 1 | 82 | CCA GGG GCT CCC GCT CCC TGG GCA GAA | E N Q | R E Q | D R E | E Q3 D | E E R | Q E N3 | I H Q | R D Q | R N R | 4854492 | 1135027 | |
| 1 | 83 | GTG CCT CCG CAG CAA CCA CTA CAT | E Q1 Q2 | Q3 E H | I D R | E Q N3 | R E E | R E N | E D R | E I Q | E Q1 Q2 | 10134072 | 274029 | |
| 1 | 84 | CCT GAT GTA CAG TGG ACA GCG AAT | E N3 Q3 | R Q R | R I Q2 | E Q R | I H R | R Q R2 | I D Q | E R Q | Q N Q3 | 10593990 | 455091 | |

TABLE 4-continued

Scanning the complete S. Cerevisiae genome for conflicts – DBP's designed against the coding region of each gene

| Chromosome | Gene | Optimal DNA Sequence in Gene* | Zf1 Z1 | Zf1 Z2 | Zf1 Z3 | Zf2 Z1 | Zf2 Z2 | Zf2 Z3 | Zf3 Z1 | Zf3 Z2 | Zf3 Z3 | Zf4 Z1 | Zf4 Z2 | Zf4 Z3 | Zf5 Z1 | Zf5 Z2 | Zf5 Z3 | Zf6 Z1 | Zf6 Z2 | Zf6 Z3 | Zf7 Z1 | Zf7 Z2 | Zf7 Z3 | Zf8 Z1 | Zf8 Z2 | Zf8 Z3 | Zf9 Z1 | Zf9 Z2 | Zf9 Z3 | DBP Binding Energy | Binding Energy | Ratio of Binding Energy to Spurious |
|---|---|---|---|---|---|---|---|---|---|---|---|---|---|---|---|---|---|---|---|---|---|---|---|---|---|---|---|---|---|---|---|
| 1 | 85 | CCA ACG AAC GGT GCA CAG AAT ACG CAG | E | D | Q | Q | E | R | Q | E | Q1 | R | H | Q2 | R | D | Q | R | N | R | Q | N | Q3 | Q | E | R | E | Q | R | 16355520 | 526388 |
| 1 | 86 | GGT GAT CGC ACG CAA GCC TGC GGG GAA | R | H | Q2 | R | Q | Q2 | E | Q | H1 | R | E | R2 | R | E | R | N | Q3 | R2 | N | H1 | R2 | R | H | R | R | N | Q | 2939586 | 1473085 |
| 1 | 87 | GAG AAG CCA ACA AGC AAC GCT GAG GAA | R | N | R | Q | R | Q2 | E | D | Q | Q | D | R2 | Q | Q | Q | Q | Q1 | R2 | N1 | H1 | R2 | R | R | R | R | N | Q | 20535210 | 575100 |
| 1 | 88 | GAG GCG ACA TAA GTT GTT AGC ACA GCA | R | N | R | R | R | R | E | R | Q | Q | H | R2 | R | R | R | I | H | Q1 | H1 | Q2 | Q2 | R | D | Q | R | D | Q | 14004180 | 263582 |
| 1 | 89 | GAT CAT GGG CTA TGG GAT ACT CCC TAC | R | Q | Q | E | H | Q2 | R | H | R2 | E | H | R | H | R | R | R | R | Q3 | N3 | H1 | N3 | Q | E | Q3 | R | I | E | 5240610 | 432675 |
| 1 | 90 | AAG TTA GAT ACA CTT AAC GAA GCT AGT | Q | Q | R | I | I | Q | Q | E | Q3 | Q | I | Q2 | E | I | Q | R | Q | Q1 | Q | N | Q | Q | E | N3 | R | H1 | Q2 | 17980110 | 177343 |
| 1 | 91 | AAT GCT CCC AGG GGC TCG GCC AGG ACC | Q | N | Q3 | R | N3 | Q3 | E | Q3 | R2 | Q | Q | R2 | H1 | H1 | R2 | Q1 | D | R | R | Q3 | R2 | Q | N3 | R | Q | Q3 | R2 | 4905765 | 1462454 |
| 1 | 92 | GAT TCG CCA CGG CAC ACT CCG CAC AGA | R | Q | Q2 | D | H | R | E | D | Q | E | H | R | E | N | E | D | N3 | Q | E | D | R | E | N | E | E | N | Q | 2361600 | 1351886 |
| 1 | 93 | GCG GAG TGA GCC GCC CAG GCC AAC GAC | R | E | R | N | N | R | I | N | Q | R | Q3 | R2 | R2 | R2 | R2 | N | N | R | R | N | Q3 | Q | Q1 | Q | R | D | Q | 9558540 | 1111971 |
| 1 | 94 | ACA TCG CCG CCT ACC AGT CCC GCG GTG | Q | D | Q | D | I | Q | E | H | R2 | E | I | R | Q | R2 | Q2 | H1 | H1 | Q2 | Q | H1 | R2 | R | E | N3 | R | I | N | 3132513 | 1154321 |
| 1 | 95 | GGT ATC GCC AGT CTC CGG GTC CAT ACC | R | H | Q2 | I | N3 | R2 | R2 | R2 | Q3 | R2 | E | H1 | H1 | Q2 | R2 | N | R | R | I | R | R2 | E | Q | Q2 | R | R | Q2 | 4725558 | 561264 |
| 1 | 96 | ATC ACT CCC GGT CCA CAT TCT AGG AAG | Q | I | R2 | N3 | I | Q | R | Q3 | Q3 | Q | H1 | Q2 | E | H1 | Q2 | E | Q1 | Q2 | I | N3 | Q2 | E | E | R | R | Q3 | Q | 6605947 | 709280 |
| 1 | 97 | AAT GTC AGT TGT GAC GCT ACA CTT TTC | Q | Q3 | Q3 | R | I | R | E | Q | H1 | I | H1 | Q2 | I | I | Q2 | N3 | N3 | Q2 | N3 | Q | Q | Q | I | Q2 | Q | I | H | 8150676 | 162281 |
| 1 | 98 | AAT ACT GTA GCT GCT GAG ACG ATT ACC | Q | Q | Q | N3 | Q | N3 | Q | N | Q | R | I | Q2 | N3 | N3 | Q2 | N | N | Q | Q | E | Q | E | I | Q | Q | I | Q3 | 18607320 | 466494 |
| 1 | 99 | AGC TGT GGA AAC AAT CGC AGG GGA GAT | Q | H1 | R2 | I | H1 | Q2 | R | N | Q | Q | Q1 | Q2 | N | N3 | R2 | N | H1 | R2 | Q | H1 | R2 | R | N | Q | R | Q | Q2 | 19293534 | 242396 |
| 1 | 100 | GTA GAA ATC TGC TGC ACA TGC CAC ACG | Q | I | Q | R | N | Q | R | I | Q | Q1 | I1 | Q | N | H1 | Q | D | D | Q | Q | I1 | R2 | E | N | E | E | E | R | 9178908 | 103292 |
| 1 | 104 | GCT ACG GAG AAA CCG TGC ACT AAC TCT | R | N3 | Q3 | R | N3 | R | N | Q | R2 | R | R | R | E | D | R | I1 | H1 | R2 | N3 | N3 | Q2 | Q1 | Q1 | R2 | I1 | N3 | Q2 | 10532100 | 418624 |
| 1 | 105 | ACC GTT TCC AAG TCA TAC ACC ACT ACC | Q | Q3 | R2 | I | H1 | Q3 | R2 | Q3 | Q3 | H1 | Q2 | R2 | H1 | Q2 | R2 | H1 | N | Q | Q | N | E | Q | Q3 | R2 | Q | N3 | Q2 | 15664500 | 137917 |
| 1 | 107 | CTA TAT ATT TGT GGC AGA AAT CAT ACC | E | I | Q | I | H1 | Q3 | R2 | Q3 | I | H1 | Q2 | R2 | H1 | R | Q3 | Q | N | Q3 | Q | N | Q3 | E | Q1 | Q2 | Q | Q3 | R2 | 36455616 | 57145 |

TABLE 4-continued

Scanning the complete *S. Cerevisiae* genome for conflicts – DBP's designed against the coding region of each gene

| Chromosome | Gene | Optimal DNA Sequence in Gene* | Zf1 Z1 | Zf1 Z2 | Zf1 Z3 | Zf2 Z1 | Zf2 Z2 | Zf2 Z3 | Zf3 Z1 | Zf3 Z2 | Zf3 Z3 | Zf4 Z1 | Zf4 Z2 | Zf4 Z3 | Zf5 Z1 | Zf5 Z2 | Zf5 Z3 | Zf6 Z1 | Zf6 Z2 | Zf6 Z3 | Zf7 Z1 | Zf7 Z2 | Zf7 Z3 | Zf8 Z1 | Zf8 Z2 | Zf8 Z3 | Zf9 Z1 | Zf9 Z2 | Zf9 Z3 | DBP | Binding Energy | Ratio of Binding Energy to Spurious |
|---|---|---|---|---|---|---|---|---|---|---|---|---|---|---|---|---|---|---|---|---|---|---|---|---|---|---|---|---|---|---|---|---|
| 1 | 108 | TAT CAT GAC AAC ATG GTA CAA ATT GAG | I | N | Q3 | E | Q1 | Q2 | R | N | Q3 | Q | Q1 | R2 | Q | I | R | R | R | R | Q | E | N | Q3 | Q | I | Q3 | R | N | R | 25006833 | 153077 |
| 1 | 109 | AAG ACC GCA CTA GAT CTT ACC AAG AGC | Q | Q | R | Q | Q3 | R2 | R | D | Q | E | I | Q | R | Q | Q2 | E | I | R | Q2 | Q | Q3 | R2 | Q | Q | R | Q | H1 | R2 | 13895100 | 382466 |
| 1 | 110 | ATG ACG ACA TCC AAG CCA GCT TTT ACC | Q | I | R | Q | E | Q | Q | D | Q | I | Q3 | R2 | Q | Q | R | E | D | Q | R | N3 | Q2 | I | I | Q3 | Q | Q3 | N | R2 | 16928244 | 147676 |

*The optimal DNA sequences in genes 1–61 are shown as SEQ ID NOS: 5–65, respectively, in the Sequence Listing. The sequences in genes 62 and 63 are identical and shown as SEQ ID NO: 66. The sequences in genes 64–77 are shown as SEQ ID NOS: 67–80, respectively. The sequences in genes 79–100 are shown as SEQ ID NOS: 81–102, respectively. The sequences in genes 104 and 105 are shown as SEQ ID NOS: 103 and 104, respectively. The sequences in genes 107–110 are shown as SEQ ID NOS: 105–108 respectively.

TABLE 5

Scanning the complete *C. elegans* for conflicts – DBP's designed against the coding region of each gene

| Chromosome | Gene | Optimal DNA Sequence in Gene* | Zf1 Z1 | Zf1 Z2 | Zf1 Z3 | Zf2 Z1 | Zf2 Z2 | Zf2 Z3 | Zf3 Z1 | Zf3 Z2 | Zf3 Z3 | Zf4 Z1 | Zf4 Z2 | Zf4 Z3 | Zf5 Z1 | Zf5 Z2 | Zf5 Z3 | Zf6 Z1 | Zf6 Z2 | Zf6 Z3 | Zf7 Z1 | Zf7 Z2 | Zf7 Z3 | Zf8 Z1 | Zf8 Z2 | Zf8 Z3 | Zf9 Z1 | Zf9 Z2 | Zf9 Z3 | DBP Binding Energy | Ratio of Binding Energy to Spurious Binding Energy |
|---|---|---|---|---|---|---|---|---|---|---|---|---|---|---|---|---|---|---|---|---|---|---|---|---|---|---|---|---|---|---|---|
| 1 | 1 | ACC AAG CCG CCC GAC TCC TAG GAG ATG | Q | E | R | Q | Q | R | E | D | R | E | Q3 | R2 | R | N | Q3 | I | Q3 | R2 | I | N | R | R | N | R | Q | I | R | 23846400 | 183458 |
| 1 | 3 | GAG GCC CAC GAG CAC CAC AGG AGC GAA | R | N | Q3 | R | Q3 | R2 | R | R | N | E | N | E | R | N | N | E | R | E | Q | Q | R | Q | H1 | R | R | N | Q | 58257900 | 162173 |
| 1 | 4 | GAC AAT TCT CCC GGC GCC AAT GAT CAC | R | N | Q3 | N | Q | R2 | I1 | N3 | N | E | N | Q3 | R | H1 | N | E | Q3 | R2 | Q | N | R | R | Q | R2 | Q | N | E | 83021040 | 99575 |
| 1 | 5 | AGC ACG ACT CGG CAC ACC CGT TCC GCC | Q | H1 | R2 | H1 | E | Q | R | Q | I1 | H | H1 | H | E | H1 | H1 | E | H1 | R2 | E | H | H | I | Q | Q2 | I | Q3 | E | 25095960 | 177149 |
| 1 | 6 | CCA GGA AGG CGC ACT GGC AGA CGT AAG | E | D | Q | R | E | R2 | E | Q | R2 | E | H1 | H | N | E | N | Q | R | R2 | Q | N | R | E | H | R2 | Q3 | Q | R2 | 34627332 | 148563 |
| 1 | 7 | CCT ATT ACT CGT GGT GCC GCG GGA GCC | R | N3 | Q3 | Q | N | R | Q | Q | N | E | H1 | H | R | H | Q3 | R | R | Q2 | R | Q | Q | R | Q | H | Q | Q | R | 32769390 | 208126 |
| 1 | 8 | AAT AGC GAA CAG ATA TCT GAC AAC TCC | Q | N | N | R | Q3 | Q3 | Q | N | Q | E | Q | R | H | I | Q | I1 | N3 | Q2 | N | Q3 | R2 | Q | Q1 | R2 | I | Q3 | R2 | 85891770 | 58952 |
| 1 | 9 | GTC GCG CAT ACT CGC TTT AAT | R | I | R2 | E | R | R | E | Q1 | H1 | Q | N3 | Q2 | Q | H1 | H1 | R | N3 | H1 | H1 | H1 | R2 | I | I | Q3 | Q | N | Q3 | 22607199 | 144807 |
| 1 | 10 | GAT ATT CGC GAT GGC AGC GGT GAC GAT | R | Q | Q2 | Q | I | Q | E | H1 | I | R | R2 | R | R | H1 | Q | R | H1 | Q2 | R | H | Q2 | R | Q | I | N | Q | Q2 | 35024550 | 200334 |
| 1 | 11 | CAT AAC GTC GAG GCT GCC CGC AAG GAG | E | Q1 | Q2 | Q1 | Q | Q2 | R | E | H1 | E | N | R2 | R | N3 | H1 | N3 | Q3 | R2 | E | N | R2 | Q | I | R | E | Q3 | R | 26896050 | 338100 |
| 1 | 12 | ACC AGC CAT CAC GCC ATG AGC ACC | Q | Q3 | R2 | H1 | Q1 | R2 | E | H1 | I | H | R2 | R2 | Q | Q3 | R2 | Q | H1 | I | E | Q | Q | R | I | Q3 | Q3 | Q3 | R2 | 35287740 | 156180 |
| 1 | 13 | AGG CAC CCC GGG AAG CGC CGG ACC GAA | R | Q3 | Q | Q | H1 | N | E | Q3 | D | E | N | H | R | R | N3 | R | H1 | H1 | E | H | H | E | R | Q | R | N | Q | 14482326 | 394684 |
| 1 | 14 | GGA GCA CCA GAC GCC CTA CTC GCG ACT AAG CCG | R | N | Q | R | Q | R2 | R | E | H1 | R | H | Q2 | R | R | R | E | D | R | N3 | Q | Q | D | I | I | E | D | R | 37857024 | 21565 |
| 1 | 15 | GAT GCT CGC GAT GCC CGC ACC AAG CCA AGA | Q | Q3 | Q | Q | Q3 | Q1 | E | E | Q3 | E | Q3 | Q3 | R | Q3 | Q3 | R | R2 | R2 | Q | R | R2 | Q | Q | Q3 | Q | N | Q | 20671398 | 146603 |
| 1 | 16 | AGA GCC GAT GCC CGC AAG GCT GCT | R | Q3 | Q2 | N3 | H1 | R2 | R | H1 | Q | Q3 | Q3 | H1 | Q3 | Q3 | H1 | R2 | R2 | Q3 | R2 | R | R2 | N3 | N3 | Q3 | N3 | Q2 | Q2 | 44071200 | 294768 |
| 1 | 17 | ACA GAC GAG GCC AAG ATC TAC GCC GAA | Q | Q | Q | Q | Q3 | R2 | R | R | Q | Q | R | R | Q | Q | Q | Q | Q | R | R | N | E | R | Q3 | Q2 | R | H1 | N | 4248410 | 155670 |
| 1 | 18 | CCA CAC GGT AGG CCG ATA GGT ACT CGC | E | D | D | Q3 | R2 | Q2 | E | H1 | H | Q3 | Q3 | Q2 | E | D | H | R2 | E | H | R | Q | Q2 | E | Q3 | H1 | E | Q | R2 | 21033604 | 160124 |
| 1 | 19 | CCT ACA AGG CCC CGT AGG AGG GCC GAT | E | N3 | Q3 | Q3 | D | Q | Q | H | R2 | E | Q3 | R | H | H | E | E | H1 | H1 | H | Q | R | R | Q3 | Q3 | H1 | Q | Q2 | 15698286 | 488647 |
| 1 | 20 | ACC AAC GGA CAG GAT GGC GCC GAA CAA | Q | Q3 | R2 | Q1 | Q1 | R2 | N | H1 | Q | Q3 | R2 | Q2 | Q | H1 | Q2 | H1 | Q2 | Q3 | Q3 | R2 | R | N | Q | R | Q | N | Q3 | 60312960 | 198256 |
| 1 | 21 | GCA AGC CGC TAT GTC GAC GCT CAA | R | D | Q | H1 | E | R2 | R | E | H1 | Q | Q2 | R2 | I | R | N | N | R2 | N3 | N3 | Q2 | N3 | E | H1 | R2 | E | N | Q3 | 22049052 | 158783 |
| 1 | 22 | AGT CCG CCT AAG CGC GTT CCG CCG | Q | H1 | Q2 | E | D | R | E | N3 | E | Q | N3 | Q2 | E | H1 | E | N3 | E | I | I | Q3 | Q2 | E | E | D | E | D | R | 13743972 | 254069 |

TABLE 5-continued

Scanning the complete C. elegans for conflicts – DBP's designed against the coding region of each gene

| Chromosome | Gene | Optimal DNA Sequence in Gene* | Zf1 Z1 | Zf1 Z2 | Zf1 Z3 | Zf2 Z1 | Zf2 Z2 | Zf2 Z3 | Zf3 Z1 | Zf3 Z2 | Zf3 Z3 | Zf4 Z1 | Zf4 Z2 | Zf4 Z3 | Zf5 Z1 | Zf5 Z2 | Zf5 Z3 | Zf6 Z1 | Zf6 Z2 | Zf6 Z3 | Zf7 Z1 | Zf7 Z2 | Zf7 Z3 | Zf8 Z1 | Zf8 Z2 | Zf8 Z3 | Zf9 Z1 | Zf9 Z2 | Zf9 Z3 | DBP Binding Energy | Ratio of Binding Energy to Spurious Binding Energy |
|---|---|---|---|---|---|---|---|---|---|---|---|---|---|---|---|---|---|---|---|---|---|---|---|---|---|---|---|---|---|---|---|
| 1 | 23 | AAG CCG ATC GCT GCG ACC GAA CCG CCT | Q | Q | R | E | H | R | H | Q | I | N3 | R | R2 | E | E | R | Q | Q3 | R2 | R | N | Q | E | D | R | E | N3 | Q2 | 2560293 | 0 255727 |
| 1 | 24 | AAT GAT CTA GCT CCC AGT CCT ACT GCG | Q | N | Q3 | R | Q | Q2 | E | Q | I | N3 | Q | Q3 | E | Q3 | H | H1 | H1 | Q2 | E | N3 | Q | Q | N3 | Q2 | E | E | R | 3972037 | 5 180624 |
| 1 | 25 | CAG AGG ACT CGC CGT ATC GTC GCT GGT | E | Q | R | R | Q | Q | I | H1 | R2 | H1 | E | R | H | H | R2 | I | I | R2 | R | I | R2 | R | R | Q2 | R | H | R | 2013186 | 173906 |
| 1 | 26 | GCT ATG AGG TCA CGG GCT CCC CCT GAT | R | N3 | Q3 | Q | Q | Q2 | Q | D | Q | D | Q3 | R2 | H | Q | R2 | D | N3 | R2 | E | Q3 | R2 | E | N3 | Q2 | R | Q | Q2 | 2813218 | 193724 |
| 1 | 27 | GAC ACA GGT CCC CAT CAC GGG ACA AGT | R | N | Q3 | Q | D | Q | R | H | H | Q3 | Q | R | Q1 | E | R | E | N | E | H | R | R2 | Q | D | Q | Q | H1 | Q2 | 3161386 | 8 189117 |
| 1 | 28 | CAC GTT GGG ACC GCC AGG AGC CCG AAT | E | N | E | I | R | Q3 | H | H | R | Q3 | Q3 | R | Q3 | R | R2 | N | Q | H1 | H1 | H1 | R | D | R | R | Q | N | Q3 | 3004155 | 0 183454 |
| 1 | 29 | CGA GAA CGT CCC ATC AAG CGT GAA CAC | E | N | Q | R | N | Q | E | H | Q | E | Q3 | R2 | I | E | R | Q | Q | R | H | Q2 | Q2 | R | N | Q | E | N | E | 3908010 | 6 109209 |
| 1 | 30 | GAT CCT TCG AGT ACG CCT ACG CAA GGA | R | Q | Q2 | E | N3 | N3 | I | D | R | Q | H1 | R | E | Q3 | N3 | E | N3 | R | E | H1 | Q2 | E | E | R | N | R | Q | 3593435 | 4 145548 |
| 1 | 31 | AAC GCC GCC TAG ACC CCG GGG AAT ACC | Q | Q1 | R2 | R | R | Q3 | Q3 | I | N | R | I | N | Q3 | R | R2 | D | R | R | R | R | R | Q | N | Q3 | Q | Q3 | R2 | 2422728 | 0 379135 |
| 1 | 33 | GTG GTG CAG GAG GGG GAG GAG GCC ACA | Q | H | R | R | I | H | E | R | E | R | R | Q2 | H | H | Q | Q | E | R | Q | H | R | R | R | R2 | R | H | Q | 3559901 | 4 164587 |
| 1 | 34 | CGT ACA AGG AAT ACC CTG AAG GAC AAC | E | H | Q2 | D | H | Q | Q | Q | Q | Q | R | E | R | Q3 | H | I | H | R | Q | Q | R | R | N | R2 | Q | Q1 | R2 | 981702 | 18 71458 |
| 1 | 35 | ACC TCC ACT CAG CCA CCG GCG GCG CCA | Q | Q3 | R2 | Q | Q3 | R2 | Q | N3 | Q | Q | E | Q | Q | Q3 | Q3 | D | D | R2 | D | Q3 | R2 | R | N | Q3 | E | D | Q | 3690198 | 0 123875 |
| 1 | 36 | AAA GCG GTA CAA GCG ACC CGT GCT GCT | R | N | Q | R | E | R | R | I | E | E | H1 | N | N | R | E | R | E | R | Q | Q3 | R2 | R | E | R | D | E | Q | 2423269 | 8 227970 |
| 1 | 37 | ACA ACG ACC GAG GAG CCT ACC GAA GCC | Q | D | Q3 | Q | Q | E | Q | Q3 | I | N | R | Q3 | D | Q | Q | E | E | Q | Q3 | Q | R | E | H | Q2 | R | N3 | Q3 | 4972320 | 0 288576 |
| 1 | 38 | GAG AAC CGT CCC CAC CCG AAG CTG GCT | R | N | R | R | N | R | E | H | Q3 | E | E | Q2 | R | E | R | Q | D | R | R | Q | R | R | N | R2 | R | N3 | Q2 | 2538169 | 2 196538 |
| 1 | 39 | CGT CCG GTG CCC GAG ACT GGG ACC GGT | E | H | Q2 | R | R | Q3 | Q | N | H | Q3 | E | R2 | H | E | R2 | R | N3 | Q2 | R | Q | R | E | D | R2 | R | N3 | Q3 | 2296398 | 201668 |
| 1 | 40 | AGG GAC CGT ACG GAG CAG GAC CCC CCT | Q | Q | R | Q | H | R2 | E | Q3 | I | E | Q3 | Q2 | N | Q | Q | Q | Q | R | R | N | R | Q | E | Q3 | E | N3 | Q2 | 2985255 | 0 285512 |
| 1 | 41 | AGG CAA CCC TGG AGG CGT CCC AGC ACC | Q | Q | R | E | R | Q3 | E | Q3 | H | H | H | Q2 | D | Q | Q2 | H | H | Q2 | E | Q3 | R2 | H | Q3 | R2 | R | Q | Q3 | 1637136 | 9 231386 |
| 1 | 42 | CTC ACT ACC CCG GCA CCA AGG ACC AGT | E | I | Q | R2 | Q | Q3 | Q3 | I | R2 | E | E | D | R | D | Q | D | D | R | Q | Q | Q | Q | Q | R2 | Q | H1 | Q2 | 2376815 | 4 214650 |
| 1 | 43 | GAC GAG CAC CTA AAG ACC GCC ACT CCG | R | N | Q3 | N | N | Q2 | N | E | E | E | E | D | Q | Q | E | Q3 | Q3 | R2 | R | R | R | N3 | N3 | R2 | E | D | R | 3214836 | 0 235106 |
| 1 | 44 | CCC GTC GGG TAG ACG GCG GTT ACC GCC | E | Q3 | R2 | R | I | R2 | R | H | R | I | N | R | E | Q | Q | R | E | R | R | R | R2 | Q | Q3 | R2 | R | H1 | R2 | 1567811 | 7 218000 |

TABLE 5-continued

Scanning the complete *C. elegans* for conflicts – DBP's designed against the coding region of each gene

| Chrom-osome | Gene | Optimal DNA Sequence in Gene* | Specific Amino Acids in DBP | | | | | | | | | | | | | | | | | | | | | | | | | DBP Binding Energy | Ratio of Binding Energy to Spurious Binding Energy |
|---|---|---|---|---|---|---|---|---|---|---|---|---|---|---|---|---|---|---|---|---|---|---|---|---|---|---|---|---|---|
| | | | Zf1 | | | Zf2 | | | Zf3 | | | Zf4 | | | Zf5 | | | Zf6 | | | Zf7 | | | Zf8 | | | Zf9 | | | | |
| | | | Z1 | Z2 | Z3 | Z1 | Z2 | Z3 | Z1 | Z2 | Z3 | Z1 | Z2 | Z3 | Z1 | Z2 | Z3 | Z1 | Z2 | Z3 | Z1 | Z2 | Z3 | Z1 | Z2 | Z3 | Z1 | Z2 | Z3 | | |
| 1 | 45 | AGG CCA GGG GCC CCC TAC GCC CCA ACA | Q | Q | R | E | D | Q | R | H | R | R | R | Q3 | E | Q3 | R2 | I | N | E | R | Q3 | R2 | E | D | Q | Q | Q | Q | 12322980 | 331208 |
| 1 | 46 | CAA GCT CCC GTA ACA CAA CCC CGG AGA | E | N | Q3 | R | R | R | E | Q3 | R2 | R | I | Q | Q | D | Q | E | N | Q3 | E | E | R2 | E | H | R | Q | R | Q | 29693385 | 180837 |
| 1 | 47 | CCC GGG GCC CCT CCG GCG GAC GAT | E | Q3 | R2 | R | R | R2 | H1 | R | R2 | Q3 | I | Q | R2 | Q | D | E | E | Q3 | R | E | R2 | E | H | R | Q | R | Q2 | 21161601 | 339032 |
| 1 | 48 | ACT GCC CAA ATC AAG GCC CCG AGA CAT | Q | N3 | Q2 | H | Q3 | R2 | E | N | Q3 | E | H | R2 | E | N3 | Q | R | E | D | Q | R | R2 | R | N | E | E | Q1 | Q2 | 57865212 | 138864 |
| 1 | 49 | ACT ACT CCC ACG CGG ACA CCC AAC | Q | N3 | Q2 | N3 | Q3 | R2 | E | N | Q3 | Q | I | R | Q | Q | N3 | Q | H | R | Q | D | Q | E | N | Q | Q | Q1 | R2 | 30357018 | 228773 |
| 1 | 50 | ATC GAC CCG CAT GCG CTG GCG CAG ACG | Q | I | R2 | N | R | Q3 | E | D | R | E | Q1 | Q2 | E | H | R | H | I | R | R | E | R | Q | R | Q | E | E | R | 17484525 | 223352 |
| 1 | 51 | AGT ACC GCG GAT CAG GCG GCG TCC GTA | Q | H1 | Q2 | Q | Q3 | R2 | E | E | H | R | Q | Q2 | E | Q | E | E | E | R | R | E | R | Q3 | Q | R2 | R | I | Q | 19081170 | 276357 |
| 1 | 52 | GCA GCT CAA GGC GAC AAC GCC GAA | R | D | Q | R | N3 | Q3 | E | N | Q3 | R | D | Q | R | H1 | Q | N | H1 | Q3 | R | Q1 | R2 | R | I | Q3 | R | N | Q | 70750890 | 169007 |
| 1 | 53 | GTG ACC GAC ACG CCC AGT AAG TCG GGA | R | I | R | Q | Q | R | R | H1 | Q3 | Q | I | R2 | R | E | Q3 | H1 | Q | Q2 | Q | R | I | R | D | R | R | N | Q | 24010695 | 209162 |
| 1 | 54 | GAC CTG GCG GCC CTC TGC GCC GCT GAA | R | N | Q3 | E | I | R | E | N | Q3 | R | R2 | R | R | Q3 | R | Q3 | R | Q2 | H1 | Q2 | R2 | I | H1 | Q | R | N | R | 28604262 | 232239 |
| 1 | 55 | ACC GCC GAG CTC TGC GCT GAA | Q | Q3 | R2 | R | Q3 | R2 | Q3 | R2 | R | R2 | R | N | E | R | D | H1 | R | R2 | H1 | R2 | R2 | R | N3 | Q2 | R | E | N | Q | 70547100 | 74401 |
| 1 | 56 | AAA GAC CGC AAA GCA ACG GGG ACG CAA GAT | R | N | Q3 | N | R | Q3 | E | N | Q3 | R | N | R2 | R | H | Q | R | E | N3 | E | R | Q3 | R | E | N | Q3 | R | Q | Q2 | 35291445 | 172547 |
| 1 | 57 | CCT ACG GCG CTA GAC AGG ACT CCG CAG | E | N3 | Q3 | Q | E | R | R | Q | Q2 | E | E | Q2 | Q | Q3 | R2 | R | Q | N3 | E | D | R | E | D | R | E | Q | R | 19909656 | 280252 |
| 1 | 58 | AGA GCG GAC CGC ACG GCA CGG AAT | Q | N | Q | N | Q3 | R2 | E | E | H1 | R | E | D | Q | Q3 | R2 | Q | N3 | E | E | H1 | R2 | E | N | D | R | E | Q | R | 23780730 | 194692 |
| 1 | 59 | GGA CGT CGC GCA GAC ACC GCC CAA AGA | R | N | Q | E | H | Q3 | R | R | R2 | R | R2 | R | N | R | Q3 | R | Q3 | R2 | R | E | R | R | Q | Q3 | Q | R | Q | 34512156 | 201230 |
| 1 | 60 | AAT CAG GGT CGC GCA GAG GGT GAA GCT | R | N | Q | E | Q | R | Q | D | Q2 | R | D | Q | E | D | R | R | R2 | R | R | E | R | E | N | Q | R | N3 | Q2 | 58798980 | 120510 |
| 1 | 61 | CAA CAT CGT CCC GGC GAC ACC GAC GAC | E | N | Q3 | E | Q1 | Q2 | E | E | H | R | E | Q3 | R | H | Q | R | H | Q3 | R | Q3 | R2 | R | N | E | R | R | Q3 | 43500744 | 201578 |
| 1 | 62 | GGA GCC CGT GCG GAT CCG CGC TAA | E | N | Q3 | R | Q3 | R2 | E | E | H | E | Q3 | R2 | R | R | H1 | N3 | Q | N3 | Q3 | D | Q2 | R | E | H1 | R2 | I | N | Q | 18935478 | 228209 |
| 1 | 63 | GCC ACT CAG GCA GCA ACT CAG GCA GCC | R | Q3 | R2 | N3 | Q3 | R2 | E | E | H1 | E | D | Q3 | R | D | Q3 | R | R | Q | E | R | R | R | E | R | Q | Q3 | R2 | 49245408 | 236014 |
| 1 | 64 | CCA AAT GGT CAA GCC GGG GCA AAC | E | D | Q | N3 | Q3 | R2 | E | H | H1 | N | Q3 | R2 | R | N | H1 | R | N | N | R | Q3 | R2 | R | N | D | Q | Q | Q1 | R2 | 72475200 | 122212 |
| 1 | 65 | CCA ATG GCC ATC GAC GCC GCG ACC ACA | E | D | Q | Q | I | Q | R | R | R2 | R | I | R2 | Q | N | R2 | R | E | R | R | E | R | R | Q | Q3 | R2 | Q | D | Q | 40564530 | 138662 |

TABLE 5-continued

Scanning the complete *C. elegans* for conflicts – DBP's designed against the coding region of each gene

| Chromosome | Gene | Optimal DNA Sequence in Gene* | Zf1 Z1 | Z2 | Z3 | Zf2 Z1 | Z2 | Z3 | Zf3 Z1 | Z2 | Z3 | Zf4 Z1 | Z2 | Z3 | Zf5 Z1 | Z2 | Z3 | Zf6 Z1 | Z2 | Z3 | Zf7 Z1 | Z2 | Z3 | Zf8 Z1 | Z2 | Z3 | Zf9 Z1 | Z2 | Z3 | DBP Binding Energy | Ratio of Binding Energy to Spurious Binding Energy |
|---|---|---|---|---|---|---|---|---|---|---|---|---|---|---|---|---|---|---|---|---|---|---|---|---|---|---|---|---|---|---|---|
| 1 | 66 | GAC CGT CAG GAT CGC GAT TAC CGG CCA | R | N | Q3 | E | H | Q2 | E | Q | R | R | Q | Q | E | H1 | Q | R | R | Q2 | I | N | E | E | H | R | E | D | Q | 18477492 | 161318 |
| 1 | 67 | ACA GCG GCA GCT ACT ACC TCT CCC GAA | Q | D | Q | R | E | R | R | D | Q | Q | N3 | R2 | N3 | Q | Q3 | H | Q | R2 | I1 | N3 | Q | E | Q3 | R2 | R | N | Q | 57290895 | 157788 |
| 1 | 68 | GCC CCA ACC ACG GGG AGG GCT AGG | R | Q3 | Q | E | Q | R | R | D | Q | R | N3 | R2 | E | R | Q | R | H | R | N3 | Q | R2 | E | N3 | Q2 | R | Q | R | 29386800 | 292966 |
| 1 | 69 | AAC AAC AGG CCA GCT GGA GGG AAT ACT | Q | Q1 | R2 | E | Q1 | R2 | Q | H1 | R2 | E | D | Q3 | E | N3 | R2 | H | N | R2 | R | Q | R2 | R | N3 | Q3 | E | N3 | Q2 | 66919320 | 158830 |
| 1 | 70 | AAC GCG AGC GGA ACC TAA CCG ACG CAA | Q | Q1 | R2 | R | R | E | E | Q | H1 | R | N | Q | N | Q | Q | E | D | R | D | E | Q | R | E | R | E | N | Q3 | 24375168 | 247241 |
| 1 | 71 | GCA CGC AAC GCT GCA CGC GCA GCA | R | D | Q | E | E | R | E | R | Q | R | D | R2 | R | H | R | H | I | R | H | Q3 | R | R | E | R2 | E | N | Q3 | 28378485 | 203936 |
| 1 | 72 | AAT CCG CCC TAC ATC GGT CCC CAA | Q | N | Q3 | E | I | Q3 | Q | Q1 | R2 | Q | N3 | R2 | R | I | N | H | H | R | E | Q | R2 | R | Q3 | E | R | N | Q3 | 20305869 | 158287 |
| 1 | 73 | GAG GTT CGG GCT TCA GGG CAG GCG GCC | R | N | R | R | I | Q3 | E | Q3 | R2 | E | R | R | D | R | R | H | R | R | N3 | H1 | E | R | E | R | I | Q | 21672135 | 188818 |
| 1 | 74 | AAG CAG GCG CAA GGT AGG CCT GGG CTA | Q | Q | R | E | Q | R | R | H | E | R | E | E | Q | H | Q2 | Q | R | N3 | Q1 | Q2 | R | R | N3 | Q | R | N | R | 36050427 | 156722 |
| 1 | 75 | CAG ACA GTA GCC TCT GCG CAT GAG GAG | E | Q | R | R | E | Q | R | I | Q | R | E | R | R | I1 | N3 | Q | E | R | E | Q1 | Q2 | R | Q3 | N3 | R | N3 | Q2 | 29855007 | 211953 |
| 1 | 76 | GCC CCC GAC CAA CTC AGG GCC ACC GCT | R | Q3 | R2 | E | Q3 | N | R | N | R | E | R | Q3 | H | N3 | Q2 | Q | R | N3 | Q3 | R2 | R | Q3 | Q1 | R2 | Q | N | Q | 31503762 | 273280 |
| 1 | 77 | GCT GTA GCC CTG AAG GCT AAC AGA | R | N3 | Q2 | N | R | R | R | Q3 | E | N | R | E | H | I | E | R | N3 | H1 | R2 | E | N | Q3 | R | N | E | N | Q | 32961060 | 158008 |
| 1 | 78 | GGC GAG ACG GCA CCA CGC CAA CGA | R | H1 | R2 | R | I | R | N | R | Q3 | R | Q3 | H | Q2 | E | Q | R | Q2 | I | N | R | I | D | R | Q | N | Q | 30399876 | 184607 |
| 1 | 79 | ACA AGC CAC GCT CCC GGT TAG TCG AGA | Q | D | Q | D | Q | D | Q | Q3 | R | N3 | E | R | Q1 | Q2 | Q2 | H | Q | Q2 | R | I | R | R | Q1 | R | N | E | Q1 | Q2 | 22475286 | 148967 |
| 1 | 80 | GAG CAA ACC GTG GCC ACG TTG AAC CAT | E | N | R | R | E | H1 | R | I | E | R | H1 | Q2 | H1 | R2 | R | R | R2 | E | E | R | R | E | R | R | N | Q | 50369850 | 79964 |
| 1 | 81 | CCA AAC CTT ACA AGC CGT GCT GAG GAA | R | D | Q | R | Q | E | I | R2 | Q | D | I | R | D | N3 | Q3 | E | R2 | N | H1 | R2 | R | D | Q1 | R | R | N | Q | 42618420 | 109734 |
| 1 | 82 | ACT GCT GGT GCA CCG AAG GAA GAC AAG | Q | N3 | Q2 | R | N3 | Q | H | N3 | Q2 | D | Q3 | H1 | D | R | R | E | Q3 | R | Q | R | Q2 | Q | Q3 | R2 | 99399690 | 118811 |
| 1 | 83 | CTC CCA AGT GCG TCT GAT CCC GAT ACC | E | I | R2 | E | D | Q | Q2 | I | Q2 | E | I1 | N3 | I1 | N3 | Q2 | I | N | R | R | Q | H1 | R2 | 30293190 | 147363 |
| 1 | 84 | CAT GTA GGA AGT AAC GTC GCC CAT GGC | E | Q1 | Q2 | R | I | Q | N | Q | H1 | Q2 | Q1 | Q2 | Q1 | Q2 | Q3 | E | D | Q | R | Q | E | I | R | H1 | E | 29013138 | 168290 |
| 1 | 85 | GAA AAG GGC GAC GCC ACC CCA CTG CAC | E | N | Q | R | Q | Q | R | H1 | R2 | N | H1 | R2 | Q3 | R | Q3 | R | E | R2 | E | Q3 | R | N3 | Q2 | E | N | Q | 49253563 | 127883 |
| 1 | 86 | ACT CGG GGC GTG CTC AGG ACT AGA | Q | N3 | Q2 | E | H | R | H1 | R2 | H | Q2 | I | R | E | N | E | R | R2 | E | Q3 | R2 | N | R | Q3 | 22559176 | 151162 |

TABLE 5-continued

Scanning the complete *C. elegans* for conflicts – DBP's designed against the coding region of each gene

| Chromosome | Gene | Optimal DNA sequence in Gene* | Zf1 Z1 | Zf1 Z2 | Zf1 Z3 | Zf2 Z1 | Zf2 Z2 | Zf2 Z3 | Zf3 Z1 | Zf3 Z2 | Zf3 Z3 | Zf4 Z1 | Zf4 Z2 | Zf4 Z3 | Zf5 Z1 | Zf5 Z2 | Zf5 Z3 | Zf6 Z1 | Zf6 Z2 | Zf6 Z3 | Zf7 Z1 | Zf7 Z2 | Zf7 Z3 | Zf8 Z1 | Zf8 Z2 | Zf8 Z3 | Zf9 Z1 | Zf9 Z2 | Zf9 Z3 | DBP Binding Energy | Ratio of Binding Energy to Spurious Binding Energy |
|---|---|---|---|---|---|---|---|---|---|---|---|---|---|---|---|---|---|---|---|---|---|---|---|---|---|---|---|---|---|---|---|
| 1 | 87 | ACA CGC CAG ACG GCC CAC GCC CCC AAT | Q | D | Q | H1 | E | R2 | E | Q | R | E | Q | R | R | R | Q3 | I1 | H1 | R2 | R | Q | Q2 | E | Q1 | Q2 | R | N3 | Q2 | 22770018 | 332728 |
| 1 | 88 | AAT GGT GCT TAT GTC TGC GAT CAT GCT | Q | N | Q3 | R | H | Q2 | Q | N3 | Q2 | N | I | Q2 | I | R2 | R2 | R | H | Q2 | E | H | R | Q | I | Q3 | Q | E | R | 36599346 | 105408 |
| 1 | 89 | ACA TAT ACG GAC GGG GGT CGG ATT ACG | Q | D | Q | H | N | Q3 | E | R | Q3 | R | N | Q3 | H | I | R | I | H | R | E | N3 | R | Q | Q | R | R | N | Q3 | 21505752 | 166494 |
| 1 | 90 | GAT CAT AAC CCG GGT TGG CCT AAG GAC | R | Q | Q2 | E | Q1 | Q2 | Q | Q | Q1 | E | D | R2 | H | H | R | H | D | Q | E | Q | R | E | N3 | Q2 | R | Q1 | R2 | 21718140 | 261012 |
| 1 | 91 | GAT CAG GCC GTT AAG ACA CAG CCT AAC | R | Q | Q2 | E | 1 | R | R | Q3 | R2 | R | I | Q3 | Q | Q | R | D | Q | R2 | N3 | Q | Q2 | R | Q | Q2 | Q | N3 | Q2 | 30361419 | 297740 |
| 1 | 92 | AAT GCA ACG GAT GCT CCC GCT GAT GCT | Q | N | Q3 | R | D | Q3 | Q | E | R | R | Q | R | N3 | Q | Q | E | Q3 | R2 | R | N3 | R | R | N | R | Q | I | R | 68828940 | 208472 |
| 1 | 93 | GAT CCT ATC GGT GAT ATC AGG GAG ATG | R | Q | Q2 | E | N3 | Q2 | I | Q | R2 | H | Q | R2 | Q | I | Q2 | I | N | Q | Q | H | R | N | I | Q3 | E | E | R | 41422185 | 110016 |
| 1 | 94 | CAC TCT GAG GTC GGA TAA GGG AAT ACG | E | N | E | I1 | N3 | Q2 | N | H1 | R2 | I | R | R | N | N3 | Q | E | E | R | R | I | Q3 | Q | N | Q | E | E | R | 32161923 | 113354 |
| 1 | 95 | GCT CCC AGC GCA GCT GCG TCC GGA GCG | R | N3 | R | Q3 | E | R2 | H1 | N | Q3 | R | D | Q | R | Q2 | Q2 | E | N | R | R | D | Q | Q | I | R | Q | D | Q | 23772042 | 285203 |
| 1 | 96 | GAT GGT CCC TAC GCA ATG ACA | R | Q | Q2 | E | H | Q2 | Q3 | E | R2 | R | H | R | E | N3 | N3 | E | D | R | E | H1 | R2 | R | N | R | Q | Q | Q2 | 23602050 | 141855 |
| 1 | 97 | GAG ATG CGT ATC TCT CCG CGC GAC GAT | R | N | R | Q | I | R | R | H | Q2 | Q | I | R | R | I1 | N3 | D | R | Q | R | H | Q2 | R | N | Q | Q | R | R2 | 24759504 | 117310 |
| 1 | 98 | ACT GAG GAG CCT AAG CCA GGT GAA GCC | Q | N3 | Q | N3 | Q2 | R | N | R | R | N | E | N3 | I1 | N3 | Q | N | R | R | Q | R | H1 | R2 | N3 | N3 | Q3 | Q3 | R2 | 76718610 | 17311796 |
| 1 | 99 | AAC TAT GAC CCG AGG GTA GGC ACT ACC | Q | Q1 | R2 | I | N | Q3 | N | Q3 | R2 | E | R | E | Q | Q | R | R | N | Q | R | H1 | R2 | Q | N3 | Q2 | Q | Q3 | R2 | 32201523 | 202169 |
| 1 | 100 | ACT AAG CGT ACA AAG CTC GGA GCA ACC | Q | NE | Q2 | Q | Q | R | E | H | Q2 | D | D | Q | Q | Q | R | E | I | R2 | N | Q | R | R | D | R | Q | Q3 | R2 | 50819418 | 124234 |

*The Optimal DNA sequence in gene 1 is shown as SEQ ID NO: 109 in the Sequence Listing. The sequences in genes 3–31 are shown as SEQ ID NOS: 110–138, respectively. The sequences in genes 33–100 are shown as SEQ ID NOS: 139–206, respectively.

REFERENCES

1. Miller, J., McLachlan, A. D. and Klug, A. (1985) EMBO J. 4, 1609–1614.
2. Berg, J. M. (1988) Proc. Natl. Acad. Sci. USA 85, 99–102.
3. Gibson, T. J., Postma, J. P. M., Brown, R. S. and Argos, P. (1988) Protein Eng. 2, 209–218.
4. Lee, M. S., Gippert, G. P., Soman, K. V., Case, D. A. and Wright, P. E. (1989) Science 245, 635–637.
5. Nardelli, J., Gibson, T. J., Vesque, C. and Charnay, P. (1991) Nature 349, 175–178.
6. Thiesen, H. J. and Bach, C. (1991) FEBS Lett. 283, 23–26.
7. Pavletich, N. P. and Pabo, C. O. (1991) Science 252, 809–817.
8. Berg, J. M. (1992) Proc. Natl. Acad. Sci. USA 89, 11109–11110.
9. Kriwacki, R. W., Schultz, S. C., Steitz, T. A. and Caradonna, J. P. (1992) Proc. Natl. Acad. Sci. USA 89, 9759–9763.
10. Jacobs, G. H. (1992) EMBO J. 11, 4507–4517.
11. Gogos, J. A., Hsu, T., Bolton, J. and Kafatos, F. C. (1992) Science 257, 1951–1955.
12. Fairall, L., Harrison, S. D., Travers, A. A. and Rhodes, D. (1992) J. Mol. Biol. 226, 349–366.
13. Klevit, R. E. (1991) Science 253, 1367 and 1393.
14. Desjarlais, J. R. and Berg, J. M. (1992) Proc. Natl. Acad. Sci. USA 89, 7345–7349.
15. Rebar, E. J., and Pabo, C. O., U.S. Pat. No. 5,789,538, Aug. 4, 1998.
16. Beerli, R. R., Segal, D. J., Dreier, B., and Barbas, C. F. (1998) Proc. Natl. Acad. Sci. U.S.A. 95, 14628–14633.
17. Jordan, S. R. and Pabo, C. O. (1988) Science 242, 893–899.
18. Aggarwal, A. K., Rodgers, D. W., Drottar, M., Ptashne, M. and Harrison S. C. (1988) Science 242, 899–907.
19. Letovsky, J., Dyran, W. S. (1989) Nucleic Acids Res. 17, 2639–2653.
20. Kissinger, C. R., Liu, B., Martin-Blanco, E., Kornberg, T. B. and Pabo, C. O. (1990) Cell 63, 579–590.
21. Wolberger, C., Vershon, A. K., Liu, B., Johnson, A. D. and Pabo, C. O. (1991) Cell 67, 517–528.
22. Seeman, N.C., Rosenberg, J. M. and Rich, A. (1976) Proc. Natl. Acad. Sci USA 73, 804–808.
23. Mikelsaar, R. -H., Bruskov, V. I. and Poltev, V. I. (1985) New precision space-filling atomic-molecular models, Pushchino.
24. Mikelsaar, R. (1986) Trends in Biotechnology 4, 162–163.

What is claimed is:

1. A method for designing a DNA-binding protein (DBP), with multiple zinc-finger (ZF) domains connected by linker sequences, that binds selectively to a target DNA sequence within a given gene, each of said ZF domains having the formula $$A_1XCX_{2-4}CA_2A_3XFXZ_3XXZ_2LXZ_1HX_{3-5}H \quad \text{(SEQ ID NO: 3)}$$

and each of said linkers having the formula $$A_4A_5X_{0-2}EA_6 P \quad \text{(SEQ ID NO 4)},$$

wherein (i) X is any amino acid; (ii) $X_{2-4}$ is a peptide from 2 to 4 amino acids in length; (iii) $X_{3-5}$ is a peptide from 3 to 5 amino acids in length; (iv) $X_{0-2}$ is a peptide from 0 to 2 amino acids in length; (iv) $A_1$ is selected from the group consisting of phenylalanine and tyrosine; (v) $A_2$ is selected from the group consisting of glycine and aspartic acid; (vi) $A_3$ is selected from the group consisting of lysine and arginine; (vii) $A_4$ is selected from the group consisting of threonine and serine; (viii) $A_5$ is selected from the group consisting of glycine and glutamic acid; (ix) $A_6$ is selected from the group consisting of lysine and arginine; (x) C is cysteine; (xi) F is phenylalanine; (xii) L is leucine; (xiii) H is histidine; (xiv) E is glutamic acid; (xv) P is proline; and (xvi) $Z_1$, $Z_2$ and $Z_3$ are the base-contacting amino acids, which method comprises an algorithm comprising the steps of:

(a) setting a genome to be screened;
(b) selecting the target DNA sequence in the genome for binding;
(c) setting the number of ZF domains to $n_d$;
(d) dividing the target DNA sequence into nucleotide blocks wherein each block contains $n_z$ nucleotides using a first routine where $n_z$ is determined using the following relationship:

$$n_z = 3n_d;$$

(e) assigning base-contacting amino acids at $Z_1$, $Z_2$ and $Z_3$ to each ZF domain, according to the A Rules and/or B Rules set forth in Tables 1–3 of the specification, of a DBP which binds to the first nucleotide block from step (d) as numbered from the first 5' nucleotide of the target gene sequence to generate a block-specific DBP and calculating the binding energy, Binding Energy$_{block}$, of each ZF domain of each such block-specific DBP as the product of the binding energies, Binding Energy$_{domain}$, of all ZF domains of the DBP, each determined using the formula:

Binding Energy$_{domain}$=(5×the number of hydrogen bonds)+(2×the number of H$_2$O contacts)+(the number of hydrophobic contacts);

(f) subdividing the DBP from step (d) into blocks using a second routine to generate a subdivided DBP having three ZF domains;

(g) screening the subdivided DBP from step (f) against the genome using a third routine to determine the number of binding sites in the genome for each subdivided DBP in the genome and assigning a binding energy for each such site using the following formula:

Binding Energy$_{site\ n}$=(5×the number of hydrogen bonds)+(2×the number of H$_2$O contacts)+(the number of hydrophobic contacts);

(h) calculating a ratio of binding energy, $R_b$, using a fourth routine for each nucleotide block-specific DBP from step (e) using the following formula:

$R_b$=Binding Energy$_{block}$/the sum of all Binding Energy$_{site\ n}$'s for all subdivided DBP's from step (g);

(i) repeating steps (f) through (h) for each subdivided DBP wherein $n_d \geq 4$;
(j) repeating steps (d) through (i) for each nucleotide block in the target DNA sequence containing $n_z$ nucleotides;
(k) rank-ordering $R_b$ numerical values obtained from step (h); and
(l) selecting a DBP with an acceptable $R_b$ value.

2. The method of claim 1 wherein the DBP selected is that whose $R_b$ numerical value is the highest numerical value for all DBP's in step (h) that bind to the target DNA sequence.

3. The method of claim 1 wherein the DBP $R_b$ numerical value determined in step (h) is at least 10,000.

4. The method of claim 1 wherein the number of ZF domains, $n_d$, is nine.

5. The method of claim 1 wherein the rule s for assigning base-contacting amino acids at $Z_1$, $Z_2$ and $Z_3$ for each nucleotide block in step (e) are selected from rule set A.

6. The method of claim 1 wherein the rules for assigning base-contacting amino acids at $Z_1$, $Z_2$ and $Z_3$ for each nucleotide block in step (e) are selected from rule set B.

7. The method of claim 1 wherein rules for assigning base-contacting amino acids at $Z_1$, $Z_2$ and $Z_3$ for each nucleotide block in step (e) are a combination selected from rule sets A and B.

8. A computer system for designing a DNA-binding protein (DBP), with multiple zinc-finger (ZF) domains connected by linker sequences, that binds selectively to a target DNA sequence within a given gene, each of said ZF domains having the formula $$A_1XCX_{2-4}CA_2A_3XFXZ_3XXZ_2LXZ_1HX_{3-5}H \quad \text{(SEQ ID NO 3)}$$

and each of said linkers having the formula $$A_4A_5X_{0-2}EA_6 P \quad \text{(SEQ ID NO 4)},$$

wherein
(i) X is any amino acid; (ii) $X_{2-4}$ is a peptide from 2 to 4 amino acids in length; (iii) $X_{3-5}$ is a peptide from 3 to 5 amino acids in length; (iv) $X_{0-2}$ is a peptide from 0 to 2 amino acids in length; (iv) $A_1$ is selected from the group consisting of phenylalanine and tyrosine; (v) $A_2$ is selected from the group consisting of glycine and aspartic acid; (vi) $A_3$ is selected from the group consisting of lysine and arginine; (vii) $A_4$ is selected from the group consisting of threonine and serine; (viii) $A_5$ is selected from the group consisting of glycine and glutamic acid; (ix) $A_6$ is selected from the group consisting of lysine and arginine; (x) C is cysteine; (xi) F is phenylalanine; (xii) L is leucine; (xiii) H is histidine; (xiv) E is glutamic acid; (xv) P is proline; and (xvi) $Z_1$, $Z_2$ and $Z_3$ are the base-contacting amino acids, which computer system comprises a computer readable memory which executes a method for designing the DBP, wherein the method comprises the steps of:
(a) setting a genome to be screened;
(b) selecting the target DNA sequence in the genome for binding;
(c) setting the number of ZF domains to $n_d$;
(d) dividing the target DNA sequence into nucleotide blocks wherein each block contains $n_z$ nucleotides using a first routine where $n_z$ is determined using the following relationship:

$$n_z=3n_d;$$

(e) assigning base-contacting amino acids at $Z_1$, $Z_2$ and $Z_3$ to each ZF domain, according to the A Rules and/or B Rules set forth in Tables 1–3 of the specification, of a DBP which binds to the first nucleotide block from step (d) as numbered from the first 5' nucleotide of the target gene sequence to generate a block-specific DBP and calculating the binding energy, Binding Energy$_{block}$, of each ZF domain of each such block-specific DBP as the product of the binding energies, Binding Energy$_{domain}$, of all ZF domains of the DBP, using the formula:

Binding Energy$_{domain}$=(5×the number of hydrogen bonds)+(2×the number of H$_2$O contacts)+(the number of hydrophobic contacts);

(f) subdividing the DBP from step (d) into blocks using a second routine to generate a subdivided DBP having three ZF domains;
(g) screening the subdivided DBP from step (f) against the genome using a third routine to determine the number of binding sites in the genome for each subdivided DBP in the genome and assigning a binding energy for each such site using the following formula:

Binding Energy$_{site\ n}$=(5×the number of hydrogen bonds)+(2×the number of H$_2$O contacts)+(the number of hydrophobic contacts);

(h) calculating a ratio of binding energy, $R_b$, using a fourth routine for each nucleotide block-specific DBP from step (e) using the following formula:

$R_b$=Binding Energy$_{block}$/the sum of all Binding Energy$_{site\ n}$'s for all subdivided DBP's from step (g);

(i) repeating steps (f) through (h) for each subdivided DBP wherein $n_d \geq 4$;
(j) repeating steps (d) through (i) for each nucleotide block in the target DNA sequence containing $n_z$ nucleotides;
(k) rank-ordering $R_b$ numerical values obtained from step (h); and
(l) selecting a DBP with an acceptable $R_b$ value.

9. The computer system according to claim 8 wherein the DBP selected is that whose $R_b$ numerical value is the highest numerical value for all DBP's in step (h) that bind to the target DNA sequence.

10. The computer system according to claim 8 wherein the DBP $R_b$ numerical value determined in step (h) is at least 10,000.

11. The computer system according to claim 8 wherein the number of ZF domains, $n_d$, is nine.

12. The computer system according to claim 8 wherein the rules for assigning base-contacting amino acids at $Z_1$, $Z_2$ and $Z_3$ for each nucleotide block in step (e) are selected from rule set A.

13. The computer system according to claim 8 wherein the rules for assigning base-contacting amino acids at $Z_1$, $Z_2$ and $Z_3$ for each nucleotide block in step (e) are selected from rule set B.

14. The computer system according to claim 8 wherein the rules for assigning base-contacting amino acids at $Z_1$, $Z_2$ and $Z_3$ for each nucleotide block in step (e) are a combination selected from rule sets A and B.

* * * * *

SEQUENCE LISTING

```
<160> NUMBER OF SEQ ID NOS:  231

<210> SEQ ID NO 1
<211> LENGTH: 34
<212> TYPE: PRT
<213> ORGANISM: Artificial Sequence
<220> FEATURE:
<223> OTHER INFORMATION: Description of Artificial Sequence:
      Hypothetical Zinc-Finger Binding Site
<221> NAME/KEY: SITE
<222> LOCATION: (1)
<223> OTHER INFORMATION: Tyr or Phe
<221> NAME/KEY: SITE
<222> LOCATION: (2)
<223> OTHER INFORMATION: any amino acid
<221> NAME/KEY: SITE
<222> LOCATION: (4)..(7)
<223> OTHER INFORMATION: each one of amino acids 4-7 can be any amino
      acid
<221> NAME/KEY: SITE
<222> LOCATION: (4)..(5)
<223> OTHER INFORMATION: any one or all of amino acids 4-5 can either be
      present or absent
<221> NAME/KEY: SITE
<222> LOCATION: (9)
<223> OTHER INFORMATION: Gly or Asp
<221> NAME/KEY: SITE
<222> LOCATION: (10)
<223> OTHER INFORMATION: Lys or Arg
<221> NAME/KEY: SITE
<222> LOCATION: (11)
<223> OTHER INFORMATION: any amino acid
<221> NAME/KEY: SITE
<222> LOCATION: (13)
<223> OTHER INFORMATION: any amino acid
<221> NAME/KEY: SITE
<222> LOCATION: (14)
<223> OTHER INFORMATION: Arg, Glu, Asn, Gln, Ala, Asp, His, Lys, Tyr,
      Ser, Thr, Ile, Leu, or Val
<221> NAME/KEY: SITE
<222> LOCATION: (15)..(16)
<223> OTHER INFORMATION: each one of amino acids 15-16 can be any amino
      acid
<221> NAME/KEY: SITE
```

```
<222> LOCATION: (17)
<223> OTHER INFORMATION: Gln, Asn, Glu, Asp, His, Ala, Ile, Leu, Val,
      Lys, Arg, Ser, Thr, or Tyr
<221> NAME/KEY: SITE
<222> LOCATION: (19)
<223> OTHER INFORMATION: any amino acid
<221> NAME/KEY: SITE
<222> LOCATION: (20)
<223> OTHER INFORMATION: Gln, Arg, Glu, Lys, Ile, Leu, Val, Ala, Asn,
      Asp, His, Ser, Thr, or Tyr
<221> NAME/KEY: SITE
<222> LOCATION: (22)..(26)
<223> OTHER INFORMATION: each one of amino acids 22-26 can be any amino
      acid
<221> NAME/KEY: SITE
<222> LOCATION: (22)..(23)
<223> OTHER INFORMATION: any one or all of amino acids 22-23 can either
      be present or absent
<221> NAME/KEY: SITE
<222> LOCATION: (28)
<223> OTHER INFORMATION: Thr or Ser
<221> NAME/KEY: SITE
<222> LOCATION: (29)
<223> OTHER INFORMATION: Gly or Glu
<221> NAME/KEY: SITE
<222> LOCATION: (30)..(31)
<223> OTHER INFORMATION: each one of amino acids 30-31 can be any amino
      acid
<221> NAME/KEY: SITE
<222> LOCATION: (30)..(31)
<223> OTHER INFORMATION: any one or all of amino acids 30-31 can either
      be present or absent
<221> NAME/KEY: SITE
<222> LOCATION: (33)
<223> OTHER INFORMATION: Lys or Arg

<400> SEQUENCE: 1

Xaa Xaa Cys Xaa Xaa Xaa Xaa Cys Xaa Xaa Xaa Phe Xaa Xaa Xaa Xaa
1               5                   10                  15
Xaa Leu Xaa Xaa His Xaa Xaa Xaa Xaa Xaa His Xaa Xaa Xaa Xaa Glu
            20                  25                  30
Xaa Pro

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:
      Zinc-Finger Domain Segment
<221> NAME/KEY: SITE
<222> LOCATION: (1)
<223> OTHER INFORMATION: Arg, Gln, Asn, Glu, Asp, His, Lys, Tyr, Ser or
      Thr
<221> NAME/KEY: SITE
<222> LOCATION: (2)..(3)
<223> OTHER INFORMATION: each one of amino acids 2-3 can be any amino
      acid
<221> NAME/KEY: SITE
<222> LOCATION: (4)
<223> OTHER INFORMATION: Gln, Glu, Asn, Asp, Ser, Thr, Arg, His, or Lys
<221> NAME/KEY: SITE
<222> LOCATION: (6)
<223> OTHER INFORMATION: any amino acid
<221> NAME/KEY: SITE
<222> LOCATION: (7)
<223> OTHER INFORMATION: Arg, His, Lys, Gln, Asn, Tyr, Ser, or Thr

<400> SEQUENCE: 2

Xaa Xaa Xaa Xaa Leu Xaa Xaa His
1               5

<210> SEQ ID NO 3
<211> LENGTH: 27
<212> TYPE: PRT
```

```
<213> ORGANISM: Artificial Sequence
<220> FEATURE:
<223> OTHER INFORMATION: Description of Artificial Sequence: Zinc-Finger
      Domain Segment
<221> NAME/KEY: SITE
<222> LOCATION: (1)
<223> OTHER INFORMATION: Phe or Tyr
<221> NAME/KEY: SITE
<222> LOCATION: (2)
<223> OTHER INFORMATION: any amino acid
<221> NAME/KEY: SITE
<222> LOCATION: (4)..(7)
<223> OTHER INFORMATION: each one of amino acids 4-7 can be any amino
      acid
<221> NAME/KEY: SITE
<222> LOCATION: (4)..(5)
<223> OTHER INFORMATION: any one or all of amino acids 4-5 can either be
      present or absent
<221> NAME/KEY: SITE
<222> LOCATION: (9)
<223> OTHER INFORMATION: Gly or Asp
<221> NAME/KEY: SITE
<222> LOCATION: (10)
<223> OTHER INFORMATION: Lys or Arg
<221> NAME/KEY: SITE
<222> LOCATION: (11)
<223> OTHER INFORMATION: any amino acid
<221> NAME/KEY: SITE
<222> LOCATION: (13)
<223> OTHER INFORMATION: any amino acid
<221> NAME/KEY: SITE
<222> LOCATION: (14)
<223> OTHER INFORMATION: Arg, Glu, Asn, Gln, Ala, Asp, His, Lys, Tyr,
      Ser, Thr, Ile, Leu, or Val
<221> NAME/KEY: SITE
<222> LOCATION: (15)..(16)
<223> OTHER INFORMATION: each one of amino acids 15-16 can be any amino
      acid
<221> NAME/KEY: SITE
<222> LOCATION: (17)
<223> OTHER INFORMATION: Gln, Asn, Glu, Asp, His, Ala, Ile, Leu, Val,
      Lys, Arg, Ser, Thr, or Tyr
<221> NAME/KEY: SITE
<222> LOCATION: (19)
<223> OTHER INFORMATION: any amino acid
<221> NAME/KEY: SITE
<222> LOCATION: (20)
<223> OTHER INFORMATION: Gln, Arg, Glu, Lys, Ile, Leu, Val, Ala, Asn,
      Asp, His, Ser, Thr, or Tyr
<221> NAME/KEY: SITE
<222> LOCATION: (22)..(26)
<223> OTHER INFORMATION: each one of amino acids 22-26 can be any amino
      acid
<221> NAME/KEY: SITE
<222> LOCATION: (22)..(23)
<223> OTHER INFORMATION: any one or all of amino acids 22-23 can either
      be present or absent

<400> SEQUENCE: 3

Xaa Xaa Cys Xaa Xaa Xaa Xaa Cys Xaa Xaa Xaa Phe Xaa Xaa Xaa Xaa
1               5                   10                  15

Xaa Leu Xaa Xaa His Xaa Xaa Xaa Xaa Xaa His
            20                  25

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Peptide
      Linker
<221> NAME/KEY: SITE
<222> LOCATION: (1)
<223> OTHER INFORMATION: Thr or Ser
<221> NAME/KEY: SITE
<222> LOCATION: (2)
```

```
<223> OTHER INFORMATION: Gly or Glu
<221> NAME/KEY: SITE
<222> LOCATION: (3)..(4)
<223> OTHER INFORMATION: each one of amino acids 3-4 can be any amino
      acid
<221> NAME/KEY: SITE
<222> LOCATION: (3)..(4)
<223> OTHER INFORMATION: any one or all of amino acids 3-4 can either be
      present or absent
<221> NAME/KEY: SITE
<222> LOCATION: (6)
<223> OTHER INFORMATION: Lys or Arg

<400> SEQUENCE: 4

Xaa Xaa Xaa Xaa Glu Xaa Pro
1               5

<210> SEQ ID NO 5
<211> LENGTH: 27
<212> TYPE: DNA
<213> ORGANISM: Saccharomyces cerevisiae

<400> SEQUENCE: 5
cctactctca gattccactt cactcca                                        27

<210> SEQ ID NO 6
<211> LENGTH: 27
<212> TYPE: DNA
<213> ORGANISM: Saccharomyces cerevisiae

<400> SEQUENCE: 6
tcagagctca cttagcccaa tactaca                                        27

<210> SEQ ID NO 7
<211> LENGTH: 27
<212> TYPE: DNA
<213> ORGANISM: Saccharomyces cerevisiae

<400> SEQUENCE: 7
gccgcttggg acgtcgcaga aggagcc                                        27

<210> SEQ ID NO 8
<211> LENGTH: 27
<212> TYPE: DNA
<213> ORGANISM: Saccharomyces cerevisiae

<400> SEQUENCE: 8
gaaaagcata cagcttccga tacatca                                        27

<210> SEQ ID NO 9
<211> LENGTH: 27
<212> TYPE: DNA
<213> ORGANISM: Saccharomyces cerevisiae

<400> SEQUENCE: 9
agtagcataa taggatctag tactgcc                                        27

<210> SEQ ID NO 10
<211> LENGTH: 27
<212> TYPE: DNA
<213> ORGANISM: Saccharomyces cerevisiae

<400> SEQUENCE: 10
gccgtggaaa caattgcaga ggagatg                                        27
```

```
<210> SEQ ID NO 11
<211> LENGTH: 27
<212> TYPE: DNA
<213> ORGANISM: Saccharomyces cerevisiae

<400> SEQUENCE: 11
ccaagtcgag acgcttaaag ttaagtg                                27

<210> SEQ ID NO 12
<211> LENGTH: 27
<212> TYPE: DNA
<213> ORGANISM: Saccharomyces cerevisiae

<400> SEQUENCE: 12
gactacagcg gcatgcctgc cagcaaa                                27

<210> SEQ ID NO 13
<211> LENGTH: 27
<212> TYPE: DNA
<213> ORGANISM: Saccharomyces cerevisiae

<400> SEQUENCE: 13
acttggactg ccgagcgggt cgatcaa                                27

<210> SEQ ID NO 14
<211> LENGTH: 27
<212> TYPE: DNA
<213> ORGANISM: Saccharomyces cerevisiae

<400> SEQUENCE: 14
gacccaactg cgcacgctgc caaggag                                27

<210> SEQ ID NO 15
<211> LENGTH: 27
<212> TYPE: DNA
<213> ORGANISM: Saccharomyces cerevisiae

<400> SEQUENCE: 15
gctgccagca gttgtgcgga cctgcat                                27

<210> SEQ ID NO 16
<211> LENGTH: 27
<212> TYPE: DNA
<213> ORGANISM: Saccharomyces cerevisiae

<400> SEQUENCE: 16
gataacacag tgcagaagac tcctaca                                27

<210> SEQ ID NO 17
<211> LENGTH: 27
<212> TYPE: DNA
<213> ORGANISM: Saccharomyces cerevisiae

<400> SEQUENCE: 17
tatgcacccg atacagaggg tgtcgag                                27

<210> SEQ ID NO 18
<211> LENGTH: 27
<212> TYPE: DNA
<213> ORGANISM: Saccharomyces cerevisiae

<400> SEQUENCE: 18
caagagcacg acggccgcag taagcac                                27
```

<210> SEQ ID NO 19
<211> LENGTH: 27
<212> TYPE: DNA
<213> ORGANISM: Saccharomyces cerevisiae

<400> SEQUENCE: 19
gagatacccg tgatacgtcg cggtaaa                                27

<210> SEQ ID NO 20
<211> LENGTH: 27
<212> TYPE: DNA
<213> ORGANISM: Saccharomyces cerevisiae

<400> SEQUENCE: 20
aatggggcac gacctccaga gggtgat                                27

<210> SEQ ID NO 21
<211> LENGTH: 27
<212> TYPE: DNA
<213> ORGANISM: Saccharomyces cerevisiae

<400> SEQUENCE: 21
gagagacccc aggcgtgaga cacgtct                                27

<210> SEQ ID NO 22
<211> LENGTH: 27
<212> TYPE: DNA
<213> ORGANISM: Saccharomyces cerevisiae

<400> SEQUENCE: 22
acctccgctg tcatgggtac gggtggc                                27

<210> SEQ ID NO 23
<211> LENGTH: 27
<212> TYPE: DNA
<213> ORGANISM: Saccharomyces cerevisiae

<400> SEQUENCE: 23
gaaccgagtt agggcgatc taagcga                                 27

<210> SEQ ID NO 24
<211> LENGTH: 27
<212> TYPE: DNA
<213> ORGANISM: Saccharomyces cerevisiae

<400> SEQUENCE: 24
gatggaacac ccaagggtcg tcgtgaa                                27

<210> SEQ ID NO 25
<211> LENGTH: 27
<212> TYPE: DNA
<213> ORGANISM: Saccharomyces cerevisiae

<400> SEQUENCE: 25
accgaccata caggacgtgc tgccacc                                27

<210> SEQ ID NO 26
<211> LENGTH: 27
<212> TYPE: DNA
<213> ORGANISM: Saccharomyces cerevisiae

<400> SEQUENCE: 26
gaaagacgga agctcgatgc taacgct                                27

<210> SEQ ID NO 27
<211> LENGTH: 27
<212> TYPE: DNA
<213> ORGANISM: Saccharomyces cerevisiae

<400> SEQUENCE: 27
agtcaactgg gaagggtccg gcatcat                                      27

<210> SEQ ID NO 28
<211> LENGTH: 27
<212> TYPE: DNA
<213> ORGANISM: Saccharomyces cerevisiae

<400> SEQUENCE: 28
aggatggtac gtgccacggg accatct                                      27

<210> SEQ ID NO 29
<211> LENGTH: 27
<212> TYPE: DNA
<213> ORGANISM: Saccharomyces cerevisiae

<400> SEQUENCE: 29
atggaccacc cgcatgcccg ctgtgag                                      27

<210> SEQ ID NO 30
<211> LENGTH: 27
<212> TYPE: DNA
<213> ORGANISM: Saccharomyces cerevisiae

<400> SEQUENCE: 30
aagaccccca cgcctgtgtc cgcacct                                      27

<210> SEQ ID NO 31
<211> LENGTH: 27
<212> TYPE: DNA
<213> ORGANISM: Saccharomyces cerevisiae

<400> SEQUENCE: 31
gatcagcccg ccggccctgg tgcggac                                      27

<210> SEQ ID NO 32
<211> LENGTH: 27
<212> TYPE: DNA
<213> ORGANISM: Saccharomyces cerevisiae

<400> SEQUENCE: 32
agtccgcacc agggccggcg ggctgat                                      27

<210> SEQ ID NO 33
<211> LENGTH: 27
<212> TYPE: DNA
<213> ORGANISM: Saccharomyces cerevisiae

<400> SEQUENCE: 33
aatggcgcta accgggacag tagcgac                                      27

<210> SEQ ID NO 34
<211> LENGTH: 27
<212> TYPE: DNA
<213> ORGANISM: Saccharomyces cerevisiae

<400> SEQUENCE: 34

```
gccactgccg cctctgtcag cgctgcc                                              27
```

<210> SEQ ID NO 35
<211> LENGTH: 27
<212> TYPE: DNA
<213> ORGANISM: Saccharomyces cerevisiae

<400> SEQUENCE: 35

```
actccgaggc gagcgcaaag cggaaca                                              27
```

<210> SEQ ID NO 36
<211> LENGTH: 27
<212> TYPE: DNA
<213> ORGANISM: Saccharomyces cerevisiae

<400> SEQUENCE: 36

```
accgtcgctg cctccgctgt cgctgct                                              27
```

<210> SEQ ID NO 37
<211> LENGTH: 27
<212> TYPE: DNA
<213> ORGANISM: Saccharomyces cerevisiae

<400> SEQUENCE: 37

```
acgtaggcag acgagctcag tcaagag                                              27
```

<210> SEQ ID NO 38
<211> LENGTH: 27
<212> TYPE: DNA
<213> ORGANISM: Saccharomyces cerevisiae

<400> SEQUENCE: 38

```
accaccctgg ttaccgtccc cggtgtc                                              27
```

<210> SEQ ID NO 39
<211> LENGTH: 27
<212> TYPE: DNA
<213> ORGANISM: Saccharomyces cerevisiae

<400> SEQUENCE: 39

```
acaacccagg aaaacgcctc cgaagcc                                              27
```

<210> SEQ ID NO 40
<211> LENGTH: 27
<212> TYPE: DNA
<213> ORGANISM: Saccharomyces cerevisiae

<400> SEQUENCE: 40

```
caacaagcga gatgggcgga tatccca                                              27
```

<210> SEQ ID NO 41
<211> LENGTH: 27
<212> TYPE: DNA
<213> ORGANISM: Saccharomyces cerevisiae

<400> SEQUENCE: 41

```
gccggatgcg aggacgcaag cagggga                                              27
```

<210> SEQ ID NO 42
<211> LENGTH: 27
<212> TYPE: DNA
<213> ORGANISM: Saccharomyces cerevisiae

<400> SEQUENCE: 42
aaaggtaccg ctacgccacc tacgggt                                              27

<210> SEQ ID NO 43
<211> LENGTH: 27
<212> TYPE: DNA
<213> ORGANISM: Saccharomyces cerevisiae

<400> SEQUENCE: 43
actgatcgtg aacccgtca aggtaag                                               27

<210> SEQ ID NO 44
<211> LENGTH: 27
<212> TYPE: DNA
<213> ORGANISM: Saccharomyces cerevisiae

<400> SEQUENCE: 44
caacgggact ccgcagacgg gagcaat                                              27

<210> SEQ ID NO 45
<211> LENGTH: 27
<212> TYPE: DNA
<213> ORGANISM: Saccharomyces cerevisiae

<400> SEQUENCE: 45
cccgaggagg taccccctaga tcactat                                             27

<210> SEQ ID NO 46
<211> LENGTH: 27
<212> TYPE: DNA
<213> ORGANISM: Saccharomyces cerevisiae

<400> SEQUENCE: 46
gacccttatg ctctatccga gcacgat                                              27

<210> SEQ ID NO 47
<211> LENGTH: 27
<212> TYPE: DNA
<213> ORGANISM: Saccharomyces cerevisiae

<400> SEQUENCE: 47
caaggtggac agccgaacat agctggt                                              27

<210> SEQ ID NO 48
<211> LENGTH: 27
<212> TYPE: DNA
<213> ORGANISM: Saccharomyces cerevisiae

<400> SEQUENCE: 48
ccggattaca cgtctgcctc gaccgca                                              27

<210> SEQ ID NO 49
<211> LENGTH: 27
<212> TYPE: DNA
<213> ORGANISM: Saccharomyces cerevisiae

<400> SEQUENCE: 49
ggtgccgata cggataatgc ggtaact                                              27

<210> SEQ ID NO 50
<211> LENGTH: 27
<212> TYPE: DNA
<213> ORGANISM: Saccharomyces cerevisiae -continued

<400> SEQUENCE: 50
atcagcgact ctaggccgca cgttcag                                              27

<210> SEQ ID NO 51
<211> LENGTH: 27
<212> TYPE: DNA
<213> ORGANISM: Saccharomyces cerevisiae

<400> SEQUENCE: 51
acgcctgaag aggcgcacac tcctgcc                                              27

<210> SEQ ID NO 52
<211> LENGTH: 27
<212> TYPE: DNA
<213> ORGANISM: Saccharomyces cerevisiae

<400> SEQUENCE: 52
tctagtgccc ggaacacacg gagagca                                              27

<210> SEQ ID NO 53
<211> LENGTH: 27
<212> TYPE: DNA
<213> ORGANISM: Saccharomyces cerevisiae

<400> SEQUENCE: 53
agcgctgatg agagagacgc ggaagat                                              27

<210> SEQ ID NO 54
<211> LENGTH: 27
<212> TYPE: DNA
<213> ORGANISM: Saccharomyces cerevisiae

<400> SEQUENCE: 54
accgccgcac caacggcact cgcgacg                                              27

<210> SEQ ID NO 55
<211> LENGTH: 27
<212> TYPE: DNA
<213> ORGANISM: Saccharomyces cerevisiae

<400> SEQUENCE: 55
acgggagata gcactccctc aggcacg                                              27

<210> SEQ ID NO 56
<211> LENGTH: 27
<212> TYPE: DNA
<213> ORGANISM: Saccharomyces cerevisiae

<400> SEQUENCE: 56
gacgagggcg gccgcatagt gcacgca                                              27

<210> SEQ ID NO 57
<211> LENGTH: 27
<212> TYPE: DNA
<213> ORGANISM: Saccharomyces cerevisiae

<400> SEQUENCE: 57
accgctggcg cagacgccac tagcaag                                              27

<210> SEQ ID NO 58
<211> LENGTH: 27
<212> TYPE: DNA
<213> ORGANISM: Saccharomyces cerevisiae

<400> SEQUENCE: 58
tatgagccgt accagatacg tgctaat                                27

<210> SEQ ID NO 59
<211> LENGTH: 27
<212> TYPE: DNA
<213> ORGANISM: Saccharomyces cerevisiae

<400> SEQUENCE: 59
cagacaccac cgagcccga tcaagag                                 27

<210> SEQ ID NO 60
<211> LENGTH: 27
<212> TYPE: DNA
<213> ORGANISM: Saccharomyces cerevisiae

<400> SEQUENCE: 60
catcgcgttg gcactcggtc ccgaaag                                27

<210> SEQ ID NO 61
<211> LENGTH: 27
<212> TYPE: DNA
<213> ORGANISM: Saccharomyces cerevisiae

<400> SEQUENCE: 61
gctattgggc ctgcccggtg tagggcc                                27

<210> SEQ ID NO 62
<211> LENGTH: 27
<212> TYPE: DNA
<213> ORGANISM: Saccharomyces cerevisiae

<400> SEQUENCE: 62
attcctgata cggcggttga caaggag                                27

<210> SEQ ID NO 63
<211> LENGTH: 27
<212> TYPE: DNA
<213> ORGANISM: Saccharomyces cerevisiae

<400> SEQUENCE: 63
gacgccaggg acgagcaagg ggacgaa                                27

<210> SEQ ID NO 64
<211> LENGTH: 27
<212> TYPE: DNA
<213> ORGANISM: Saccharomyces cerevisiae

<400> SEQUENCE: 64
gtcgccaacg ctcacggtgt ggaaacc                                27

<210> SEQ ID NO 65
<211> LENGTH: 27
<212> TYPE: DNA
<213> ORGANISM: Saccharomyces cerevisiae

<400> SEQUENCE: 65 agaagggca agcgtggtcg tgacgat                                 27

<210> SEQ ID NO 66
<211> LENGTH: 27
<212> TYPE: DNA

<213> ORGANISM: Saccharomyces cerevisiae

<400> SEQUENCE: 66
cagcagagcg actaaactac tgcacga 27

<210> SEQ ID NO 67
<211> LENGTH: 27
<212> TYPE: DNA
<213> ORGANISM: Saccharomyces cerevisiae

<400> SEQUENCE: 67
gatgtgggga accatgccca ggatgat 27

<210> SEQ ID NO 68
<211> LENGTH: 27
<212> TYPE: DNA
<213> ORGANISM: Saccharomyces cerevisiae

<400> SEQUENCE: 68
actgtgggca acagtacggc aattacc 27

<210> SEQ ID NO 69
<211> LENGTH: 27
<212> TYPE: DNA
<213> ORGANISM: Saccharomyces cerevisiae

<400> SEQUENCE: 69
actgacgagc atgaagctga tgtcaat 27

<210> SEQ ID NO 70
<211> LENGTH: 27
<212> TYPE: DNA
<213> ORGANISM: Saccharomyces cerevisiae

<400> SEQUENCE: 70
gacccagaag tgcaggctga catgaag 27

<210> SEQ ID NO 71
<211> LENGTH: 27
<212> TYPE: DNA
<213> ORGANISM: Saccharomyces cerevisiae

<400> SEQUENCE: 71
gatcattagc aaagtgagca acacacg 27

<210> SEQ ID NO 72
<211> LENGTH: 27
<212> TYPE: DNA
<213> ORGANISM: Saccharomyces cerevisiae

<400> SEQUENCE: 72
gatgggaagt aagaccccccg atatgag 27

<210> SEQ ID NO 73
<211> LENGTH: 27
<212> TYPE: DNA
<213> ORGANISM: Saccharomyces cerevisiae

<400> SEQUENCE: 73
ggtgctcggc atacagccct gattgtt 27

<210> SEQ ID NO 74
<211> LENGTH: 27

-continued

```
<212> TYPE: DNA
<213> ORGANISM: Saccharomyces cerevisiae

<400> SEQUENCE: 74
catgtcagca ctgcacagga gccgaaa                                      27

<210> SEQ ID NO 75
<211> LENGTH: 27
<212> TYPE: DNA
<213> ORGANISM: Saccharomyces cerevisiae

<400> SEQUENCE: 75
gctagcgcta ctgtgccttc cgctccc                                      27

<210> SEQ ID NO 76
<211> LENGTH: 27
<212> TYPE: DNA
<213> ORGANISM: Saccharomyces cerevisiae

<400> SEQUENCE: 76
gatcgtgaag ctacctttag agacgcc                                      27

<210> SEQ ID NO 77
<211> LENGTH: 27
<212> TYPE: DNA
<213> ORGANISM: Saccharomyces cerevisiae

<400> SEQUENCE: 77
aacgttggtg agagtcctgg aaggggc                                      27

<210> SEQ ID NO 78
<211> LENGTH: 27
<212> TYPE: DNA
<213> ORGANISM: Saccharomyces cerevisiae

<400> SEQUENCE: 78
gctgaagccg actatcttgc cgatgag                                      27

<210> SEQ ID NO 79
<211> LENGTH: 27
<212> TYPE: DNA
<213> ORGANISM: Saccharomyces cerevisiae

<400> SEQUENCE: 79
gaataacatt agagcggggc gccaaac                                      27

<210> SEQ ID NO 80
<211> LENGTH: 27
<212> TYPE: DNA
<213> ORGANISM: Saccharomyces cerevisiae

<400> SEQUENCE: 80
caatgcacag acaaattcga tactcac                                      27

<210> SEQ ID NO 81
<211> LENGTH: 27
<212> TYPE: DNA
<213> ORGANISM: Saccharomyces cerevisiae

<400> SEQUENCE: 81
gctaatcacg tcgacgtcgg gcatgga                                      27

<210> SEQ ID NO 82
```

```
<211> LENGTH: 27
<212> TYPE: DNA
<213> ORGANISM: Saccharomyces cerevisiae

<400> SEQUENCE: 82
cctgcccagg ccgctgagct ggtgggt                                27

<210> SEQ ID NO 83
<211> LENGTH: 27
<212> TYPE: DNA
<213> ORGANISM: Saccharomyces cerevisiae

<400> SEQUENCE: 83
acccaggcag tggaggagcg agccagg                                27

<210> SEQ ID NO 84
<211> LENGTH: 27
<212> TYPE: DNA
<213> ORGANISM: Saccharomyces cerevisiae

<400> SEQUENCE: 84
cgagcggctc ccgctccctg ggcagaa                                27

<210> SEQ ID NO 85
<211> LENGTH: 27
<212> TYPE: DNA
<213> ORGANISM: Saccharomyces cerevisiae

<400> SEQUENCE: 85
gtgcctccgc cgcagcaacc actacat                                27

<210> SEQ ID NO 86
<211> LENGTH: 27
<212> TYPE: DNA
<213> ORGANISM: Saccharomyces cerevisiae

<400> SEQUENCE: 86
cctgatgtac agtgggatac agcgaat                                27

<210> SEQ ID NO 87
<211> LENGTH: 27
<212> TYPE: DNA
<213> ORGANISM: Saccharomyces cerevisiae

<400> SEQUENCE: 87
ccaacgaacg gtgcagagaa tacgcag                                27

<210> SEQ ID NO 88
<211> LENGTH: 27
<212> TYPE: DNA
<213> ORGANISM: Saccharomyces cerevisiae

<400> SEQUENCE: 88
ggtgatcgca cgcaagcctg cggggaa                                27

<210> SEQ ID NO 89
<211> LENGTH: 27
<212> TYPE: DNA
<213> ORGANISM: Saccharomyces cerevisiae

<400> SEQUENCE: 89
gagaagccaa caagcaacgc tgaggaa                                27
```

```
<210> SEQ ID NO 90
<211> LENGTH: 27
<212> TYPE: DNA
<213> ORGANISM: Saccharomyces cerevisiae

<400> SEQUENCE: 90
gaggcgacat aagttgttag cacagca                               27

<210> SEQ ID NO 91
<211> LENGTH: 27
<212> TYPE: DNA
<213> ORGANISM: Saccharomyces cerevisiae

<400> SEQUENCE: 91
gatcatgggc tatgggatac tccctac                               27

<210> SEQ ID NO 92
<211> LENGTH: 27
<212> TYPE: DNA
<213> ORGANISM: Saccharomyces cerevisiae

<400> SEQUENCE: 92
aagttagata cacttaacga acctagt                               27

<210> SEQ ID NO 93
<211> LENGTH: 27
<212> TYPE: DNA
<213> ORGANISM: Saccharomyces cerevisiae

<400> SEQUENCE: 93
aatgctccca ggggctcggc caggacc                               27

<210> SEQ ID NO 94
<211> LENGTH: 27
<212> TYPE: DNA
<213> ORGANISM: Saccharomyces cerevisiae

<400> SEQUENCE: 94
gattcgccac ggcacactcc gcacaga                               27

<210> SEQ ID NO 95
<211> LENGTH: 27
<212> TYPE: DNA
<213> ORGANISM: Saccharomyces cerevisiae

<400> SEQUENCE: 95
gcggagtgag ccgccgaggc caacgac                               27

<210> SEQ ID NO 96
<211> LENGTH: 27
<212> TYPE: DNA
<213> ORGANISM: Saccharomyces cerevisiae

<400> SEQUENCE: 96
acatcgccgc ctaccagtcc cgcggtg                               27

<210> SEQ ID NO 97
<211> LENGTH: 27
<212> TYPE: DNA
<213> ORGANISM: Saccharomyces cerevisiae

<400> SEQUENCE: 97
ggtatcgcca gtctccgggt ccatacc                               27
```

```
<210> SEQ ID NO 98
<211> LENGTH: 27
<212> TYPE: DNA
<213> ORGANISM: Saccharomyces cerevisiae

<400> SEQUENCE: 98
atcactcccg gtccacattc taggaag                                27

<210> SEQ ID NO 99
<211> LENGTH: 27
<212> TYPE: DNA
<213> ORGANISM: Saccharomyces cerevisiae

<400> SEQUENCE: 99
aatgtcagtt gtgacgctag acttttc                                27

<210> SEQ ID NO 100
<211> LENGTH: 27
<212> TYPE: DNA
<213> ORGANISM: Saccharomyces cerevisiae

<400> SEQUENCE: 100
aatactgtag ctgctgagac gattacc                                27

<210> SEQ ID NO 101
<211> LENGTH: 27
<212> TYPE: DNA
<213> ORGANISM: Saccharomyces cerevisiae

<400> SEQUENCE: 101
agctgtggaa acaatcgcag gggagat                                27

<210> SEQ ID NO 102
<211> LENGTH: 27
<212> TYPE: DNA
<213> ORGANISM: Saccharomyces cerevisiae

<400> SEQUENCE: 102
gtagaaatct gctgcacatg ccacacg                                27

<210> SEQ ID NO 103
<211> LENGTH: 27
<212> TYPE: DNA
<213> ORGANISM: Saccharomyces cerevisiae

<400> SEQUENCE: 103
gctacggaga aaccgtgcac taactct                                27

<210> SEQ ID NO 104
<211> LENGTH: 27
<212> TYPE: DNA
<213> ORGANISM: Saccharomyces cerevisiae

<400> SEQUENCE: 104
accgtttcct ccaagtcata caccact                                27

<210> SEQ ID NO 105
<211> LENGTH: 27
<212> TYPE: DNA
<213> ORGANISM: Saccharomyces cerevisiae

<400> SEQUENCE: 105
ctatatattt gtggcagaaa tcatacc                                27
```

<210> SEQ ID NO 106
<211> LENGTH: 27
<212> TYPE: DNA
<213> ORGANISM: Saccharomyces cerevisiae

<400> SEQUENCE: 106
tatcatgaca acatggtaca aattgag                                    27

<210> SEQ ID NO 107
<211> LENGTH: 27
<212> TYPE: DNA
<213> ORGANISM: Saccharomyces cerevisiae

<400> SEQUENCE: 107
aagaccgcac tagatcttac caagagc                                    27

<210> SEQ ID NO 108
<211> LENGTH: 27
<212> TYPE: DNA
<213> ORGANISM: Saccharomyces cerevisiae

<400> SEQUENCE: 108
atgacgacat ccaagccagc ttttacc                                    27

<210> SEQ ID NO 109
<211> LENGTH: 27
<212> TYPE: DNA
<213> ORGANISM: Caenorhabditis elegans

<400> SEQUENCE: 109
acgaagccgc ccgactccta ggagatg                                    27

<210> SEQ ID NO 110
<211> LENGTH: 27
<212> TYPE: DNA
<213> ORGANISM: Caenorhabditis elegans

<400> SEQUENCE: 110
gacgccgagc acgagcacag gagcgaa                                    27

<210> SEQ ID NO 111
<211> LENGTH: 27
<212> TYPE: DNA
<213> ORGANISM: Caenorhabditis elegans

<400> SEQUENCE: 111
gacaattctc ccggcgccaa tgatcac                                    27

<210> SEQ ID NO 112
<211> LENGTH: 27
<212> TYPE: DNA
<213> ORGANISM: Caenorhabditis elegans

<400> SEQUENCE: 112
agcacgactc ggcacacccg ttccgcc                                    27

<210> SEQ ID NO 113
<211> LENGTH: 27
<212> TYPE: DNA
<213> ORGANISM: Caenorhabditis elegans

<400> SEQUENCE: 113

-continued ccaggaaggc gcactggcag acgtaag                                              27

<210> SEQ ID NO 114
<211> LENGTH: 27
<212> TYPE: DNA
<213> ORGANISM: Caenorhabditis elegans

<400> SEQUENCE: 114
gctattactc gtggtgccgc gggagcc                                              27

<210> SEQ ID NO 115
<211> LENGTH: 27
<212> TYPE: DNA
<213> ORGANISM: Caenorhabditis elegans

<400> SEQUENCE: 115
aatagcgaac agatatctga caactcc                                              27

<210> SEQ ID NO 116
<211> LENGTH: 27
<212> TYPE: DNA
<213> ORGANISM: Caenorhabditis elegans

<400> SEQUENCE: 116
gtcgcgcata ctaaggctcg ctttaat                                              27

<210> SEQ ID NO 117
<211> LENGTH: 27
<212> TYPE: DNA
<213> ORGANISM: Caenorhabditis elegans

<400> SEQUENCE: 117
gatattcgcg atggcaccgg tgacgat                                              27

<210> SEQ ID NO 118
<211> LENGTH: 27
<212> TYPE: DNA
<213> ORGANISM: Caenorhabditis elegans

<400> SEQUENCE: 118
cataacgtcg aggctgcccg caaggag                                              27

<210> SEQ ID NO 119
<211> LENGTH: 27
<212> TYPE: DNA
<213> ORGANISM: Caenorhabditis elegans

<400> SEQUENCE: 119
accagccatc acgccatgcg aagcacc                                              27

<210> SEQ ID NO 120
<211> LENGTH: 27
<212> TYPE: DNA
<213> ORGANISM: Caenorhabditis elegans

<400> SEQUENCE: 120
aggcaccccg ggaagcgccg gaccgaa                                              27

<210> SEQ ID NO 121
<211> LENGTH: 27
<212> TYPE: DNA
<213> ORGANISM: Caenorhabditis elegans

<400> SEQUENCE: 121
ggagcaccag acgccccgac taagccg                                              27

<210> SEQ ID NO 122
<211> LENGTH: 27
<212> TYPE: DNA
<213> ORGANISM: Caenorhabditis elegans

<400> SEQUENCE: 122
gatgctcgcc tactcgcgag gccaaga                                              27

<210> SEQ ID NO 123
<211> LENGTH: 27
<212> TYPE: DNA
<213> ORGANISM: Caenorhabditis elegans

<400> SEQUENCE: 123
agagccgatg cccgcaccaa ggctgct                                              27

<210> SEQ ID NO 124
<211> LENGTH: 27
<212> TYPE: DNA
<213> ORGANISM: Caenorhabditis elegans

<400> SEQUENCE: 124
acagacgagg ccaagatcta cgccgaa                                              27

<210> SEQ ID NO 125
<211> LENGTH: 27
<212> TYPE: DNA
<213> ORGANISM: Caenorhabditis elegans

<400> SEQUENCE: 125
ccaaccggta ggccgatagg tagtcgc                                              27

<210> SEQ ID NO 126
<211> LENGTH: 27
<212> TYPE: DNA
<213> ORGANISM: Caenorhabditis elegans

<400> SEQUENCE: 126
cctacaaggc cccgtacgag ggccgat                                              27

<210> SEQ ID NO 127
<211> LENGTH: 27
<212> TYPE: DNA
<213> ORGANISM: Caenorhabditis elegans

<400> SEQUENCE: 127
accaacggac aggatggcgc cgaacaa                                              27

<210> SEQ ID NO 128
<211> LENGTH: 27
<212> TYPE: DNA
<213> ORGANISM: Caenorhabditis elegans

<400> SEQUENCE: 128
gcaagccgct atgtcgacgc tcgccaa                                              27

<210> SEQ ID NO 129
<211> LENGTH: 27
<212> TYPE: DNA
<213> ORGANISM: Caenorhabditis elegans -continued

```
<400> SEQUENCE: 129
agtccgccta agcgccctgt tccgccg                                              27

<210> SEQ ID NO 130
<211> LENGTH: 27
<212> TYPE: DNA
<213> ORGANISM: Caenorhabditis elegans

<400> SEQUENCE: 130
aagcggatcg ctgcgaccga accgcct                                              27

<210> SEQ ID NO 131
<211> LENGTH: 27
<212> TYPE: DNA
<213> ORGANISM: Caenorhabditis elegans

<400> SEQUENCE: 131
aatgatctag ctcccagtcc tactgcg                                              27

<210> SEQ ID NO 132
<211> LENGTH: 27
<212> TYPE: DNA
<213> ORGANISM: Caenorhabditis elegans

<400> SEQUENCE: 132
cagaggactc gccgtatcgt cgctggt                                              27

<210> SEQ ID NO 133
<211> LENGTH: 27
<212> TYPE: DNA
<213> ORGANISM: Caenorhabditis elegans

<400> SEQUENCE: 133
gctatgaggt cacgggctcc ccctgat                                              27

<210> SEQ ID NO 134
<211> LENGTH: 27
<212> TYPE: DNA
<213> ORGANISM: Caenorhabditis elegans

<400> SEQUENCE: 134
gacacaggtc cccatcacgg gacaagt                                              27

<210> SEQ ID NO 135
<211> LENGTH: 27
<212> TYPE: DNA
<213> ORGANISM: Caenorhabditis elegans

<400> SEQUENCE: 135
cacgttggga ccgccaggag cccgaat                                              27

<210> SEQ ID NO 136
<211> LENGTH: 27
<212> TYPE: DNA
<213> ORGANISM: Caenorhabditis elegans

<400> SEQUENCE: 136
cgagaacgtc ccatcaagcg tgaacac                                              27

<210> SEQ ID NO 137
<211> LENGTH: 27
<212> TYPE: DNA
<213> ORGANISM: Caenorhabditis elegans
```

<400> SEQUENCE: 137
gatccttcga gtacgcctac gcaagga 27

<210> SEQ ID NO 138
<211> LENGTH: 27
<212> TYPE: DNA
<213> ORGANISM: Caenorhabditis elegans

<400> SEQUENCE: 138
aacgccgcct agaccccggg gaatacc 27

<210> SEQ ID NO 139
<211> LENGTH: 27
<212> TYPE: DNA
<213> ORGANISM: Caenorhabditis elegans

<400> SEQUENCE: 139
gtggtgcagg aggggcagga ggccaca 27

<210> SEQ ID NO 140
<211> LENGTH: 27
<212> TYPE: DNA
<213> ORGANISM: Caenorhabditis elegans

<400> SEQUENCE: 140
cgtacaagga ataccctgaa ggacaac 27

<210> SEQ ID NO 141
<211> LENGTH: 27
<212> TYPE: DNA
<213> ORGANISM: Caenorhabditis elegans

<400> SEQUENCE: 141
acctccactc agcgaccacc ggcgcca 27

<210> SEQ ID NO 142
<211> LENGTH: 27
<212> TYPE: DNA
<213> ORGANISM: Caenorhabditis elegans

<400> SEQUENCE: 142
aaagcggtac aagcgacgac ccgtgct 27

<210> SEQ ID NO 143
<211> LENGTH: 27
<212> TYPE: DNA
<213> ORGANISM: Caenorhabditis elegans

<400> SEQUENCE: 143
acaacgaccg aggagcctac cgaagcc 27

<210> SEQ ID NO 144
<211> LENGTH: 27
<212> TYPE: DNA
<213> ORGANISM: Caenorhabditis elegans

<400> SEQUENCE: 144
gagaaccgtc cccacccgaa gctggct 27

<210> SEQ ID NO 145
<211> LENGTH: 27
<212> TYPE: DNA

-continued

<213> ORGANISM: Caenorhabditis elegans

<400> SEQUENCE: 145
cgtcgggtgc ccgagactgg gaccggt 27

<210> SEQ ID NO 146
<211> LENGTH: 27
<212> TYPE: DNA
<213> ORGANISM: Caenorhabditis elegans

<400> SEQUENCE: 146
agggaccgta cggaacagga cccccct 27

<210> SEQ ID NO 147
<211> LENGTH: 27
<212> TYPE: DNA
<213> ORGANISM: Caenorhabditis elegans

<400> SEQUENCE: 147
aggcaaccct ggaggcgtcc cagcacc 27

<210> SEQ ID NO 148
<211> LENGTH: 27
<212> TYPE: DNA
<213> ORGANISM: Caenorhabditis elegans

<400> SEQUENCE: 148
ctcactaccc cggcaccaag gaccagt 27

<210> SEQ ID NO 149
<211> LENGTH: 27
<212> TYPE: DNA
<213> ORGANISM: Caenorhabditis elegans

<400> SEQUENCE: 149
gacgagcacc taaagaccgc cactccg 27

<210> SEQ ID NO 150
<211> LENGTH: 27
<212> TYPE: DNA
<213> ORGANISM: Caenorhabditis elegans

<400> SEQUENCE: 150
cccgtcgggt agacggcggt taccggc 27

<210> SEQ ID NO 151
<211> LENGTH: 27
<212> TYPE: DNA
<213> ORGANISM: Caenorhabditis elegans

<400> SEQUENCE: 151
aggccagggg ccccctacgc cccaaca 27

<210> SEQ ID NO 152
<211> LENGTH: 27
<212> TYPE: DNA
<213> ORGANISM: Caenorhabditis elegans

<400> SEQUENCE: 152
caagctcccg taacacaacc ccggaga 27

<210> SEQ ID NO 153
<211> LENGTH: 27

```
<212> TYPE: DNA
<213> ORGANISM: Caenorhabditis elegans

<400> SEQUENCE: 153
cccgggggcc ccctccggc ggacgat                                    27

<210> SEQ ID NO 154
<211> LENGTH: 27
<212> TYPE: DNA
<213> ORGANISM: Caenorhabditis elegans

<400> SEQUENCE: 154
actgcccaaa tcaaggcccc gagacat                                   27

<210> SEQ ID NO 155
<211> LENGTH: 27
<212> TYPE: DNA
<213> ORGANISM: Caenorhabditis elegans

<400> SEQUENCE: 155
actactccca cgcggcggac acccaac                                   27

<210> SEQ ID NO 156
<211> LENGTH: 27
<212> TYPE: DNA
<213> ORGANISM: Caenorhabditis elegans

<400> SEQUENCE: 156
atcgacccgc atgcgctggc gcagacg                                   27

<210> SEQ ID NO 157
<211> LENGTH: 27
<212> TYPE: DNA
<213> ORGANISM: Caenorhabditis elegans

<400> SEQUENCE: 157
agtaccgcgg atcaggcggc gtccgta                                   27

<210> SEQ ID NO 158
<211> LENGTH: 27
<212> TYPE: DNA
<213> ORGANISM: Caenorhabditis elegans

<400> SEQUENCE: 158
gcagctcaag caggcgacaa cgccgaa                                   27

<210> SEQ ID NO 159
<211> LENGTH: 27
<212> TYPE: DNA
<213> ORGANISM: Caenorhabditis elegans

<400> SEQUENCE: 159
gtgaccgaca cgcccagtaa gtcggga                                   27

<210> SEQ ID NO 160
<211> LENGTH: 27
<212> TYPE: DNA
<213> ORGANISM: Caenorhabditis elegans

<400> SEQUENCE: 160
gacctggcgg cggccgccgg tagcaag                                   27

<210> SEQ ID NO 161
```

```
<211> LENGTH: 27
<212> TYPE: DNA
<213> ORGANISM: Caenorhabditis elegans

<400> SEQUENCE: 161
accgccgccg agctctgcgg cgctgaa                                        27

<210> SEQ ID NO 162
<211> LENGTH: 27
<212> TYPE: DNA
<213> ORGANISM: Caenorhabditis elegans

<400> SEQUENCE: 162
aaagaccgca agcagggac gcaagat                                         27

<210> SEQ ID NO 163
<211> LENGTH: 27
<212> TYPE: DNA
<213> ORGANISM: Caenorhabditis elegans

<400> SEQUENCE: 163
cctacggcgc tagacaggac tccgcag                                        27

<210> SEQ ID NO 164
<211> LENGTH: 27
<212> TYPE: DNA
<213> ORGANISM: Caenorhabditis elegans

<400> SEQUENCE: 164
agagcgcacc ggcagacgcg cgggaat                                        27

<210> SEQ ID NO 165
<211> LENGTH: 27
<212> TYPE: DNA
<213> ORGANISM: Caenorhabditis elegans

<400> SEQUENCE: 165
ggacgtcgcg cagacaccgc ccaaaga                                        27

<210> SEQ ID NO 166
<211> LENGTH: 27
<212> TYPE: DNA
<213> ORGANISM: Caenorhabditis elegans

<400> SEQUENCE: 166
aatcagtcag acccagaggg tgaagct                                        27

<210> SEQ ID NO 167
<211> LENGTH: 27
<212> TYPE: DNA
<213> ORGANISM: Caenorhabditis elegans

<400> SEQUENCE: 167
caacatcgtc ccggcgacac cgacgac                                        27

<210> SEQ ID NO 168
<211> LENGTH: 27
<212> TYPE: DNA
<213> ORGANISM: Caenorhabditis elegans

<400> SEQUENCE: 168
ggagcccgtg cggcggatcc gcgctaa                                        27
```

-continued

```
<210> SEQ ID NO 169
<211> LENGTH: 27
<212> TYPE: DNA
<213> ORGANISM: Caenorhabditis elegans

<400> SEQUENCE: 169
gccactcagg cagcaactca ggcagcc                                27

<210> SEQ ID NO 170
<211> LENGTH: 27
<212> TYPE: DNA
<213> ORGANISM: Caenorhabditis elegans

<400> SEQUENCE: 170
ccaaatggtc aagccgggga ggcaaac                                27

<210> SEQ ID NO 171
<211> LENGTH: 27
<212> TYPE: DNA
<213> ORGANISM: Caenorhabditis elegans

<400> SEQUENCE: 171
ccaatggcca tcgacgcggc gaccaca                                27

<210> SEQ ID NO 172
<211> LENGTH: 27
<212> TYPE: DNA
<213> ORGANISM: Caenorhabditis elegans

<400> SEQUENCE: 172
gaccgtcagg atcgcgatta ccggcca                                27

<210> SEQ ID NO 173
<211> LENGTH: 27
<212> TYPE: DNA
<213> ORGANISM: Caenorhabditis elegans

<400> SEQUENCE: 173
acagcggcag ctactacctc tcccgaa                                27

<210> SEQ ID NO 174
<211> LENGTH: 27
<212> TYPE: DNA
<213> ORGANISM: Caenorhabditis elegans

<400> SEQUENCE: 174
gcccagccaa ccacggggag ggctagg                                27

<210> SEQ ID NO 175
<211> LENGTH: 27
<212> TYPE: DNA
<213> ORGANISM: Caenorhabditis elegans

<400> SEQUENCE: 175
aacaacaggc cagctggagg gaatact                                27

<210> SEQ ID NO 176
<211> LENGTH: 27
<212> TYPE: DNA
<213> ORGANISM: Caenorhabditis elegans

<400> SEQUENCE: 176
aacgcgagcg gaacctaacc gacgcaa                                27
```

<210> SEQ ID NO 177
<211> LENGTH: 27
<212> TYPE: DNA
<213> ORGANISM: Caenorhabditis elegans

<400> SEQUENCE: 177
gcacgcaacg ctgcacgcag cgcagca                                    27

<210> SEQ ID NO 178
<211> LENGTH: 27
<212> TYPE: DNA
<213> ORGANISM: Caenorhabditis elegans

<400> SEQUENCE: 178
aatccgccca cgtacatcgg tccccaa                                    27

<210> SEQ ID NO 179
<211> LENGTH: 27
<212> TYPE: DNA
<213> ORGANISM: Caenorhabditis elegans

<400> SEQUENCE: 179
gaggttcggg cttcagggca ggcggcc                                    27

<210> SEQ ID NO 180
<211> LENGTH: 27
<212> TYPE: DNA
<213> ORGANISM: Caenorhabditis elegans

<400> SEQUENCE: 180
aagcaggcgc aaggtaggcc tggggta                                    27

<210> SEQ ID NO 181
<211> LENGTH: 27
<212> TYPE: DNA
<213> ORGANISM: Caenorhabditis elegans

<400> SEQUENCE: 181
cagacagtag cctctgcgca tgaggag                                    27

<210> SEQ ID NO 182
<211> LENGTH: 27
<212> TYPE: DNA
<213> ORGANISM: Caenorhabditis elegans

<400> SEQUENCE: 182
gcccccgacc aactcagggc caccgct                                    27

<210> SEQ ID NO 183
<211> LENGTH: 27
<212> TYPE: DNA
<213> ORGANISM: Caenorhabditis elegans

<400> SEQUENCE: 183
gcttaggtag ccctgaaggc taacaga                                    27

<210> SEQ ID NO 184
<211> LENGTH: 27
<212> TYPE: DNA
<213> ORGANISM: Caenorhabditis elegans

<400> SEQUENCE: 184
ggcgaggaca cggcaccacg ccaacga                                    27

<210> SEQ ID NO 185
<211> LENGTH: 27
<212> TYPE: DNA
<213> ORGANISM: Caenorhabditis elegans

<400> SEQUENCE: 185
acaagccacg ctcccggtta gtcgaga                                    27

<210> SEQ ID NO 186
<211> LENGTH: 27
<212> TYPE: DNA
<213> ORGANISM: Caenorhabditis elegans

<400> SEQUENCE: 186
gagcaaaccg tggccacgtt gaaccat                                    27

<210> SEQ ID NO 187
<211> LENGTH: 27
<212> TYPE: DNA
<213> ORGANISM: Caenorhabditis elegans

<400> SEQUENCE: 187
ccaaaccttA caagccgtgc ggaggaa                                    27

<210> SEQ ID NO 188
<211> LENGTH: 27
<212> TYPE: DNA
<213> ORGANISM: Caenorhabditis elegans

<400> SEQUENCE: 188
actgctggtg caccgaagga agacaag                                    27

<210> SEQ ID NO 189
<211> LENGTH: 27
<212> TYPE: DNA
<213> ORGANISM: Caenorhabditis elegans

<400> SEQUENCE: 189
ctcccaagtg cgtctgatcc cgatacc                                    27

<210> SEQ ID NO 190
<211> LENGTH: 27
<212> TYPE: DNA
<213> ORGANISM: Caenorhabditis elegans

<400> SEQUENCE: 190
catgtaggaa gtaacgtcgc ccatggc                                    27

<210> SEQ ID NO 191
<211> LENGTH: 27
<212> TYPE: DNA
<213> ORGANISM: Caenorhabditis elegans

<400> SEQUENCE: 191
gaaaagggcg acgccacccc actgcac                                    27

<210> SEQ ID NO 192
<211> LENGTH: 27
<212> TYPE: DNA
<213> ORGANISM: Caenorhabditis elegans

<400> SEQUENCE: 192

-continued actcggggcg gtgtgctcag gactaga                       27

<210> SEQ ID NO 193
<211> LENGTH: 27
<212> TYPE: DNA
<213> ORGANISM: Caenorhabditis elegans

<400> SEQUENCE: 193
acacgccaga cggcccacgc ccccaat                       27

<210> SEQ ID NO 194
<211> LENGTH: 27
<212> TYPE: DNA
<213> ORGANISM: Caenorhabditis elegans

<400> SEQUENCE: 194
aatggtgctt atgtctgcga tcatgct                       27

<210> SEQ ID NO 195
<211> LENGTH: 27
<212> TYPE: DNA
<213> ORGANISM: Caenorhabditis elegans

<400> SEQUENCE: 195
acatatacgg acggggtcg gattacg                        27

<210> SEQ ID NO 196
<211> LENGTH: 27
<212> TYPE: DNA
<213> ORGANISM: Caenorhabditis elegans

<400> SEQUENCE: 196
gatcataacc cgggttggcc taaggac                       27

<210> SEQ ID NO 197
<211> LENGTH: 27
<212> TYPE: DNA
<213> ORGANISM: Caenorhabditis elegans

<400> SEQUENCE: 197
gatcaggccg ttaagacaca gcctaac                       27

<210> SEQ ID NO 198
<211> LENGTH: 27
<212> TYPE: DNA
<213> ORGANISM: Caenorhabditis elegans

<400> SEQUENCE: 198
aatgcaacgg atgctcccgc tgatgct                       27

<210> SEQ ID NO 199
<211> LENGTH: 27
<212> TYPE: DNA
<213> ORGANISM: Caenorhabditis elegans

<400> SEQUENCE: 199
gatcctatcg gtgatatcag ggagatg                       27

<210> SEQ ID NO 200
<211> LENGTH: 27
<212> TYPE: DNA
<213> ORGANISM: Caenorhabditis elegans

<400> SEQUENCE: 200

```
cactctgagg tcggataagg gaatacg                                             27
```

<210> SEQ ID NO 201
<211> LENGTH: 27
<212> TYPE: DNA
<213> ORGANISM: Caenorhabditis elegans

<400> SEQUENCE: 201

```
gctcccagcg cagctgcgtc cggagcg                                             27
```

<210> SEQ ID NO 202
<211> LENGTH: 27
<212> TYPE: DNA
<213> ORGANISM: Caenorhabditis elegans

<400> SEQUENCE: 202

```
gatggtcccg ggccttacgc aatgaca                                             27
```

<210> SEQ ID NO 203
<211> LENGTH: 27
<212> TYPE: DNA
<213> ORGANISM: Caenorhabditis elegans

<400> SEQUENCE: 203

```
gagatgcgta tctctccgcg cgacgat                                             27
```

<210> SEQ ID NO 204
<211> LENGTH: 27
<212> TYPE: DNA
<213> ORGANISM: Caenorhabditis elegans

<400> SEQUENCE: 204

```
actgaggagc ctaaggcagg tgaagcc                                             27
```

<210> SEQ ID NO 205
<211> LENGTH: 27
<212> TYPE: DNA
<213> ORGANISM: Caenorhabditis elegans

<400> SEQUENCE: 205

```
aactatgacg cgagggtagg cactacc                                             27
```

<210> SEQ ID NO 206
<211> LENGTH: 27
<212> TYPE: DNA
<213> ORGANISM: Caenorhabditis elegans

<400> SEQUENCE: 206

```
actaagcgta caaagctcgg agcaacc                                             27
```

<210> SEQ ID NO 207
<211> LENGTH: 25
<212> TYPE: PRT
<213> ORGANISM: Xenopus laevis

<400> SEQUENCE: 207

Tyr Ile Cys Ser Phe Ala Asp Cys Gly Ala Ala Tyr Asn Lys Asn Trp
 1               5                  10                  15

Lys Leu Gln Ala His Leu Cys Lys His
            20                  25

<210> SEQ ID NO 208

```
<211> LENGTH: 30
<212> TYPE: PRT
<213> ORGANISM: Xenopus laevis

<400> SEQUENCE: 208

Thr Gly Glu Lys Pro Phe Pro Cys Lys Glu Glu Gly Cys Glu Lys Gly
1               5                   10                  15

Phe Thr Ser Leu His His Leu Thr Arg His Ser Leu Thr His
            20                  25                  30

<210> SEQ ID NO 209
<211> LENGTH: 31
<212> TYPE: PRT
<213> ORGANISM: Xenopus laevis

<400> SEQUENCE: 209

Thr Gly Glu Lys Asn Phe Thr Cys Asp Ser Asp Gly Cys Asp Leu Arg
1               5                   10                  15

Phe Thr Thr Lys Ala Asn Met Lys Lys His Phe Asn Arg Phe His
            20                  25                  30

<210> SEQ ID NO 210
<211> LENGTH: 31
<212> TYPE: PRT
<213> ORGANISM: Xenopus laevis

<400> SEQUENCE: 210

Asn Ile Lys Ile Cys Val Tyr Val Cys His Phe Glu Asn Cys Gly Lys
1               5                   10                  15

Ala Phe Lys Lys His Asn Gln Leu Lys Val His Gln Phe Ser His
            20                  25                  30

<210> SEQ ID NO 211
<211> LENGTH: 30
<212> TYPE: PRT
<213> ORGANISM: Xenopus laevis

<400> SEQUENCE: 211

Thr Gln Gln Leu Pro Tyr Glu Cys Pro His Glu Gly Cys Asp Lys Arg
1               5                   10                  15

Phe Ser Leu Pro Ser Arg Leu Lys Arg His Glu Lys Val His
            20                  25                  30

<210> SEQ ID NO 212
<211> LENGTH: 29
<212> TYPE: PRT
<213> ORGANISM: Xenopus laevis

<400> SEQUENCE: 212

Ala Gly Tyr Pro Cys Lys Lys Asp Asp Ser Cys Ser Phe Val Gly Lys
1               5                   10                  15

Thr Trp Thr Leu Tyr Leu Lys His Val Ala Glu Cys His
            20                  25

<210> SEQ ID NO 213
<211> LENGTH: 26
<212> TYPE: PRT
<213> ORGANISM: Xenopus laevis

<400> SEQUENCE: 213

Gln Asp Leu Ala Val Cys Asp Val Cys Asn Arg Lys Phe Arg His Lys
1               5                   10                  15
```

-continued

Asp Tyr Leu Arg Asp His Gln Lys Thr His
            20                  25

<210> SEQ ID NO 214
<211> LENGTH: 32
<212> TYPE: PRT
<213> ORGANISM: Xenopus laevis

<400> SEQUENCE: 214

Glu Lys Glu Arg Thr Val Tyr Leu Cys Pro Arg Asp Gly Cys Asp Arg
1               5                   10                  15

Ser Tyr Thr Thr Ala Phe Asn Leu Arg Ser His Ile Gln Ser Phe His
            20                  25                  30

<210> SEQ ID NO 215
<211> LENGTH: 30
<212> TYPE: PRT
<213> ORGANISM: Xenopus laevis

<400> SEQUENCE: 215

Glu Glu Gln Arg Pro Phe Val Cys Glu His Ala Gly Cys Gly Lys Cys
1               5                   10                  15

Phe Ala Met Lys Lys Ser Leu Glu Arg His Ser Val Val His
            20                  25                  30

<210> SEQ ID NO 216
<211> LENGTH: 25
<212> TYPE: PRT
<213> ORGANISM: Xenopus laevis

<400> SEQUENCE: 216

Tyr Lys Cys Gly Leu Cys Glu Arg Ser Phe Val Glu Lys Ser Ala Leu
1               5                   10                  15

Ser Arg His Gln Arg Val His Lys Asn
            20                  25

<210> SEQ ID NO 217
<211> LENGTH: 29
<212> TYPE: PRT
<213> ORGANISM: Saccharomyces cerevisiae

<400> SEQUENCE: 217

Thr Asn Leu Lys Pro Tyr Pro Cys Gly Leu Cys Asn Arg Cys Phe Thr
1               5                   10                  15

Arg Arg Asp Leu Leu Ile Arg His Ala Gln Lys Ile His
            20                  25

<210> SEQ ID NO 218
<211> LENGTH: 23
<212> TYPE: PRT
<213> ORGANISM: Mus musculus

<400> SEQUENCE: 218

Tyr Gly Cys Asp Glu Cys Gly Lys Thr Phe Arg Gln Ser Ser Ser Leu
1               5                   10                  15

Leu Lys His Gln Arg Ile His
            20

<210> SEQ ID NO 219
<211> LENGTH: 28
<212> TYPE: PRT
<213> ORGANISM: Mus musculus

```
<400> SEQUENCE: 219

Thr Gly Glu Lys Pro Tyr Thr Cys Asn Val Cys Asp Lys His Phe Ile
1               5                   10                  15

Glu Arg Ser Ser Leu Thr Val His Gln Arg Thr His
            20                  25

<210> SEQ ID NO 220
<211> LENGTH: 28
<212> TYPE: PRT
<213> ORGANISM: Mus musculus

<400> SEQUENCE: 220

Thr Gly Glu Lys Pro Tyr Lys Cys His Glu Cys Gly Lys Ala Phe Ser
1               5                   10                  15

Gln Ser Met Asn Leu Thr Val His Gln Arg Thr His
            20                  25

<210> SEQ ID NO 221
<211> LENGTH: 28
<212> TYPE: PRT
<213> ORGANISM: Mus musculus

<400> SEQUENCE: 221

Thr Gly Glu Lys Pro Tyr Gln Cys Lys Glu Cys Gly Lys Ala Phe Arg
1               5                   10                  15

Lys Asn Ser Ser Leu Ile Gln His Glu Arg Ile His
            20                  25

<210> SEQ ID NO 222
<211> LENGTH: 28
<212> TYPE: PRT
<213> ORGANISM: Mus musculus

<400> SEQUENCE: 222

Thr Gly Glu Lys Pro Tyr Lys Cys His Asp Cys Glu Lys Ala Phe Ser
1               5                   10                  15

Lys Asn Ser Ser Leu Thr Gln His Arg Arg Ile His
            20                  25

<210> SEQ ID NO 223
<211> LENGTH: 28
<212> TYPE: PRT
<213> ORGANISM: Mus musculus

<400> SEQUENCE: 223

Thr Gly Glu Lys Pro Tyr Glu Cys Met Ile Cys Gly Lys His Phe Thr
1               5                   10                  15

Gly Arg Ser Ser Leu Thr Val His Gln Val Ile His
            20                  25

<210> SEQ ID NO 224
<211> LENGTH: 28
<212> TYPE: PRT
<213> ORGANISM: Mus musculus

<400> SEQUENCE: 224

Thr Gly Glu Lys Pro Tyr Glu Cys Thr Glu Cys Gly Lys Ala Phe Ser
1               5                   10                  15

Gln Ser Ala Tyr Leu Ile Glu His Arg Arg Ile His
            20                  25
```

<210> SEQ ID NO 225
<211> LENGTH: 28
<212> TYPE: PRT
<213> ORGANISM: Mus musculus

<400> SEQUENCE: 225

Thr Gly Glu Lys Pro Tyr Glu Cys Asp Gln Cys Gly Lys Ala Phe Ile
1               5                   10                  15

Lys Asn Ser Ser Leu Ile Val His Gln Arg Ile His
            20                  25

<210> SEQ ID NO 226
<211> LENGTH: 28
<212> TYPE: PRT
<213> ORGANISM: Mus musculus

<400> SEQUENCE: 226

Thr Gly Glu Lys Pro Tyr Gln Cys Asn Glu Cys Gly Lys Pro Phe Ser
1               5                   10                  15

Arg Ser Thr Asn Leu Thr Arg His Gln Arg Thr His
            20                  25

<210> SEQ ID NO 227
<211> LENGTH: 23
<212> TYPE: PRT
<213> ORGANISM: Drosophila melanogaster

<400> SEQUENCE: 227

Phe Thr Cys Lys Ile Cys Ser Arg Ser Phe Gly Tyr Lys His Val Leu
1               5                   10                  15

Gln Asn His Glu Arg Thr His
            20

<210> SEQ ID NO 228
<211> LENGTH: 28
<212> TYPE: PRT
<213> ORGANISM: Drosophila melanogaster

<400> SEQUENCE: 228

Thr Gly Glu Lys Pro Phe Glu Cys Pro Glu Cys Asp Lys Arg Phe Thr
1               5                   10                  15

Arg Asp His His Leu Lys Thr His Met Arg Leu His
            20                  25

<210> SEQ ID NO 229
<211> LENGTH: 28
<212> TYPE: PRT
<213> ORGANISM: Drosophila melanogaster

<400> SEQUENCE: 229

Thr Gly Glu Lys Pro Tyr His Cys Ser His Cys Asp Arg Gln Phe Val
1               5                   10                  15

Gln Val Ala Asn Leu Arg Arg His Leu Arg Val His
            20                  25

<210> SEQ ID NO 230
<211> LENGTH: 28
<212> TYPE: PRT
<213> ORGANISM: Drosophila melanogaster

<400> SEQUENCE: 230

Thr Gly Glu Lys Pro Tyr Thr Cys Glu Ile Cys Asp Gly Lys Phe Ser
1               5                   10                  15

-continued

```
Asp Ser Asn Gln Leu Lys Ser His Met Leu Val His
             20                  25

<210> SEQ ID NO 231
<211> LENGTH: 5
<212> TYPE: PRT
<213> ORGANISM: Drosophila melanogaster

<400> SEQUENCE: 231

Thr Gly Glu Lys Pro
1               5
```